United States Patent
Chung et al.

[19]

[11] Patent Number: 6,057,358

[45] Date of Patent: May 2, 2000

[54] AMINE DERIVATIVES, PROCESSES FOR PRODUCING THEM AND A USE OF THEM AS ANTIARRHYTHMIC DRUGS

[75] Inventors: You Sup Chung; Hak Yeop Kim; Kyung Yun Jung; Jae Ki Min, all of Kyunggi-do, Rep. of Korea; Shigeru Tanabe, Shizuoka-ken, Japan

[73] Assignee: C&C Research Labs., Kyunggi-do, Rep. of Korea

[21] Appl. No.: 08/776,612

[22] PCT Filed: Jun. 7, 1995

[86] PCT No.: PCT/JP95/01138

§ 371 Date: May 27, 1997

§ 102(e) Date: May 27, 1997

[87] PCT Pub. No.: WO96/04231

PCT Pub. Date: Feb. 15, 1996

[30] Foreign Application Priority Data

Aug. 4, 1994 [JP] Japan ............................... 6-183664

[51] Int. Cl.⁷ ..................... C07D 233/61; C07C 255/34; C07C 215/28

[52] U.S. Cl. .................. 514/427; 514/428; 514/429; 514/603; 514/620; 548/340.1; 548/561; 558/412; 558/413; 564/99; 564/161; 564/305; 564/341; 564/353; 564/369; 564/354; 564/371; 564/372; 564/374; 564/384; 564/389; 564/391

[58] Field of Search .............. 564/99, 161, 369, 564/370, 371, 372, 374, 384, 389, 391, 305, 341, 353, 354; 558/413, 412; 548/340.1, 214, 536, 561; 514/399, 524, 428, 427, 429, 603, 620

[56] References Cited

U.S. PATENT DOCUMENTS 4,959,366  9/1990  Cross et al. ........................ 514/239.5

5,079,248  1/1992  Cross et al. ........................ 514/237.5

FOREIGN PATENT DOCUMENTS

WO 96 00715  1/1996  WIPO .

*Primary Examiner*—Johann Richter
*Assistant Examiner*—Ebenezer Sackey
*Attorney, Agent, or Firm*—Browdy and Neimark

[57] ABSTRACT

Novel amine derivatives of the following general formula (I):

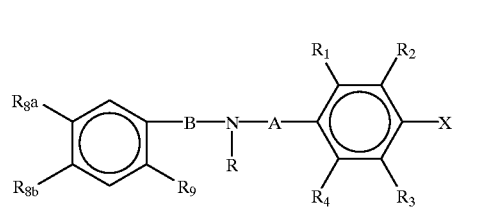

(wherein)

A may denote —$(CH_2)$—O—, —$(CH_2)_2$—O—, or —$(CH_2)_2$—NH—;

B may denote —$(CH_2)_2$—;

$R_1$ may denote a hydrogen atom, a halogen atom, a nitro group, a 1-pyrrolyl group, an acetamido group, an amino group or a dimethylamino group;

$R_2$ may denote a hydrogen atom or a nitro group;

$R_3$ and $R_4$ may denote a hydrogen atom;

$R_{8a}$ and $R_{8b}$ which are the same may denote a chlorine atom or a methoxy group;

$R_9$ may denote a hydrogen atom or an amino group;

R may denote a methyl group; and

X may denote a methanesulfonamido group, a 1-imidazolyl group or a nitro group or a salts thereof are useful as antiarrhythmic drugs.

18 Claims, No Drawings

AMINE DERIVATIVES, PROCESSES FOR PRODUCING THEM AND A USE OF THEM AS ANTIARRHYTHMIC DRUGS

This application is a 371 of PCT/JP95/01138 filed on Jun. 7, 1995.

TECHNICAL FIELD

This invention relates to amine derivatives useful as antiarrhythmic drugs. More specifically, the invention relates to amine derivatives of the following general formula (I) which have a potassium channel blocking action to be useful as, for example, antiarrhythmic drugs and salts thereof:

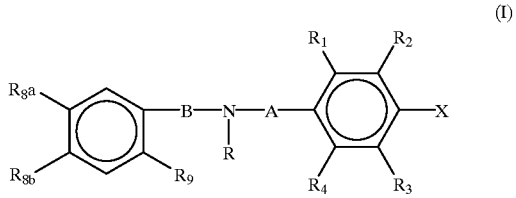

(wherein)

A denotes the general formula $-(CH_2)_m-$, $-(CH_2)_m-O-$, $-(CH_2)_m-NH-$ or $-(CH_2)_m-SO_2-$, where a hydrogen atom in the $-(CH_2)_m-$ moiety may be substituted by one or more hydroxyl groups;

B denotes a group of the general formula $-(CH_2)_n-$, $-NR_7-(CH_2)_n-$ or $-CONH-(CH_2)_n-$;

$R_1$, $R_2$, $R_3$ and $R_4$ denote each independently a hydrogen atom, a halogen atom, a cyano group, a lower alkyl group, a lower alkoxy group, a lower alkanoyl group, a nitro group, a hydroxyl group, a lower alkylsulfonyloxy group, a phenoxymethyl group, a heterocyclic group or the group of the general formula $-NR_5R_6$, where $R_5$ and $R_6$ denote each independently a hydrogen atom, a lower alkanoyl group, a lower alkyl group or a heterocyclic group;

$R_9$ denotes a hydrogen atom, a nitro group, an amino group, a halogen atom, a lower alkyl group, a lower alkanoylamino group or a lower alkylamino group;

$R_{8a}$ and $R_{8b}$ denote the same halogen atom or lower alkoxy group or, alternatively, when $R_{8a}$ is a hydrogen atom, $R_{8b}$ denotes a lower alkylsulfonylamino group or a halogen atom (provided that when $R_{8a}$ is a hydrogen atom and $R_{8b}$ is a lower alkylsulfonylamino group, $R_1$ denotes a group of the general formula $-NR_5R_6$ or a heterocyclic group);

R denotes a lower alkyl group or an aryl group;

$R_7$ denotes a hydrogen atom or a lower alkyl group;

X denotes a group of the general formula $-NR_{10}R_{11}$, a nitro group, a cyano group or a heterocyclic group, where $R_{10}$ and $R_{11}$, denote each independently a hydrogen atom or a lower alkylsulfonyl group;

m denotes an integer of from 0 to 3; and n denotes an integer of from 0 to 3.

The invention also embraces processes for producing the amine derivatives of the general formula (I) set forth above and salts thereof, as well as a use of them as antiarrhythmic drugs.

TECHNICAL BACKGROUND

Potassium channels which are one of the mechanisms that control systemic physiological actions are distributed in systemic cellular systems including pancreatic β-cells and cardiac muscle and, therefore, drugs that have pharmacological actions to control potassium channels are currently used in the treatment of various circulatory diseases as, for example, antidiabetic drugs, antiarrhythmic drugs, etc. A number of compounds are known in the prior art as such potassium channel blockers. For example, glybenclamide which is an oral antidiabetic drug that blocks potassium channels in pancreatic β-cells has been reported to block ATP-dependent potassium channels in pancreatic β-cells and thereby induce insulin release, hence exhibiting a hypoglycemic action; this action is considered to be a mechanism of action common to oral antidiabetic drugs having the basic structure of sulfonylureas as the skeleton. In this connection, 4-substituted benzoic acid derivatives are known to have the same action as reported in two reference, European Journal of Pharmacology, 141, 243–251 (1987) and British Journal of Pharmacology, 93, 61–68 (1988). On the other hand, compounds that block potassium channels in the cardiac muscle have an antiarrhythmic action and, according to Vaughan Williams, they are classified as antiarrhythmic drugs of class III (see Anti-Arrhythmic Action, E. M. Vaughan Williams, Academic Press, 1980). Examples of such compounds have recently been put forward in Japanese Patent Publication No. Hei 3-60814 and European Patent Publication No. 0245997 as antiarrhythmic drugs that are compounds represented by the following general formula (A):

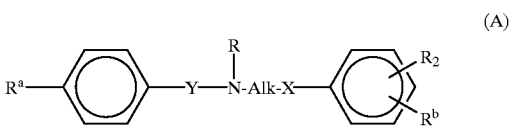

$R^a$ is $-NO_2$, $-NH_2$ or $-NHSO_2R^1$, where $R^1$ is a $C_1-C_4$ alkyl group;

$R^b$ is $-NO_2$, $-NH_2$ or $R^3$, where $R^3$ is $-NHSO_2$ ($C_1-C_4$ alkyl) or $-CONR^4R^5$;

$R^4$ and $R^5$ denote each independently a $C_1-C_4$ alkyl or, when taken together with the nitrogen atom to which they are bound, denote a 1-pyrrolidinyl, piperidino, morpholino or N-methylpiperazin-1-yl group, provided that when one of $R^a$ and $R^b$ is $-NO_2$, the other is not $-NH_2$;

X denotes O, S or a direct bond;

Y is an ethylene group optionally substituted by a methyl group;

"Alk" is an ethylene, trimethylene or tetramethylene group that are optionally substituted by a methyl group;

R is a $C_1-C_4$ alkyl; and $R^2$ is H, halogen, $CF_3$ or $C_1-C_4$ alkyl.

However, the so far proposed prior art potassium channel blocking antiarrhythmic drugs including the above-described compounds are not necessarily satisfactory in their action and even those which have a certain degree of activity have problems such as the manifestation of serious side effects and it is strongly desired today to develop potent and safe antiarrhythmic drugs that have an outstanding potassium channel blocking action and which yet are substantially free from side effects and hence can safely be used.

Under these circumstances, the present inventors studied a wide variety of compound species for their potassium channel blocking action and their utility as antiarrhythmic drugs and confirmed, as a result, that specified novel amines of the general formula (I) defined above and salts thereof were less in side effects while exhibiting a potent potassium channel blocking action. The present invention has been accomplished on the basis of this finding.

DISCLOSURE OF INVENTION

Therefore, the present invention relates to novel amine derivatives of the general formula (I) and salts thereof:

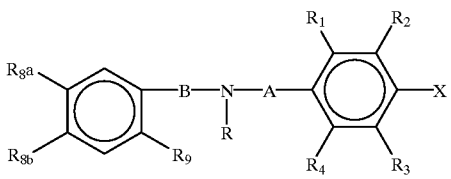

(wherein

A denotes the general formula —(CH$_2$)$_m$—, —(CH$_2$)$_m$—O—, —(CH$_2$)$_m$—NH— or —(CH$_2$)$_m$—SO$_2$—, where a hydrogen atom in the —(CH$_2$)$_m$— moiety may be substituted by one or more hydroxyl groups;

B denotes the general formula —(CH$_2$)$_n$—, —NR$_7$—(CH$_2$)$_n$— or —CONH—(CH$_2$)$_n$—;

R$_1$, R$_2$, R$_3$ and R$_4$ denotes each independently a hydrogen atom, a halogen atom, a cyano group, a lower alkyl group, a lower alkoxy group, a lower alkanoyl group, a nitro group, a hydroxyl group, a lower alkylsulfonyloxy group, a phenoxymethyl group, a heterocyclic group or the group of the general formula —NR$_5$R$_6$, where R$_5$ and R$_6$ denote each independently a hydrogen atom, a lower alkanoyl group, a lower alkyl group or a heterocyclic group;

R$_9$ denotes a hydrogen atom, a halogen atom, a nitro group, an amino group, a lower alkyl group, a lower alkanoylamino group or a lower alkylamino group;

R$_{8a}$ and R$_{8b}$ denote the same halogen atom or lower alkoxy group or, alternatively, when R$_{8a}$ is a hydrogen atom, R$_{8b}$ denotes a lower alkylsulfonylamino group or a halogen atom (provided that when R$_{8a}$ is a hydrogen atom and R$_{8b}$ is a lower alkylsulfonylamino group, R$_1$ denotes a group of the general formula —NR$_5$R$_6$ or a heterocyclic group);

R denotes a lower alkyl group or an aryl group;

R$_7$ denotes a hydrogen atom or a lower alkyl group;

X denotes a group of the general formula —NR$_{10}$R$_{11}$, a nitro group, a cyano group or a heterocyclic group, where R$_{10}$ and R$_{11}$ denote each independently a hydrogen atom or a lower alkylsulfonyl group;

m denotes an integer of from 0 to 3; and n denotes an integer of from 0 to 3.

BEST MODE FOR CARRYING OUT THE INVENTION

The expressions of various substituents in the invention will have the following meanings unless otherwise noted.

The halogen atom denotes a fluorine atom, a chlorine atom, a bromine atom or an iodine atom.

The lower alkyl group denotes a straight-chained or branched alkyl group having 1–6, preferably 1–4, carbon atoms, as exemplified by a methyl group, an ethyl group, a n-propyl group, an i-propyl group, a n-butyl group, an i-butyl group, a s-butyl group and a t-butyl group.

The lower alkoxy group denotes a straight-chained or branched alkoxy group having 1–6, preferably 1–4, carbon atoms, as exemplified by a methoxy group, an ethoxy group, a n-propoxy group, an i-propoxy group, a n-butoxy group, an i-butoxy group, a s-butoxy group and a t-butoxy group.

The lower alkanoyl group has the meaning of an alkylcarbonyl group having 1–6, preferably, 1–4, carbon atoms in the alkyl moiety, as exemplified by an acetyl group, a propionyl group, a n-butyryl group, an i-butyryl group, a valeryl group, an isovaleryl group and a pivaloyl group.

The lower alkylsulfonyloxy group means an alkylsulfonyloxy group having 1–6, preferably 1–4, carbon atoms, as exemplified by a methylsulfonyloxy group, an ethylsulfonyloxy group, a n-propylsulfonyloxy group, an i-propylsulfonyloxy group, a n-butylsulfonyloxy group, an i-butylsulfonyloxy group, a s-butylsulfonyloxy group and a t-butylsulfonyloxy group.

The heterocyclic group means a saturated or unsaturated group containing optionally fusable 3- to 6-membered rings having at least one nitrogen, oxygen or sulfur atom, as exemplified by a pyrrolyl group, a thienyl group, a furyl group, a pyranyl group, an imidazolyl group, a pyrazolyl group, a thiazolyl group, an isothiazolyl group, an isoxazolyl group, a pyridyl group, a pyrazinyl group, a pyrimidinyl group, a pyridazinyl group, an indolyl group, an indazoyl group, a quinolyl group, an isoquinolyl group, a phthalazinyl, a naphthyridinyl group, a quinoxalinyl group, a quinazolinyl group, a furazanyl group, an aziridinyl group, an azetidinyl group, a pyrrolidinyl group and a piperidinyl group.

The lower alkanoylamino group means a lower alkanoyl group having an amino group bonded thereto, as exemplified by an acetylamino group, a propionylamino group, a n-butyrylamino group, an i-butyrylamino group, a valerylamino group, an isovalerylamino group and a pivaloylamino group.

The lower alkylamino group means a lower alkyl group having an amino group bonded thereto, as exemplified by a methylamino group, an ethylamino group, a n-propylamino group, an i-propylamino group, a n-butylamino group, an i-butylamino group, a s-butylamino group and a t-butylamino group.

The aryl group means an aromatic hydrocarbon freed of one hydrogen atom, as exemplified by a phenyl group, a tolyl group, a xylyl group, a biphenyl group, a naphthyl group, an anthryl group and a phenanthryl group, with a phenyl group being preferred.

As already referred to, the invention compounds of the general formula (I) set forth above have a potent potassium channel blocking action as antiarrhythmic drugs of class III and prolong the duration of action potential in the cardiac muscle and conduction tissues to thereby make them more refractory to premature stimuli. These are effective on the atrium, ventricle and conduction tissues in all of in vivo and in vitro cases and, hence, are useful in the prevention and treatment of ventricular and supraventricular dysrhythmias of various kinds including atrial and ventricular fibrillations. These compounds do not change the conduction velocity of impulses and, hence, compared to other antiarrhythmic drugs (mostly in class I) which are presently in customary use, they are less prone to accelerate or aggravate dysrhythmias and, in addition, they will cause less nervous side effects. It should also be noted that some of these compounds have a certain degree of positive inotropic activity and hence are particularly useful in patients whose heart pump function is damaged.

Among the invention compounds of the general formula (I), desirable are those compounds, in which A denotes a group of the general formula —(CH$_2$)$_m$—, —(CH$_2$)$_m$—O—, —(CH$_2$)$_m$—NH— or —(CH$_2$)$_m$—SO$_2$, where a hydrogen atom in the —(CH$_2$)$_m$— moiety may be substituted by at least one hydroxyl group;

B denotes a group of the general formula —(CH$_2$)$_n$, —NR$_7$—(CH$_2$)$_n$— or —CONH—(CH$_2$)$_n$—;

R$_1$, R$_2$, R$_3$ and R$_4$ denote each independently a hydrogen atom, a halogen atom, a cyano group, a lower alkyl group having 1–6 carbon atoms, a lower alkoxy group having 1–6 carbon atoms, a lower alkanoyl group having 1–6 carbon atoms in the alkyl moiety, a nitro group, a hydroxyl group, a lower alkylsulfonyloxy group having 1–6 carbon atoms, a phenoxymethyl group, a 5-membered heterocyclic group or a group of the general formula —$NR_5R_6$, where $R_5$ and $R_6$ denote each independently a hydrogen atom, a lower alkanoyl group having 1–6 carbon atoms in the alkyl moiety, a lower alkyl group having 1–6 carbon atoms or a 5- or 6-membered heterocyclic group;

$R_9$ denotes a hydrogen atom, a halogen atom, a nitro group, an amino group, a lower alkanoylamino group having 1–6 carbon atoms in the alkyl moiety or a lower alkylamino group having 1–6 carbon atoms;

$R_{8a}$ and $R_{8b}$ denote the same halogen atom or lower alkoxy group having 1–6 carbon atoms;

R denotes a lower alkyl group having 1–6 carbon atoms or a phenyl group;

$R_7$ denotes a hydrogen atom or a lower alkyl group having 1–6 carbon atoms;

X denotes a group of the general formula —$NR_{10}R_{11}$, a nitro group, a cyano group or an imidazolyl group, where $R_{10}$ and $R_{11}$ denote each independently a hydrogen atom or a lower alkyl sulfonyl group having 1–6 carbon atoms;

m denotes an integer of from 0 to 2; and n denotes an integer of from 0 to 2.

Among these desirable compounds, particularly desirable are those compounds of the general formula (I), in which A denotes a group of the general formula —$(CH_2)_m$—, —$(CH_2)_m$—O—, —$(CH_2)_m$—NH— or —$(CH_2)_m$—$SO_2$—, where a hydrogen atom in the —$(CH_2)_m$— moiety may be substituted by at least one hydroxyl group;

B denotes a group of the general formula —$(CH_2)_n$—, —$NR_7$—$(CH_2)_n$— or —CONH—$(CH_2)_n$—;

$R_1$, $R_2$, $R_3$ and $R_4$ denote each independently a hydrogen atom, a fluorine atom, a chlorine atom, a bromine atom, an iodine atom, a cyano group, a methyl group, a methoxy group, an acetyl group, a nitro group, a hydroxyl group, a methylsulfonyloxy group, a phenoxymethyl group, a pyrrolyl group or a group of the general formula —$NR_5R_6$, where $R_5$ and $R_6$ denote each independently a hydrogen atom, an acetyl group or a methyl group;

$R_9$ denotes a hydrogen atom, a nitro group, an amino group or a lower alkanoylamino group having 1–6 carbon atoms in the alkyl moiety;

$R_{8a}$ and $R_{8b}$ which are the same denote a chlorine atom or a methoxy group;

R denotes a lower alkyl group having 1–3 carbon atoms or a phenyl group;

$R_7$ denotes a hydrogen atom or a methyl group;

X denotes a group of the general formula —$NR_{10}R_{11}$, a nitro group, a cyano group or a 1-imidazolyl group, where $R_{10}$ and $R_{11}$ denote each independently a hydrogen atom or a methylsulfonyl group;

m denotes an integer of from 0 to 2; and n denotes an integer of from 0 to 2.

Among these particularly desirable compounds, more desirable are those compounds of the general formula (I), in which A denotes the group —$(CH_2)_2$—, —$CH_2$—O—, —$(CH_2)_2$—O—, —$CH_2$—NH— or —$(CH_2)_2$—$SO_2$—;

B denotes the group —$(CH_2)_2$—, —CONH—$(CH_2)_2$— or —NH—$(CH_2)_2$—;

$R_1$ denotes a hydrogen atom, a halogen atom, a nitro group, a 1-pyrrolyl group, an acetamide group, an amino group, a dimethylamino group, a cyano group, a lower alkyl group having 1–3 carbon atoms, a hydroxyl group, a methanesulfonyloxy group or a methanesulfonylamido group;

$R_2$ denotes a hydrogen atom, a nitro group or a halogen atom;

$R_3$ denotes a hydrogen atom or a nitro group;

$R_4$ denotes a hydrogen atom, a lower alkyl group having 1–3 carbon atoms or a halogen atom;

$R_{8a}$ and $R_{8b}$ which are the same denote a chlorine atom or a methoxy group;

$R_9$ denotes a hydrogen atom, a lower alkyl group having 1–3 carbon atoms, an amino group or a nitro group;

R denotes a lower alkyl group having 1–3 carbon atoms or a phenyl group; and

X denotes a methanesulfonylamido group, a 1-imidazolyl group, a nitro group or a cyano group.

The most desirable compounds of the general formula (I) are those in which

A denotes —$(CH_2)$—O—, —$(CH_2)_2$—O— or —$(CH_2)_2$—NH—;

B denotes —$(CH_2)_2$—;

$R_1$ denotes a hydrogen atom, a halogen atom, a nitro group, a 1-pyrrolyl group, an acetamide group, an amino group or a dimethylamino group;

$R_2$ denotes a hydrogen atom or a nitro group;

$R_3$ and $R_4$ denote a hydrogen atom;

$R_{8a}$ and $R_{8b}$ which are the same denote a chlorine atom or a methoxy group;

$R_9$ denotes a hydrogen atom, a methyl group, an ethyl group or an amino group;

R denotes a methyl group; and

X denotes a methanesulfonylamido group, a 1-imidazolyl group or a nitro group.

The invention compounds of the general formula (I) may in turn form pharmaceutically acceptable salts. Such pharmaceutically acceptable salts include acid addition salts formed with pharmaceutically acceptable, anion-containing nontoxic acid addition salt forming acids, exemplified by inorganic acids such as hydrochloric acid, sulfuric acid, nitric acid, phosphoric acid, hydrobromic acid and hidrotic acid, organic carboxylic acids such as tartaric acid, formic acid, citric acid, acetic acid, trichloroacetic acid or trifluoroacetic acid, gluconic acid, benzoic acid, lactic acid, fumaric acid and maleic acid, and sulfonic acids such as methanesulfonic acid, benzenesulfonic acid, p-toluenesulfonic acid and naphthalenesulfonic acid. Specific examples of such salts include hydrochlorides, hydrobromides, hydroiodides, sulfates or hydrogensulfates, phosphates or hydrogenphosphates, acetates, maleates, fumarates, lactates, tartrates, citrates, gluconates, benzoates, methanesulfonates, benzenesulfonates and p-toluenesulfonates.

The present invention further relates to processes for producing the novel amine derivatives of the general formula (I) set forth above or salts thereof. According to the invention, the amine derivatives of the general formula (I) or salts thereof can be produced by processes characterized by:

(A) reacting a compound of the general formula (II) set forth below or a salt thereof with a compound of the general formula (II) set forth below or a salt thereof;

(B) reducing a compound of the general formula (Ia) set forth below or a salt thereof to produce a compound of the general formula (Ib) or a salt thereof;

(C) reacting a compound of the general formula (Ic) set forth below or a salt thereof with an alkanesulfonyl halide to produce a compound of the general formula (Id) set forth below or a salt thereof;

(D) reacting a compound of the general formula (II) set forth below or a salt thereof with a compound of the general formula (IV) or a salt thereof to produce a compound of the general formula (V) or a salt thereof and reacting the thus produced compound (V) with a compound of the general formula (VI) or a salt thereof to produce a compound of the general formula (Ie) or a salt thereof; or (E) reacting a compound of the general formula (VII) set forth below or a salt thereof with a compound of the general formula (VIII) or a salt thereof to produce a compound of the general formula (If) or a salt thereof.

These processes of the invention may be represented by the following reaction schemes.

Process A

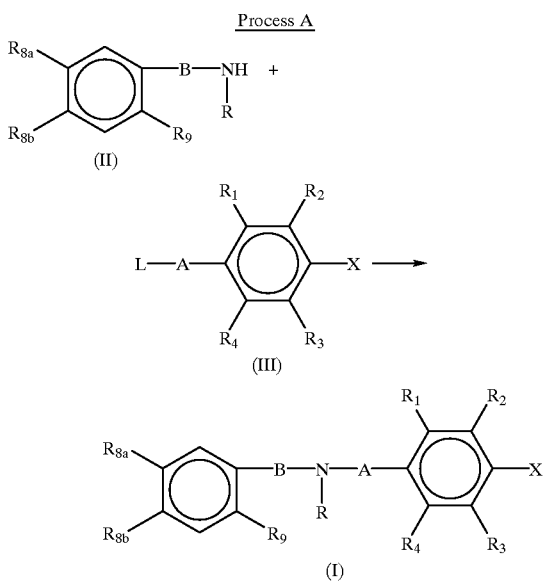

(II)

(III)

(I)

Process B

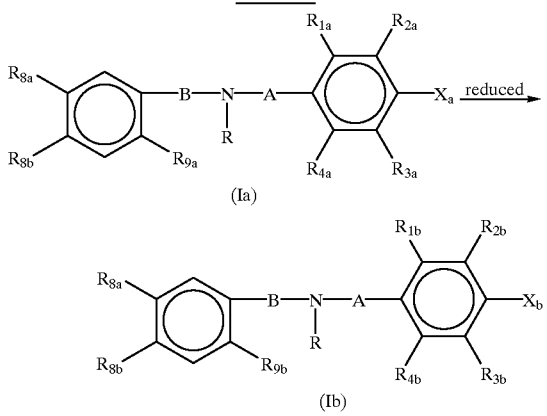

(Ia)

(Ib)

Process C

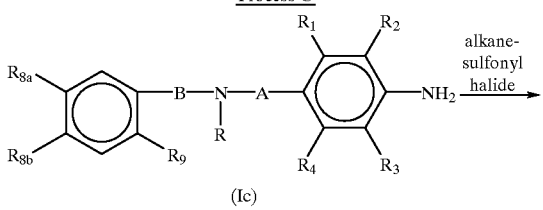

(Ic)

-continued

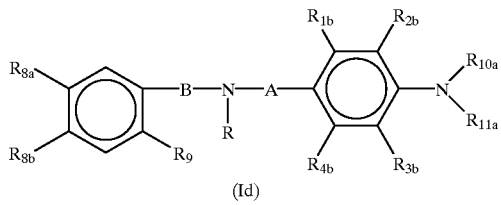

(Id)

Process D

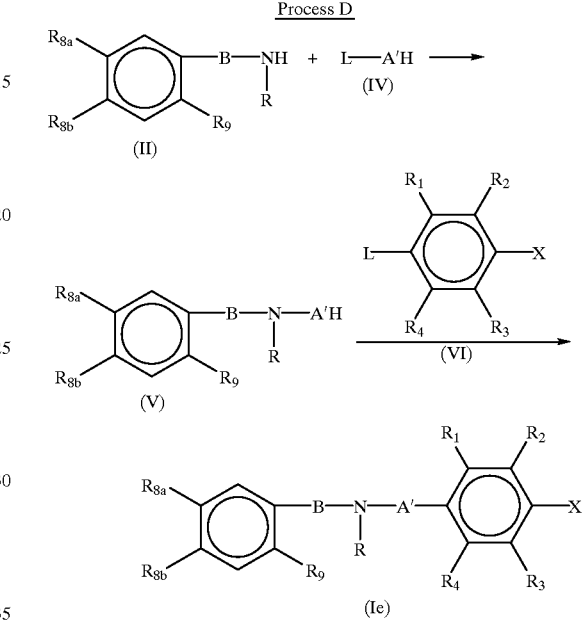

(II)

(V)

(Ie)

Process E

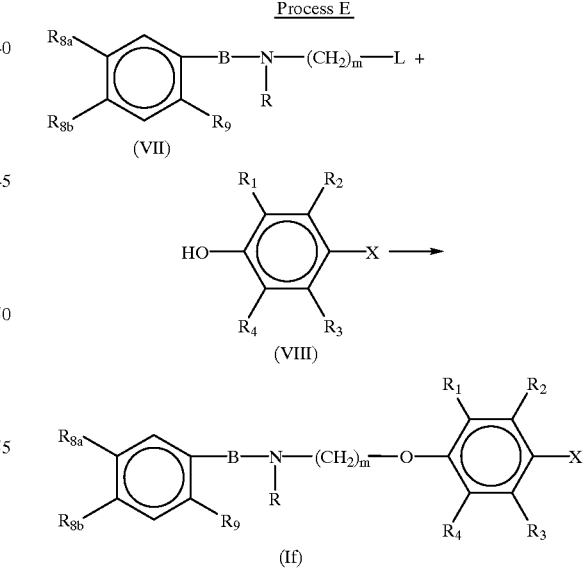

(VII)

(VIII)

(If)

In these reaction schemes,

A denotes a group of the general formula $-(CH_2)_m-$, $-(CH_2)_m-O-$, $-(CH_2)_m-NH-$ or $-(CH_2)_m-SO_2-$, where a hydrogen atom in the $-(CH_2)_m-$ moiety may be substituted by at least one hydroxyl group;

B denotes a group of the general formula —$(CH_2)_2$—, —$(NR_7)$—$(CH_2)_n$— or —CONH—$(CH_2)_n$—;

$R_1$, $R_2$, $R_3$ and $R_4$ denote each independently a hydrogen atom, a halogen atom, a cyano group, a lower alkyl group, a lower alkoxy group, a lower alkanoyl group, a nitro group, a hydroxy group, a lower alylsulfonyloxy group, a phenoxymethyl group, a heterocyclic group or a group of the general formula —$NR_5R_6$, where $R_5$ and $R_6$ denote each independently a hydrogen atom, a lower alkanoyl group, a lower alkyl group or a heterocyclic group;

$R_9$ denotes a hydrogen atom, a nitro group, an amino group, a lower alkyl group, a lower alkanoylamino group, a halogen atom or a lower alkylamino group;

$R_{8a}$ and $R_{8b}$ denote the same halogen atom or lower alkoxy group or, alternatively, when $R_{8a}$ denotes a hydrogen atom, $R_{8b}$ denotes a lower alkylsulfonylamino group or a halogen atom (provided that when $R_{8a}$ is a hydrogen atom and $R_{8b}$ is a lower alkylsulfonylamino group, $R_1$ denotes a group of the general formula —$NR_5R_6$ or a heterocyclic group);

R denotes a lower alkyl group or an aryl group;

$R_7$ denotes a hydrogen atom or a lower alkyl group;

X denotes a group of the general formula —$NR_{10}R_{11}$, a nitro group, a cyano group or a heterocyclic group, where $R_{10}$ and $R_{11}$ denote each independently a hydrogen atom or a lower alkylsulfonyl group;

m denotes an integer of from 0 to 3;

n denotes an integer of from 0 to 3;

L denotes a reactive leaving group exemplified by a halogen atom such as chlorine, bromine or iodine, an alkylsulfonyloxy group such as a methanesulfonyloxy group, a benzenesulfonyloxy group or a toluenesulfonyloxy group;

A' has the same meaning as A, except that it is not —$(CH_2)_m$—;

one of $R_{10a}$ and $R_{11a}$ is a hydrogen atom while the other is a lower alkylsulfonyl group;

$R_{1a}$, $R_{2a}$, $R_{3a}$, $R_{4a}$, $R_{9a}$ and $X_a$ have the same meanings as the above $R_1$, $R_2$, $R_3$, $R_4$, $R_9$ and X, respectively, provided that at least one is a nitro group; and $R_{1b}$, $R_{2b}$, $R_{3b}$, $R_{4b}$, $R_{9b}$ and X, have the same meanings as the above $R_1$, $R_2$, $R_3$, $R_4$, $R_9$ and X, respectively, provided that at least one of them is an amino group.

The processes A to E for producing the invention compounds of the general formula (I) will now be described more specifically below seriatim.

Process A

According to the invention process A, a phenylamine derivative of the general formula (II) or a salt thereof is reacted with a compound of the general formula (III) or a salt thereof to produce a compound of the general formula (I) or a salt thereof.

The reaction in process A can generally be carried out in the presence or absence of an acid acceptor, desirably in an organic solvent. In the reaction, any organic solvents that will not affect it adversely may be employed and, desirably, the reaction is carried out using an alcohol solvent such as methanol or ethanol, a halogenated hydrocarbon solvent such as chloroform or methylene chloride, as well as dimethyl sulfoxide, dimethylformamide, acetone, etc. The reaction may also be carried out in the presence of an acid acceptor and particularly in the case where the reactive leaving group L is a halogen, namely, chlorine, bromine or iodine, it is sometimes advantageous to carry out the reaction in the presence of an acid acceptor. If the reaction is to be carried out in the presence of an acid acceptor, ordinary acid acceptors can desirably be employed, as exemplified by pyridine, triethylamine, potassium carbonate, potassium bicarbonate, sodium methoxide, 1,8-diazabicyclo[5.4.0]-undec-7-ene (DBU), etc.

The reaction in process A may be carried out over a comparatively broad temperature range; generally, it is carried out at room temperature or under elevated temperatures, desirably at the reflux temperature of the solvent used or a temperature of from 50 to 150° C. The reaction is generally carried out for 0.5 to 24 h, desirably for 1 to 15 h.

After the reaction is complete, the reaction product may optionally be separated and purified by methods of post-treatment customary in the technical field of interest, as exemplified by column chromatography and recrystallization.

Process B

According to the invention process B, a compound of the general formula (Ia), which is a compound of the general formula (I) where at least one of $R_1$, $R_2$, $R_3$, $R_4$, $R_9$ and X denotes a nitro group, or a salt thereof is reduced to produce a compound of the general formula (Ib) or a salt thereof.

The reduction reaction may be carried out by reduction methods commonly employed in the art to reduce the nitro group to the amino group. Such reduction methods include an indirect reduction method that causes reduction using hydrogen in the presence of a catalyst such as platinum, palladium, palladium on carbon, platinum on carbon or Raney's nickel, and a direct reduction method that causes reduction using a chemical reductant such as $SnCl_2$, Zn, $Na_2S$, aluminum amalgam, chromos chloride, sodium thiosulfate, sodium borohydride or lithium aluminum hydride.

In the reduction reaction, the catalyst is used generally at a ratio of 0.1–10 moles, desirably at a ratio of 1–5 moles, to one mole of the compound (Ia). The reaction is generally carried out at normal pressures but it may also be carried out at a slightly elevated pressure. The reaction time is generally from 0.5 to 24 h, desirably from 1 to 15 h.

After the reaction is complete, the reaction product may optionally be separated and purified by methods of post-treatment customary in the technical field of interest, as exemplified by column chromatography and recrystallization.

Process C

According to the invention process C, a compound of the general formula (Ic) or a salt thereof is reacted with an alkanesulfonyl halide to produce a compound of the general formula (Id) or a salt thereof.

The alkanesulfonyl halide that may be used in the reaction in process C is an alkanesulfonyl chloride or bromide and methanesulfonyl chloride is desirably used.

The reaction in process C can generally be carried out in the presence of an acid acceptor, desirably in an organic solvent. In the reaction, any organic solvents that will not affect it adversely may be employed and, desirably, the reaction is carried out using an alcohol solvent such as methanol or ethanol, a halogenated hydrocarbon solvent such as chloroform or methylene chloride, as well as dimethyl sulfoxide, dimethylformamide, acetone, etc. The reaction is more advantageously carried out in the presence of an acid acceptor and acid acceptors that fit the purpose are ordinary acid acceptors such as alkali metal hydroxides, carbonates, bicarbonates or alkoxides such as sodium hydroxide, potassium hydroxide, sodium carbonate, sodium bicarbonate, potassium carbonate, potassium bicarbonate and sodium methoxide, as well as pyridine, triethylamine and 1,8-diazabicyclo[5.4.0]undec-7-ene (DBU), with pyridine being particularly desirably.

While the reaction temperature is not limited in any particular way, it is generally desirable to carry out the reaction at room temperature. Generally, the reaction is carried out for 1 to 15 h, desirably for 2 to 5 h.

After the reaction is complete, the reaction product may optionally be separated and purified by methods of post-treatment customary in the technical field of interest, as exemplified by column chromatography and recrystallization.

Process D

According to the invention process (D), a compound of the general formula (II) or a salt thereof is reacted with a compound of the general formula (IV) or a salt thereof to produce a compound of the general formula (V) or a salt thereof and, thereafter, in the second stage, the compound of the general formula (V) or salt thereof is reacted with a compound of the general formula (VI) or a salt thereof to produce a compound of the general formula (Ie) or a salt thereof.

The reaction in the first stage of the process can generally be carried out in the presence or absence of an acid acceptor, desirably in an organic solvent. In the reaction, any organic solvents that will not affect it adversely may be employed and, desirably, the reaction is carried out using an alcohol solvent such as methanol or ethanol, a halogenated hydrocarbon solvent such as chloroform or methylene chloride, as well as dimethyl sulfoxide, dimethylformamide, etc. The reaction may also be carried out in the presence of an acid acceptors and particularly in the case where the reactive leaving group L is a halogen, namely, chlorine, bromine or iodine, it is sometimes advantageous to carry out the reaction in the presence of an acid acceptor. If the reaction is to be carried out in the presence of an acid acceptor, ordinary acid acceptor can desirably be employed, as exemplified by pyridine, triethylamine, potassium iodide, potassium carbonate, potassium bicarbonate, sodium methoxide, 1,8-diazabicyclo[5.4.0]undec-7-ene (DBU), etc.

The reaction may be carried out over a comparatively broad temperature range; generally it is carried out at room temperature or under elevated temperatures, desirably at the reflux temperature of the solvent used or a temperature of from 50 to 150° C. The reaction is generally carried out for 0.5 to 24 h, desirably for 1 to 5 h.

After the reaction is complete, the reaction product may optionally be separated and purified by methods of post-treatment customary in the technical field of interest, as exemplified by column chromatography and recrystallization.

After the end of the reaction in the first stage, the produced compound of the general formula (V) or a salt thereof is subjected to the reaction in the second stage, namely, it is reacted with a compound of the general formula (VI) or a salt thereof to produce a compound of the general formula (Ie) or a salt thereof.

The reaction in the second stage of process D can generally be carried out in the presence or absence of an acid acceptor, desirably in an organic solvent. In the reaction, any organic solvents that will not affect it adversely may be employed and, desirably, the reaction is carried out using an alcohol solvent such as methanol or ethanol, a halogenated hydrocarbon solvent such as chloroform or methylene chloride, as well as dimethyl sulfoxide, dimethylfomamide, etc. The reaction may also be carried out in the presence of an acid acceptor and particularly in the case where the reactive leaving group L is a halogen, namely, chlorine, bromine or iodine, it is sometimes advantageous to carry out the reaction in the presence of an acid acceptor. If the reaction is to be carried out in the presence of an acid acceptor, ordinary acid acceptors can desirably be employed, as exemplified by pyridine, triethylamine, potassium iodide, potassium carbonate, potassium bicarbonate, sodium hydride, sodium methoxide, 1,8-diazabicyclo[5.4.0]undec-7-ene (DBU), etc.

The reaction may be carried out over a comparatively broad temperature range; generally, it is carried out at room temperature or under elevated temperatures, desirably at room temperature. The reaction is generally carried out for 1 to 24 h, desirably for 3 to 5 h.

After the reaction is complete, the reaction product may optionally be separated and purified by methods of post-treatment customary in the technical field of interest, as exemplified by column chromatography and recrystallization.

Process E

According to the invention process E, a phenylamine derivative of the general formula (VII) or a salt thereof is reacted with a compound of the general formula (VIII) or a salt thereof to produce a compound of the general formula (If) or a salt thereof.

The reaction in process E can generally be carried out in the presence or absence of an acid acceptor, desirably in an organic solvent. In the reaction, any organic solvent that will not affect it adversely may be employed and, desirably, the reaction is carried out using an alcohol solvent such as methanol or ethanol, a halogenated hydrocarbon solvent such as chloroform or methylene chloride, as well as dimethyl sulfoxide, dimethylformamide, acetone, etc. The reaction may also be carried out in the presence of an acid acceptor and particularly in the case where the reactive leaving group L is a halogen, namely, chlorine, bromine or iodine, it is sometimes advantageous to carry out the reaction in the presence of an acid acceptor. If the reaction is to be carried out in the presence of an acid acceptor, ordinary acid acceptors can desirably be employed, as exemplified by pyridine, triethylamine, potassium carbonate, potassium bicarbonate, sodium methoxide, 1,8-diazabicyclo[5.4.0]-undec-7-ene (DBU), etc.

The reaction in process E may be carried out over a comparatively broad temperature range; generally, it is carried out at room temperature or under elevated temperatures, desirably at the reflux temperature of the solvent used or a temperature of from 50 to 150° C. The reaction is generally carried out for 0.5 to 24 h, desirably for 1 to 15 h.

After the reaction is complete, the reaction product may optionally be separated and purified by methods of post-treatment customary in the art technical field of interest, as exemplified by column chromatography and recrystallization.

As mentioned above, the amine derivatives of the general formula (I) or pharmaceutically acceptable salts thereof according to the invention have a potent potassium channel blocking action and, hence, can be employed as clinically useful antiarrhythmic drugs. When these compounds are to be utilized clinically, they can be employed in dosage forms of preparations customary in the pharmaceutical field. Therefore, the present invention also provides antiarrhythmic drug compositions that contain the novel amine derivatives of the general formula (I) or pharmaceutically acceptable salts thereof as an active ingredient.

The pharmaceutical compositions of the invention may further be formulated by customary methods using pharmaceutically acceptable customary vehicles to make preparations customary in the pharmaceutical field, as exemplified by preparations for peroral administration such as tablets, capsules, troches, liquids and suspensions, solutions or suspensions for injection, or injections in the form of a ready-to-use dried powder for injection which is to be reconditioned with distilled water for injection just before use by injection.

The vehicles used for these purposes are customary n the pharmaceutical field and, in the case of preparations for peroral administration, they include binders, lubricants, disintegrators, excipients, solubilizers, dispersants, stabilizers, suspending agents, pigments and flavors and, in the case of injections, they include preservatives, pain reducing agents, solubilizers, stabilizers and isotonic agents. The thus produced pharmaceutical preparations may be administered either perorally or parenterally, for example, by an intravenous, intramuscular or subcutaneous route.

In the case of administering the amine derivatives of the general formula (I) according to the invention for the purpose of treating or preventing dysrhythmias, the dose of administration can be varied in accordance with the condition, body weight, age of the patient and so forth; generally, an adult (with an average body weight of 70 kg) is administered 1 to 60 mg daily in a single application or in up to three divided portions.

The present invention will now be described more specifically with reference to the following examples and experiments but it should be noted that the invention is by no means limited thereto.

EXAMPLE 1

Production of 1-(4-methanesulfonamidophenoxy)-2-[N-(3, 4-dimethoxyphenylethyl)-N-methylamino]ethane hydrochloride (1) 1,2-Dibromoethane (24.4 g, 0.13 mol) and 4-nitrophenol (6 g, 0.044 mol) were dissolved in ethyl alcohol (60 ml) and sodium hydroxide (2 g) was added to the solution. The reaction mixture was refluxed for 24 h and thereafter concentrated under vacuum, followed by column chromatography using a 3:1 solvent system of n-hexane and ethyl acetate as an eluent to yield the end compound 1-(4-nitrophenoxy) -2-bromoethane (5.5 g).

$^1$H-NMR (CDCl$_3$): 8.2(dd,2H), 6.99(dd,2H), 4.39(t,2H), 3.67(t,2H).

(2) 2-(3,4-Dimethoxyphenyl)-N-methylethylamine (4.76 g, 0.024 mol) and 3 g (0.012 mol) of the 1-(4-nitrophenoxy)-2-bromoethane produced in (1) above were added to 40 ml of a 2:1 solvent system of acetonitrile and ethanol and the resulting mixture was refluxed for 4 h, followed by concentration under vacuum. The residue was subjected to column chromatography using a 4:1 solvent system of ethyl acetate and n-hexane as an eluent to yield the end compound 1-(4-nitrophenoxy)-2-[N-(3,4-dimethoxyphenethyl)-N-methylamino]ethane (5.5 g).

$^1$H-NMR (CDCl$_3$): δ8.18(d,2H), 6.95(d,2H), 6.78(m,3H), 4.13(m,2H), 3.85(s,6H), 2.89(m,2H), 2.74(s,4H), 2.43(s,3H)

(3) The 1-(4-nitrophenoxy)-2-[N-(3,4-dimethoxyphenethyl)-N-methylamino]ethane prepared in (2) above in an amount of 5.5 g (0.015 mol) was dissolved in methanol (200 ml) and ethyl acetate (200 ml) and, thereafter, 10% Pd/C (2 g) was added to the resulting reaction solution and the reaction mixture was stirred in hydrogen gas for 8 h, followed by filtration and concentration under vacuum to yield the end compound 1-(4-aminophenoxy)-2-[N-(3,4-dimethoxyphenethyl)-N-methylamino]ethane (5 g).

(4) The 1-(4-aminophenoxy)-2-[N-(3,4-dimethoxyphenethyl)-N-methylamino]ethane prepared in (3) above in an amount of 5 g (15.1 mmol) was dissolved in pyridine (30 ml) and after cooling at 0° C., methanesulfonyl chloride (3.5 g, 30.3 mmol) was added dropwise to the solution over 30 min. The reaction mixture was stirred at room temperature for 1 h and, thereafter, ethanol was added and the solvent pyridine was evaporated, followed by addition of a 10% solution of sodium hydroxide to the residue and extraction with ethyl acetate. The organic layer was washed with water and thereafter the organic extract was dried with magnesium sulfate, followed by evaporation of the solvent. The residue was subjected to column chromatography using a 7:3:1 solvent system of cyclohexane, ethyl acetate and methanol as an eluent to yield the end product (2 g). The resulting product was dissolved in methanol (50 ml) and cooled at 0° C.; to the resulting solution, an ether solution (7 ml) saturated with 1M HCl was added and the mixture was stirred for 30 min, followed by concentration under vacuum to yield the titled compound 1-(4-methanesulfonamidophenoxy)-2-[N-(3,4-dimethoxyphenylethyl)-N-methylamino]ethane hydrochloride (1.4 g).

m.p.: 154.4–155.7° C.

$^1$H-NMR (CD$_3$OD): δ7.14(d,J=8.9Hz,1H,ArH), 6.90(d, J=8.9Hz,1H,ArH)<6.80(m,3H,ArH), 4.27(t,J=5.1Hz,2H, OCH$_2$CH$_2$), 3.71(s,6H,CH$_3$OX2), 3.56(bs,2H,OCH$_2$CH$_2$), 3.38(t,J=7.9Hz,2H,N—CH$_2$CH$_2$Ar), 2.95(m,5H,N—CH$_2$CH$_2$—ArCH$_3$SI$_2$NH), 2.8(s,3H,N—CH$_3$)

IR(KBr,cm$^{-1}$): 1240(CH$_3$O), 1160 and 1340(S=O)

MS: 409(M$^+$+1)

EXAMPLE 2

Production of 1-(4-imidazolephenoxy)-2-[N-(3,4-dimethoxyphenethyl)-N-methylamino]ethane (1) 4-(Imidazol-1-yl)phenol (5 g, 31.3 mmol), 1,2-dibromoethane (8.09 g, 93.9 mmol) and sodium hydroxide (1.25 g, 31.3 mmol) were refluxed in ethanol for 24 h. Thereafter, the solvent was evaporated and the residue was diluted with a saturated aqueous solution of sodium bicarbonate, followed by extraction with ethyl acetate. The extracted organic layer was washed twice with a saturated aqueous solution of sodium chloride and dried with magnesium sulfate, followed by evaporation of the solvent. The residue was purified by column chromatography on silica gel using, as an eluent, methylene chloride containing 30% ethyl acetate. The fractions containing the product were subjected to evaporation to yield the end compound 1-bromo-2-[4-(imidazol-1-yl)phenoxy]ethane (3.58 g) in a solid form.

$^1$H-NMR (CDCl$_3$): δ7.8(s,1H), 7.35(dd,2H), 7.2(t,2H), 7.0(dd,2H), 4.35(t,2H), 3.65(t,2H)

(2) A portion (1 g, 3.8 mmol) of the 1-bromo-2-(4-[imidazol-1-yl)phenoxy]ethane produced in (1) above, 2-(3, 4-dimethoxyphenyl)-N-methylethylamine (1.05 ml, 5.7 mmol), potassium iodide (1.81 g, 11.4 mmol) and sodium bicarbonate (0.94 g, 11.4 mmol) were heated in N,N-dimethylformamide (15 ml) at 80–90° C. for 24 h. Thereafter, the reaction mixture was diluted with water and subjected to extraction with ethyl acetate. The extracted organic layer was washed twice with a saturated aqueous solution of sodium chloride and dried with magnesium sulfate, followed by evaporation; the residue was purified by being subjected to column chromatography on silica gel using, as an eluent, chloroform containing methanol (5%). The fractions containing the product were combined and subjected to evaporation to yield the titled compound 1-[4-(imidazol-1-yl)phenoxy]-2-[N-(3,4-dimethoxyphenethyl)-N-methylaminolethane (1.1 g) in a solid form.

m.p.: 57–58° C.

$^1$H-NMR (CDCl$_3$): δ7.7(s,1H,imidazol H), 7.25(d,J= 8.8Hz,2H,ArH), 7.15(d,J=3.7Hz,2H,imidazol H), 6.9(d,J= 8.9Hz,2H,ArH), 6.7(m,3H,ArH), 4.0(t,J=5.5Hz,2H,CH$_2$O), 3.70(s,3H,OCH$_3$), 3.75(s,3H,OCH$_3$), 2.8(t,J=5.5Hz,2H, CH$_2$Ar), 2.71(m,4H,N—CH$_2$X2), 2.35(s,3H,N—CH$_3$)

IR(KBr,cm$^{-1}$): 1660(C=N)
MS: 382(M$^+$+1)

EXAMPLE 3
Production of 1-(4-methanesulfonamidophenoxy)-2-[N-(3,4-dichlorophenethyl)-N-methylamino]ethane hydrochloride (1) Lithium aluminum hydride (LAH) (0.57 g, 0.015 mol) were dissolved in tetrahydrofuran (30 ml) at room temperature, followed by stirring for 30 min. To the resulting solution there was slowly added dropwise a solution having 3,4-dichlorophenylacetic acid (3 g, 0.015 mol) and triethylamine (2.1 ml, 0.015 mol) dissolved in tetrahydrofuran (20 ml) and after stirring at the reflux temperature for 3 h, the mixture was cooled and water was poured into. The mixture was neutralized with an aqueous solution of sodium hydroxide and subjected to extraction with ethyl acetate to yield the end compound 3,4-dichlorophenethyl alcohol (2.53 g).

$^1$H-NMR (CDCl$_3$): δ7.36(m,2H), 7.1(dd,1H), 3.87(m, 2H), 2.84(m,2H)

(2) A portion (1 g, 5.23 mmol) of the 3,4-dichlorophenethyl alcohol produced in (1) above was dissolved in pyridine (10 ml) and methanesulfonyl chloride (0.61 ml, 7.85 mmol) was slowly added dropwise, followed by stirring at room temperature for 1 h and pouring into water. The mixture was subjected to extraction with ethyl acetate and concentrated under vacuum; the residue was dissolved in 50 ml of a solution of 40% methylamine in methanol and the solution was stirred overnight at room temperature, followed by concentration under vacuum. The residue was subjected to column chromatography using a 9:1 solvent system of chloroform and methanol as an eluent to yield the end compound 3,4-dichlorophenethyl-N-methylamine (0.76 g).

$^1$H-NMR (CDCl$_3$): δ7.16(m,2H), 6.89(dd,1H), 2.68-2.58 (m,4H), 2.29(s,3H)

(3) 2-(4-nitrophenoxy)ethyl bromide (0.5 g, 2.03 mmol) was dissolved in methanol (30 ml) and, after adding 10% Pd/C (0.2 g), the solution was stirred for 1 h in hydrogen gas, followed by filtration. The filtrate was concentrated under vacuum and the residue was dissolved in pyridine (20 ml). To the resulting solution, methanesulfonyl chloride (0.25 ml, 3.2 mmol) was slowly added dropwise, followed by stirring overnight. Water was poured into the reaction mixture, followed by extraction with ethyl acetate and concentration under vacuum. The residue was subjected to column chromatography using a 1:1 solvent system of ethyl acetate and hexane as an eluent to yield the end compound 2-(4-methanesulfonamidophenoxy)ethyl bromide (0.22 g).

$^1$H-NMR (CDCl$_3$): δ7.19(m,2H), 6.91(m,2H), 4.26(t,2H), 3.64(t,2H), 2.96(s,3H)

(4) A portion (0.2 g, 0.68 mmol) of the 2-(4-methanesulfonamidophenoxy)ethyl bromide produced in (3) above, 0.28 g (0.00136 mol) of the 3,4-dichlorophenethyl-N-methylamine produced in (2) above, potassium iodide (0.17 g, 1.02 mmol) and sodium bicarbonate (0.086 g, 1.02 mmol) were dissolved in N,N-dimethylformamide (20 ml) and the resulting solution was stirred for 3 h as it was heated at 85–90° C. in an oil bath. Water was poured into the reaction mixture and extraction was conducted with ethyl acetate, followed by drying with magnesium sulfate and concentration under vacuum. The residue was purified by being subjected to column chromatography using a 9:1 solvent system of chloroform and methanol as an eluent to yield the product (0.11 g). The product was redissolved in methanol (10 ml) and HCl gas was passed through the resulting solution to yield the titled compound 1-(4-methanesulfonamidophenoxy)-2-[N-(3,4-dichlorophenethyl)-N-methylamino]ethane hydrochloride (0.11 g) as a foam.

$^1$H-NMR (DMSO-d$_6$): δ7.46-7.39(m,2H,Ar—Cl$_2$H), 7.18-7.14(m,3H,2Ar—H+Ar—Cl$_2$H), 6.92(d,J=7Hz,2H, ArH), 4.29(t,J=5.1Hz,2H,—CH$_2$—O—Ar), 3.71-3.27(m, 4H,—CH$_2$—N—CH$_2$—), 3.04(t,J=9.1Hz,2H,Ar—CH$_2$—CH$_2$—N), 2.96(s,3H,SO$_2$CH$_3$), 2.8(s,3H,N—CH$_3$)

IR(KBr,cm$^{-1}$): 780(C—Cl)
MS: 417(M$^+$)

EXAMPLE 4
Production of 1-(3,4-dinitrophenoxy)-2-[N-(3,4-dimethoxyphenethyl)-N-methylamino]ethane hydrochloride (1) 2-(3,4-Dimethoxyphenyl)-N-methylethylamine (2.77 ml, 0.015 mol) and 2-bromoethanol (1.13 ml, 0.015 mol) were dissolved in N,N-dimethylformamide (10 ml). To the resulting solution, potassium iodide (2.45 g, 0.015 mol) was added, followed by stirring at 80° C. for 1.5 h. The reaction mixture was cooled to room temperature and, thereafter the solvent was evaporated under vacuum; after adding a saturated aqueous solution of sodium bicarbonate, three extractions were conducted with ethyl acetate. The organic layers were combined, dried with sodium sulfate and concentrated under vacuum. The residue was purified by being subjected to column chromatography on silica gel using a 9:1 solvent system of chloroform and methanol as an eluent and the fractions containing the end product were collected and the solvent was evaporated under vacuum, followed by drying to yield the end compound 2-[N-(3,4-dimethoxyphenethyl)-N-methylamino]ethanol (1.35 g) as an oil.

$^1$H-NMR (CDCl$_3$): δ6.80(d,1H), 6.72(m,2H), 3.87(s,3H), 3.85(s,3H), 3.57(m,2H), 2.70(m,4H), 2.58(t,2H), 2.33(s,3H)

(2) A portion (0.50 g, 2.1 mmol) of the 2-[N-(3,4-dimethoxyphenethyl)-N-methylamino]ethanol produced in (1) above was dissolved in dimethyl sulfoxide (6 ml) and 60% sodium hydride (0.12 g, 3 mmol) was added to the resulting solution. The reaction mixture was stirred at room temperature for 1 h and 1-chloro-3,4-dinitrobenzene (0.48 ml, 4 mmol) was added on a water bath. The mixture was stirred at room temperature for 2 h and after adding a saturated aqueous solution of sodium bicarbonate, three extractions were conducted with chloroform. The organic layers were combined, dried with sodium sulfate and concentrated under vacuum. The residue was purified by being subjected to column chromatography on silica gel using a 15:1 solvent system of chloroform and methanol as an eluent and the fractions containing the end compound were collected and the solvent was evaporated under vacuum, with the residue being recrystallized from ethanol to yield the titled compound 1-(3,4-dinitrophenoxy)-2-[N-(3,4-dimethoxyphenethyl)-N-methylamino]ethane hydrochloride (0.31 g).

m.p.: 186–188° C.

$^1$H-NMR (CDCl$_3$): δ7.81(d,J=8.7Hz, 1H,ArH), 7.08(s, 1H,ArH), 7.01(d,J=8.7Hz,1H,ArH), 6.74–6.77(m,3H,ArH), 4.17(t,J=5.7Hz,2H,OCH$_2$CH$_2$), 3.86(s,3H,OCH$_3$), 3.85(s, 3H, OCH$_3$), 2.93(t,J=5.7Hz,2H,OCH$_2$CH$_2$N), 2.74(s,4H, Ar—CH$_2$CH$_2$N), 2.43(s,3H,NCH$_3$)

IR(KBr,cm$^{-1}$): 1520, 1335(NO$_2$)
MS: 208(M$^+$–197), 197(M$^+$–208)

EXAMPLE 5
Production of 1-(2-chloro-4-methanesulfonamidophenoxy)-2-[N-(3,4-dimethoxophenethyl)-N-methylamino]ethane hydrochloride (1) Dibromoethane (14.9 ml, 0.1728 mol) and 2-chloro-4-nitrophenol (10 g, 0.0576 mol) were dissolved in dimethylfomamide (250 ml) and potassium carbonate (9.55 g) was added to the resulting solution, followed by stirring at 85° C. for 30 min. Thereafter, the reaction solution was diluted with water and subjected to three extractions with ethyl acetate. The organic extracts were combined, dried with magnesium and the solvent was evaporated; thereafter, the residue was purified by being subjected to column chromatography using a 1:1 solvent system of n-hexane and ethyl acetate as an eluent and the fractions containing the end product were collected and subjected to evaporation to yield the end compound 1-(2-chloro-4-nitrophenoxy)-2-bromoethane (14.0 g) as a yellow solid mass.

$^1$H-NMR (DMSO-d$_6$): δ8.30(s,1H), 8.21(d,1H), 7.42(d, 1H), 4.61(t,2H), 3.89(t,2H)

(2) 2-(3,4-Dimethoxyphenyl)-N-methylethylamine (18.4 ml, 0.0998 mol) and the 1-(2-chloro-4-nitrophenoxy)-2-bromoethane produced in (1) above in an amount of 14 g (0.0499 mol) were dissolved in a 1:2 solvent system of ethanol and acetonitrile and the resulting solution was heated at the reflux temperature for 15 h. Thereafter, the solvent was evaporated and the residue was diluted with water, followed by extraction with ethyl acetate. The aqueous layer was rendered basic at a pH of about 9 with an aqueous solution of sodium carbonate, followed by three extractions with ethyl acetate. The organic extracts were combined, dried with magnesium sulfate and the solvent was evaporated; thereafter, the residue was purified by being subjected to column chromatography on silica gel using, as an eluent, ethyl acetate containing methanol (5–10%). The fractions containing the end product were combined and the solvent was evaporated to yield the end compound 1-(2-chloro-4-nitrophenoxy)-2-[N-(3,4-dimethoxyphenethyl)-N-methylamino]ethane (15.7 g) as a yellow oil.

$^1$H-NMR (CDCl$_3$): δ8.28(d,1H), 8.14(m,1H), 6.97(d,1H), 6.78(m,3H), 4.23(t,2H), 3.86(s,3H), 3.85(s,3H), 2.99(t,2H), 2.78(s,4H), 2.48(s,3H)

(3) A portion (15.63 g, 0.040 mol) of the 1-(2-chloro-4-nitrophenoxy)-2-[N-(3,4-dimethoxyphenethyl)-N-methylamino]ethane produced in (2) above was dissolved in hot ethanol (500 ml) and, thereafter, a solution consisting of a mixture of Na$_2$S$_2$O$_4$ (27.56 g) and water (125 ml) was added to the resulting solution, thereby forming a precipitate. The mixture was heated at the reflux temperature for 20 min. Thereafter, the solvent was evaporated and the residue was diluted with water, followed by extraction with ethyl acetate. An aqueous solution of sodium carbonate was added to the aqueous layer such that it became basic up to a pH of about 9, followed by three extractions with ethyl acetate. The organic extracts were combined, dried with magnesium sulfate, and the solvent was evaporated; thereafter, the residue was purified by being subjected to column chromatography on silica gel using, as an eluent, ethyl acetate containing methanol (10%). The fractions containing the end compound were combined and the solvent was evaporated to yield the end compound 1-(4-amino-2-chlorophenoxy)-2-[N-(3,4-dimethoxyphenethyl)-N-methylamino]ethane (4.78 g) as a yellow oil.

$^1$H-NMR (CD$_3$OD): δ6.96(m,2H), 6.90(m,2H), 6.73(d, 1H), 4.20(m,2H), 3.91(s,3H), 3.89(s,3H), 3.03(m,2H), 2.90(s,4H), 2.58(s,3H)

(4) The 1-(4-amino-2-chlorophenoxy)-2-[N-(3,4-dimethoxyphenethyl)-N-methylamino]ethane produced in (3) above in an amount of 4.78 g (0.013 mol) was dissolved in pyridine (25 ml) and, thereafter, methanesulfonyl chloride (1.22 ml) was slowly added at room temperature. Thereafter, the reaction mixture was stirred at ordinary temperatures for about 16 h, followed by addition of ethanol and evaporation of the solvent pyridine; then, a 10% aqueous solution of sodium hydroxide was added to the residue and extraction was conducted with ethyl acetate. The organic layer was washed with water twice and, thereafter, the organic extracts were dried with magnesium sulfate, followed by evaporation of the solvent. The residue was purified by being subjected to column chromatography on silica gel using, as an eluent, ethyl acetate containing methanol (10%). The fractions containing the end product were combined and the solvent was evaporated to yield the end compound 1-(2-chloro-4-methanesulfonamidophenoxy)-2-[N-(3,4-dimethoxyphenethyl)-N-methylamino]ethane (3.5 g) as a pale yellow solid mass.

$^1$H-NMR (DMSO-d$_6$): δ9.56(s,1H), 7.26(s,1H), 7.14(s, 2H), 6.82(m,2H), 6.73(d,1H), 4.10(t,2H), 3.73(s,3H), 3.69 (s,3H), 2.94(s,3H), 2.81(t,2H), 2.65(s,4H), 2.34(s,3H)

(5) A portion (1.6 g, 3.6 mmol) of the 1-(2-chloro-4-methanesulfonamidophenoxy]-2-[N-(3,4-dimethoxyphenethyl)-N-methylamino]ethane produced in (4) above was dissolved in ethyl acetate (50 ml) and, thereafter, HCl was injected in a gaseous state (H$_2$SO$_4$+ NH$_4$Cl) into the resulting solution as it was stirred at ordinary temperatures, thereby forming a precipitate. When no more precipitate was formed, the solvent was evaporated to yield the titled compound 1-(2-chloro-4-methanesulfonamidophenoxy)-2-[N-(3,4-dimethoxyphenethyl)-N-methylamino]ethane hydrochloride (1.7 g) as a pale yellow solid mass.

m.p.: 81.4–83.2° C.

$^1$H-NMR (CDCl$_3$): δ8.57(s,1H,NHSO$_2$), 7.46(s,1H,ArH), 7.20(d,J=7.2Hz,1H,ArH), 6.79(s,4H,ArH), 4.65(brs,1H, CH$_2$CH$_3$O), 4.52(brs,1H,CH$_2$CH$_2$O), 3.87(s,3H,CH$_3$O), 3.86(s,3H,CH$_3$O), 3.07(s,3H,NHSO$_2$CH$_3$), 2.98(s,3H, CH$_2$NCH$_3$)

IR(KBr,cm$^{-1}$): 3450(NH), 1160(S=O)

MS: 443(M$^+$)

EXAMPLE 6

Production of 1-(2,4-dinitrophenoxy)-2-[N-3,4-dimethoxyphenethyl)-N-methylamino]ethane hydrochloride (1) Dibromoethane (5.25 g, 0.049 mol) and 2,4-dinitrophenol (3 g, 0.016 mol) were added to dimethylformamide (20 ml) and, after adding a fine powder of potassium carbonate (2.24 g), the mixture was heated at 85° C. for 1.5 h. Thereafter, the solvent was evaporated and three extractions were conducted with ethyl acetate. The organic extracts were combined and dried with sodium sulfate, with the residue being subjected to column chromatography on silica gel using methylene chloride as an eluent. The fractions containing the end product were collected and the solvent was evaporated to yield the end compound 2,4-dinitrophenoxyethly bromide (1.64 g).

$^1$H-NMR (CDCl$_3$): δ8.74(s,1H), 8.44(d,1H), 7.20(d,1H), 4.55(t,2H), 3.71(t,2H)

(2) 2-(3,4-Dimethoxyphenyl)-N-methylethylamine (0.31 g, 1.9 mmol) was added to dimethylformamide (10 ml) and, thereafter, sodium bicarbonate (0.4 g, 5.7 mmol), potassium iodide (0.53 g, 3.8 mmol) and a portion (0.7 g, 2.4 mmol) of the 2,4-dinitrophenoxyethyl bromide produced in (1) above were added, followed by stirring at 85° C. for 2 h; thereafter, the mixture was poured into water (50 ml) and subjected to three extractions with methylene chloride. The organic extracts were combined, dried with sodium sulfate and the solvent was evaporated, with the residue being thereafter purified by being subjected to column chromatography on silica gel using methylene chloride as an eluent. The fractions containing the end product were collected to yield the end compound 1-(2,4-dinitrophenoxy)-2-[N-(3,4-dimethoxyphenethyl)-N-methylamino]ethane (330 mg).

$^1$H-NMR (CDCl$_3$): δ8.72(s,1H), 8.38(d,1H), 7.17(d,1H), 6.76(m,3H), 4.27(t,2H), 3.86(s,3H), 3.84(s,3H), 2.94(t,2H), 2.73(s,4H), 2.43(s,3H)

(3) The 1-(2,4-dinitrophenoxy)-2-[N-(3,4-dimethoxyphenethyl)-N-methylamino]ethane produced in (2) above in an amount of 330 mg (0.8 mmol) was added to ethyl acetate (5 ml) and, thereafter, HCl gas passed through the mixture as it was stirred at room temperature. The resulting precipitate was filtered and dried to yield the titled compound 1-(2,4-dinitrophenoxy)-2-[N-(3,4-dimethoxyphenethyl)-N-methylamino]ethane hydrochloride (312 mg).

m.p.>182° C. (with decomposition)

$^1$H-NMR (DMSO-$d_6$): δ10.99(bs,1H,N$^+$H), 8.79(s,1H, ArH), 8.56(d,J=9.3Hz,1H,ArH), 7.65(d,J=9.3Hz,1H,ArH), 6.89(m,2H,ArH), 6.80(d,J=8.2Hz,1H,ArH), 4.80(bs,2H, CH$_2$CH$_2$O), 3.76(s,3H,OCH$_3$), 3.73(s,3H,OCH$_3$), 3.64(bs, 2H,NCH$_2$CH$_2$O), 3.20–3.45(m,2H,Ar—CH$_2$CH$_2$N), 3.00(t, J=8.2Hz,2H,Ar—CH$_2$CH$_2$—N), 2.91(s,3H,NCH$_3$)

IR(KBr,cm$^{-1}$): 1520, 1350(NO$_2$)

MS: 405(M$^+$)

EXAMPLE 7

Production of 1-(2-chloro-4-methanesulfonamidophenoxy)-2-[N-(2-amino-4,5-dimethoxyphenethyl)-N-methylamino] ethane hydrochloride (1) 3,4-Dimethoxyphenylacetic acid (3 g, 0.0153 mol) was dissolved in methanol (50 ml) and, thereafter, conc. sulfuric acid (0.05 ml) was added to the resulting solution, followed by heating at the reflux temperature for 2 h. Thereafter, the solvent was evaporated and the residue was neutralized with an aqueous solution of sodium bicarbonate, followed by extraction with ethyl acetate. The organic extract was dried with sodium sulfate, followed by evaporation of the solvent and drying under vacuum to yield the oil compound methyl 3,4-dimethoxyphenylacetate (3.2 g) as a colorless oil.

$^1$H-NMR (CDCl$_3$): δ6.82(s,3H), 3.88(s,3H), 3.87(s,3H), 3.70(s,3H), 3.57(s,2H)

(2) The methyl 3,4-dimethoxyphenylacetate produced in (1) above in an amount of 3.2 g (0.015 mol) was dissolved in acetic anhydride (50 ml) and acetic acid (5 ml) and, thereafter, the resulting solution was cooled at −20° C. To the solution, 86% nitric acid (1.49 ml, 0.030 mol) as dissolved in acetic acid (20 ml) was added dropwise over 1 h and, thereafter, the reaction solution was stirred over an additional 1 h until its temperature reached 15° C. After adding methanol (70 ml) to the reaction mixture, the latter was stirred for 1 h to evaporate the solvent. The residue was neutralized with an aqueous solution of 2N NaOH and, thereafter, two extractions were conducted with ethyl acetate. The organic residue was dried with sodium sulfate, followed by evaporation of the solvent; the resulting solids were washed with water and ether, followed by drying to yield the end compound methyl 2-nitro-4,5-dimethoxyphenylacetate (3.5 g) as a pale yellow solid mass.

m.p.: 110–111° C.

$^1$H-NMR (CDCl$_3$): δ7.75(s,1H), 6.73(s,1H), 3.99(s,2H), 3.98(s,3H), 3.96(s,3H), 3.73(s,3H)

(3) A portion (3.4 g, 0.013 mol) of the methyl 2-nitro-4,5-dimethoxyphenylacetate produced in (2) above and sodium borohydride (2.52 g, 0.067 mol) were dissolved in tetrahydrofuran (100 ml), followed by heating at the reflux temperature for 30 min. Methanol (10 ml) was added dropwise to the reaction mixture over 30 min, followed by heating for 1 h. The mixture was cooled to room temperature and the residual reagents were decomposed with an aqueous solution of 1N HCl, followed by neutralization with an aqueous solution of sodium bicarbonate and three extractions with ethyl acetate. The organic extracts were dried with sodium sulfate and the solvent was evaporated, with the residue being purified by being subjected to column chromatography on silica gel using, as an eluent, ethyl acetate containing n-hexane (33%). The fractions containing the end product were collected and the solvent was evaporated to yield the end compound 2-nitro-4,5-dimethoxyphenethyl alcohol (3.0 g) as a pale yellow solid mass.

m.p.: 103–105° C.

$^1$H-NMR (CDCl$_3$): δ7.61(s,1H), 6.81(s,1H), 3.94–3.97 (m,8H), 3.21(t,J=6.4Hz,2H)

(4) The 2-nitro-4,5-dimethoxyphenethyl alcohol produced in (3) above in an amount of 3.0 g (0.013 mol) was dissolved in pyridine (15 ml), followed by cooling to 0° C. and addition of methanesulfonyl chloride (2.05 ml, 0.026 mol). The reaction mixture was stirred at room temperature for 1 h and the solvent was evaporated, followed by dilution with an aqueous solution of sodium bicarbonate and extraction with ethyl acetate. The organic extract was dried with sodium sulfate and the solvent was evaporated, followed by drying under vacuum to yield the end compound 2-nitro-4,5-dimethoxyphenethyl methanesulfonate (2.6 g) as a yellow solid mass.

$^1$H-NMR (CDCl$_3$): δ7.73(s,1H), 6.89(s,1H), 4.56(t,J=6.4Hz,2H), 3.99(s,3H), 3.95(s,3H), 3.39(t,J=6.4Hz,2H), 2.97(s,3H)

(5) The 2-nitro-4,5-dimethoxyphenethyl methanesulfonate produced in (4) above in an amount of 2.6 g (8.52 mmol) was dissolved in 40 ml of a methanol solution of 40% methylamine and the solution was heated at 50° C. and stirred for 1 h, followed by restirring at room temperature for 12 h. Thereafter, the solvent was evaporated and the residue was diluted with an aqueous solution of sodium bicarbonate, followed by extraction with methylene chloride. The solvent was evaporated and the residue was rendered acidic with 3N HCl, followed by extraction with ethyl acetate. The aqueous layers were collected and rendered basic with an aqueous solution of 2N NaOH, followed by two extractions with chloroform. The organic layers were collected and dried with sodium sulfate, followed by evaporation under vacuum to yield the end compound 2-(2-nitro-4,5-dimethoxyphenyl)-N-methylethylamine (1.35 g) as a brown caramel-like substance.

$^1$H-NMR (CDCl$_3$): δ7.62(s,1H), 6.78(s,1H), 3.97(s,3H), 3.93(s,3H), 3.14(t,J=7.2Hz,2H), 2.89(t,J=7.3Hz,2H), 2.48(s, 3H)

(6) To 11 g (0.040 mol) of the 1-(2-chloro-4-nitrophenoxy)-2-bromoethane produced in Example 5-(1), ethanol (170 ml) was added and dissolved therein; to the resulting solution, Na$_2$S$_2$O$_4$ (27.6 g, 0.158 mol) as dissolved in water (50 ml) was added dropwise, followed by stirring at room temperature for 20 min. The solvent was evaporated and the residue was diluted with an aqueous solution of sodium bicarbonate and two extractions were conducted with ethyl acetate. The organic extracts were dried with sodium sulfate and the solvent was evaporated, with the residue being purified by being subjected to column chromatography on silica gel using, as an eluent, n-hexane containing ethyl acetate (25%) to yield the end compound 1-(4-amino-2-chlorophenoxy)-2-bromoethane (2.35 g) as a pale yellow solid mass.

$^1$H-NMR (CDCl$_3$): δ6.83(d,J=8.7Hz,1H), 6.73(d,J=2.8Hz,1H), 6.53(dd,J=2.7Hz,8.6Hz,1H), 4.25(t,J=6.5Hz, 2H), 3.62(t,J=6.5Hz,2H)

(7) A portion (2.3 g, 9.18 mmol) of the 1-(4-amino-2-chlorophenoxy)-2-bromoethane produced in (6) above was dissolved in pyridine (10 ml) and the resulting solution was cooled to 0° C., followed by dripping of methanesulfonyl chloride (1.43 ml, 0.018 mol) and stirring at room temperature for 2 h. Thereafter, the solvent was evaporated and the residue was diluted with an aqueous solution of sodium bicarbonate, followed by extraction with chloroform. The extract was dried with sodium sulfate and the solvent was evaporated, with the residue being thereafter purified by being subjected to column chromatography on silica gel using, as an eluent, chloroform containing methanol (6.6%) to yield the end compound 1-(2-chloro-4-methanesulfonamidophenoxy)-2-bromoethane (2.78 g) as a pale yellow solid mass.

m.p.: 96–98° C.

$^1$H-NMR (CDCl$_3$): δ7.33(d,J=2.6Hz,1H), 7.16(dd,J=2.6Hz,8.8Hz,1H), 6.92(d,J=8.8Hz,1H), 6.57(brs,1H), 4.34(t, J=6.4Hz,2H), 3.67(t,J=6.4Hz,2H), 3.00(s,3H)

(8) The 2-(2-nitro-4,5-dimethoxyphenyl)-N-methylethylamine produced in (5) above in an amount of 1.35 g (5.62 mmol) and 923 mg (2.81 mmol) of the 1-(2-chloro-4-methanesulfonamidophenoxy)-2-bromoethane produced in (7) above were dissolved in a solvent system consisting of a mixture of acetonitrile (30 ml) and ethanol (15 ml) and the resulting solution was heated at the reflux temperature for 12 h. Thereafter, the solvent was evaporated and the residue was diluted with an aqueous solution of sodium bicarbonate, followed by extraction with chloroform. The organic extract was dried with sodium sulfate and the solvent was evaporated, with the residue being thereafter purified by being subjected to column chromatography on silica gel using, as an eluent, ethyl acetate containing methanol (6.6%) to yield the end compound 1-(2-chloro-4-methanesulfonamidophenoxy)-2-[N-(2-nitro-4,5-dimethoxyphenethyl)-N-methylamino]ethane (830 mg) as a brown caramel-like substance.

$^1$H-NMR (CDCl$_3$): δ7.58(s,1H), 7.29(d,J=2.6Hz,1H), 7.12(dd,J=2.6Hz,8.7Hz,1H), 6.86(d,J=8.8Hz,1H), 6.79(s,1H), 4.09(t,J=5.6Hz,2H), 3.94(s,3H), 3.92(s,3H), 3.13–3.16(m,2H), 2.99(s,3H), 2.96–2.98(m,2H), 2.83–2.86(m,2H), 2.51(s,3H)

(9) A portion (700 mg, 1.44 mmol) of the 1-(2-chloro-4-methanesulfonamidophenoxy)-2-[N-(2-nitro-4,5-dimethoxyphenethyl)-N-methylamino]ethane produced in (8) above was dissolved in ethanol (50 ml) and, thereafter, Na$_2$S$_2$O$_4$ (1.0 g, 5.74 mmol) as dissolved in water (15 ml) was added dropwise and the mixture was stirred at room temperature for 15 min. Thereafter, the solvent was evaporated and the residue was diluted with an aqueous solution of sodium bicarbonate and the solvent was evaporated, with the residue being thereafter purified by being subjected to column chromatography on silica gel using, as an eluent, chloroform containing methanol (25%). The resulting product was dissolved in methanol (5 ml) and, thereafter, the HCl gas as generated by adding conc. sulfuric acid to ammonium chloride was passed through the solution to thereby form a hydrochloride and hence yield the titled compound 1-(2-chloro-4-methanesulfonamidophenoxy)-2-[N-(2-amino-4,5-dimethoxyphenethyl)-N-methylamino]ethane hydrochloride (31 mg) as a pale yellow foam.

$^1$H-NMR (DMSO-d$_6$): δ10.37(brs,3H), 9.73(s,1H, NHSO$_2$), 7.32(d,J=2.0Hz,1H,ArH), 7.27(d,J=8.9Hz,1H, ArH), 7.21(d,J=8.8Hz,1H,ArH), 7.06(s,1H,ArH), 7.02(s,1H, ArH), 4.52(brs,2H,—CH$_2$O), 3.77(s,3H,CH$_3$O), 3.75(s,3H, CH$_3$O), 3.67(br s,2H), 3.52(br s,2H), 3.11–3.17(m,2H), 3.01 (s,3H,CH$_3$SO$_2$), 2.96(s,3H,NCH$_3$)

IR(KBr,cm$^{-1}$): 3440(NH$_2$), 1160(SO$_2$)

MS: 458(M$^+$)

EXAMPLE 8

Production of 1-(4-methanesulfonamido-2-(1H-pyrrolyl-1-yl)phenoxy)-2-[N-(3,4-dimethoxyphenethyl)-N-methylamino]ethane hydrochloride (1) 2-Amino-4-nitrophenol (5 g, 0.032 mol) and 2,5-dimethoxytetrahydrofuran (5.03 ml, 0.034 mol) were dissolved in glacial acetic acid (100 ml), followed by stirring at the reflux temperature for 10 min. Thereafter, the reaction solution was cooled to ordinary temperatures and neutralized with sodium carbonate, followed by dilution with water and three extractions with ethyl acetate. The organic extracts were combined, dried with magnesium sulfate and the solvent was evaporated, with the residue being thereafter purified by being subjected to column chromatography on silica gel suing a 2:1 solvent system of n-hexane and ethyl acetate. The fractions containing the end product were combined and the solvent was evaporated to yield the end compound 4-nitro-2-(1H-pyrrolyl-1-yl)phenol (3.81 g) as a yellow solid mass.

$^1$H-NMR (CDCl$_3$): δ8.15(m,2H), 7.13(d,1H), 6.92(dd, 2H), 6.42(dd,2H)

(2) The 4-nitro-2-(1H-pyrrol-1-yl)phenol produced in (1) above in an amount of 3.81 g (0.019 mol) and 1,2-dibromoethane (4.83 ml, 0.056 mol) were dissolved in N,N-dimethylformamide (70 ml) and, after adding sodium carbonate (3.1 g), stirring was done at 70° C. for 1 h. Thereafter, the reaction solution was diluted with water and rendered basic at a pH of about 9 with an aqueous solution of 10% sodium hydroxide, followed by three extractions with ethyl acetate. The organic extracts were combined, dried with magnesium sulfate and the solvent was evaporated, with the residue being thereafter purified by being subjected to column chromatography on silica gel using a 3:1 solvent system of n-hexane and ethyl acetate as an eluent. The fractions containing the end product were combined to yield the end compound 1-[4-nitro-2-(1H-pyrrol-1-yl)phenoxy]-2-bromoethane (1.7 g) as a yellow solid mass.

$^1$H-NMR (CDCl$_3$): δ8.18(m,2H), 7.13(m,3H), 6.36(dd, 2H), 4.45(t,J=5.8Hz,2H), 3.67(t,J=5.8Hz,2H)

(3) 3,4-Dimethoxy-N-methylethylamine (0.852 ml, 4.6 mmol) and 0.72 g (2.3 mmol) of the 1-[4-nitro-2-(1H-pyrrol-1-yl)phenoxy]-2-bromoethane produced in (2) above were dissolved in a 1:2 solvent system of ethanol and acetonitrile, followed by heating at the reflux temperature for 15 h. Thereafter, the solvent was evaporated and the residue was diluted with water, followed by extraction with ethyl acetate. The aqueous layer was rendered basic at a pH of about 9 with an aqueous solution of sodium carbonate, followed by three extractions with ethyl acetate. The organic extracts were combined, dried with magnesium sulfate and the solvent was evaporated, with the residue being purified by being subjected to column chromatography on silica gel using, as an eluent, ethyl acetate containing methanol (10%). The fractions containing the end product were combined and the solvent was evaporated to yield the end compound 1-[4-nitro-2-(1H-pyrrol-1-yl)phenoxy]-2-[N-(3,4-dimethoxyphenethyl)-N-methylamino]ethane (0.72 g) as a yellow oil.

$^1$H-NMR (CDCl$_3$): δ8.18(m,2H), 7.08(m,3H), 6.72(m, 3H), 6.32(dd,2H), 4.19(t,J=5.8Hz,2H), 3.87(s,3H), 3.85(s, 3H), 2.88(t,J=5.8Hz,2H), 2.69(m,4H), 2.37(s,3H)

(4) A portion (0.53 g, 1.25 mmol) of the 1-[4-nitro-2-(1H-pyrrol-1-yl)phenoxy]-2-[N-(3,4-dimethoxyphenethyl)-N-methylamino]ethane produced in (3) above was dissolved in 50 ml of a 1:1 solvent system of ethyl acetate and methanol and 10% Pd/C (0.15 g) was slowly added to the solution, which was thereafter stirred at ordinary temperatures for 10 min as hydrogen gas was injected. Thereafter, the reaction mixture was filtered through Celite and the filtrate was evaporated, with the residue being purified by being subjected to column chromatography on silica gel using, as an eluent, ethyl acetate containing methanol (10%). The fractions containing the end product were combined and the solvent was evaporated to yield the end compound 1-[4-amino-2-(1H-pyrrol-1-yl)phenoxy]-2-[N-(3,4-dimethoxyphenethyl)-N-methylamino]ethane (0.49 g) as a yellow oil.

$^1$H-NMR (CDCl$_3$): δ7.01(dd,2H), 6.86(d,1H), 6.70(m, 4H), 6.58(d,1H), 6.25(dd,2H), 3.87(s,3H), 3.85(s,3H), 3.49 (m,2H), 2.69(m,6H), 2.33(s,3H)

(5) The 1-4-[amino-2-(1H-pyrrol-1-yl)phenoxy]-2-[N-(3, 4-dimethoxyphenethyl)-N-methylamino]ethane as produced in (4) above in an amount of 0.5 g (1.27 mmol) was dissolved in pyridine (20 ml) and methanesulfonyl chloride (0.12 ml) was slowly added at 0° C. Thereafter, the reaction mixture was stirred at ordinary temperatures for 5 h and, thereafter, ethanol was added and pyridine was evaporated, with an aqueous solution of 10% sodium hydroxide being added to the residue to render it basic at a pH of about 10, followed by extraction with ethyl acetate. The organic layer was washed with water twice and dried with magnesium sulfate, followed by evaporation, with the residue being purified by being subjected to column chromatography on silica gel using a 15:1 solvent system of methanol and chloroform as an eluent. The fractions containing the end product were combined and the solvent was evaporated to yield the end compound 1-[4-methanesulfonamido-2-(1H-pyrrol-1-yl)phenoxy]-2-[N-(3,4-dimethoxyphenethyl)-N-methylamino]ethane (0.4 g) as a yellow oil.

$^1$H-NMR (CDCl$_3$): δ7.20(d,1H), 7.12(m,1H), 7.04(dd, 2H), 7.00(s,1H), 6.77(m,1H), 6.70(m,2H), 6.28(m,2H), 4.05 (t,J=5.9Hz,2H), 3.87(s,3H), 3.85(s,3H), 3.00(s,3H), 2.82(t, J=5.9Hz,2H), 2.67(m,4H), 2.35(s,3H)

(6) The 1-[4-methanesulfonamido-2-(1H-pyrrol-1-yl) phenoxy]-2-[N-3,4-dimethoxyphenethyl)-N-methylamino] ethane produced in (5) above in an amount of 0.4 g (0.85 mmol) was dissolved in ethyl acetate (20 ml) and, thereafter, HCl was injected in a gaseous state (sulfuric acid+ ammonium chloride) with stirring, thereby forming a precipitate. When no more precipitate was formed, the solvent was evaporated to yield the titled compound 1-[4-(methanesulfonamido-2-(1H-pyrrol-1-yl)phenoxy]-2-[N-(3, 4-dimethoxyphenethyl)-N-methylamino]ethane hydrochloride (0.45 g) as a pale yellow solid mass.

m.p.: 88.6° C. (with decomposition)

$^1$H-NMR (CDCl$_3$): δ8.61(s,1H,NHSO$_2$CH$_3$), 7.40(s,1H, ArH), 7.28(d,J=9.4Hz,1H,ArH), 6.95(d,J=8.5Hz,1H,ArH), 6.81(m,5H,ArH+pyrrole), 6.22(s,2H,ArH), 4.52(br d, 2H,NCH$_2$CH$_2$O), 3.88(s,3H,OCH$_3$), 3.86(s,3H,OCH$_3$), 3.58 (br,1H,NCHCH$_2$O), 3.25(br,2H,CH$_2$NCH$_3$), 3.11(m,3H, CH$_2$CH$_2$NCH$_3$+NCHCH$_2$O), 3.02(s,3H,NHSO$_2$CH$_3$), 2.73 (s,3H,CH$_2$NCH$_3$)

IR(KBr,cm$^{-1}$): 3150(NH), 1340 and 1180(S=O)

MS: 474(M$^+$+1)

EXAMPLE 9

Production of 1-(2-acetamido-4-methanesulfonamidophenoxy)-2-[N-(3,4-dimethoxyphenethyl)-N-methylamino]ethane hydrochloride (1) 2-Amino-4-nitrophenol (10 g, 0.065 mol) was dissolved in tetrahydrofuran (100 ml) and, after cooling to 0° C., acetic anhydride (12.24 ml, 0.130 mol) was added dropwise, followed by stirring at room temperature for 2 h. Thereafter, methanol (10 ml) was added to the reaction mixture, which was then stirred at room temperature for 30 min and, thereafter, the solvent was evaporated and the resulting residue was diluted with diethyl ether and filtered. The solvent was evaporated off the filtrate and the resulting solids were dried to yield the end compound 2-acetamido-4-nitrophenol (12.21 g) as a pale brown solid mass.

$^1$H-NMR (DMSO-d$_6$): δ9.46(s,1H), 8.93(d,J=2.8Hz,1H), 7.89(dd,J=2.9Hz,8.9Hz,1H), 7.02(d,J=8.9Hz,1H), 2.14(s, 3H)

(2) A portion (9.6 g, 0.049 mol) of the 2-acetamido-4-nitrophenol produced in (1) above and potassium carbonate (33.86 g, 0.245 mol) were dissolved in dimethylformamide (100 ml), followed by heating at 70° C., addition of dibromoethane (21 ml, 0.245 mol) and stirring for 20 min. Thereafter, the reaction solution was filtered to remove the insoluble matter and the solvent was evaporated, with the residue being thereafter diluted with sodium bicarbonate and subjected to two extractions with ethyl acetate. The organic extracts were dried with sodium sulfate and the solvent was evaporated, with the resulting residue being purified by being subjected to column chromatography on silica gel using, as an eluent, ethyl acetate containing n-hexane (50%) to yield the end compound 1-(2-acetamido-4-nitrophenoxy)-2-bromoethane (8.2 g) as a pale yellow solid mass.

$^1$H-NMR (CDCl$_3$): δ9.32(d,J=2.7Hz,1H), 7.98(dd,J= 2.7Hz,9.0Hz,1H), 7.89(br s,1H), 6.93(d,J=9.0Hz,1H), 4.47 (t,J=5.6Hz,2H), 3.76(t,J=5.6Hz,2H), 2.26(s,3H)

(3) A portion (440 mg, 1.46 mmol) of the 1-(2-acetamido-4-nitrophenoxy)-2-bromoethane produced in (2) above was dissolved in dimethylformamide (5 ml) and, thereafter, potassium iodide (267 mg, 1.608 mmol) and 2-(3,4-dimethoxyphenyl)-N-methylethylamine (0.81 ml, 4.36 mmol) were added to the solution, which was stirred at 70° C. for 1.5 h. Thereafter, the solvent was evaporated from the reaction mixture and the residue was subjected to extraction with ethyl acetate. The organic layer was washed with water four times and dried with sodium sulfate, followed by evaporation of the solvent, with the resulting residue being purified by being subjected to column chromatography on silica gel using, as an eluent, chloroform containing methanol (6%) to yield the end compound 1-(2-acetamido-4-nitrophenoxy)-2-[N-(3,4-dimethoxyphenethyl)-N-methylamino]ethane (590 ml) as a yellow caramel-like substance.

$^1$H-NMR (CDCl$_3$): δ9.25(d,J=2.3Hz,1H), 8.54(s,1H), 7.93(dd,J=2.7Hz,9.0Hz,1H), 6.95(d,J=9.0Hz,1H), 6.72–6.82(m,3H), 4.23(t,J=5.4Hz,2H), 3.85(s,6H), 2.94(t,J= 5.4Hz,2H), 2.78(s,4H), 2.45(s,3H), 2.15(s,3H)

(4) The 1-(2-acetamido-4-nitrophenoxy)-2-[N-(3,4-dimethoxyphenethyl)-N-methylamino]ethane produced in (3) above in an amount of 590 mg (1.41 mmol) was dissolved in ethyl acetate (15 ml) and, thereafter, 10% Pd/C (100 mg) and methanol (15 ml) were added to the solution, which was stirred at room temperature for 12 h in a hydrogen gas. Thereafter, the reaction solution was filtered through Celite and the resulting organic layer was evaporated, thereafter dried to yield the end compound 1-(2-acetamido-4-aminophenoxy)-2-[N-(3,4-dimethoxyphenethyl)-N-methylamino]ethane (530 mg) as a brown foam.

$^1$H-NMR (CDCl$_3$): δ9.11(s,1H), 7.77(d,J=2.9Hz,1H), 6.70–6.81(m,4H), 6.33(d,J=8.5Hz,1H), 4.04(t,J=5.2Hz,2H), 3.85(s,6H), 2.71–2.76(m,6H), 2.44(s,3H), 2.07(s,3H)

(5) A portion (510 mg, 1.32 mmol) of the 1-(2-acetamido-4-aminophenoxy)-2-[N-(3,4-dimethoxyphenethyl)-N-methylamino]ethane produced in (4) above was dissolved in pyridine (5 ml) and, thereafter, the solution was cooled to 0° C. and methanesulfonyl chloride (0.21 ml, 2.63 mmol) was added, followed by stirring at room temperature for 2 h. Thereafter, the solvent was evaporated from the reaction mixture and the resulting residue was diluted with an aqueous solution of sodium bicarbonate, followed by extraction with chloroform. The organic layer was dried with sodium sulfate and the solvent was evaporated, with the resulting residue being purified by being subjected to column chromatography on silica gel using, as an eluent, chloroform containing methanol (6%). The resulting product was dissolved in methanol (10 ml) and the HCl as generated by adding conc. sulfuric acid to ammonium chloride was passed through the resulting solution. Thereafter, the solvent was evaporated for drying to yield the titled compound 1-(2-acetamido-4-methanesulfonamidophenoxy)-2-[N-(3,4-dimethoxyphenethyl)-N-methylamino]ethane hydrochloride (420 mg) as a foamy substance of ivory color.

$^1$H-NMR (DMSO-$d_6$): δ9.60(br s,1H,NH), 9.44(s,1H,—NH—CO—), 8.32(s,1H,—NHSO$_2$—), 7.93(s,1H,ArH), 7.05(d,J=8.5Hz,1H,ArH), 6.89–6.96(m,3H,ArH), 6.80(d,J=8.2Hz,1H,ArH), 4.36(br s, 2H,—CH$_2$O—), 3.74(s,3H, CH$_3$O—), 3.72(s,3H,CH$_3$—O—), 3.17(s,3H,—SO$_2$CH$_3$), 3.04–3.06(m,2H), 2.90(s,7H), 2.09(s,3H,CH$_3$CO—)

IR(KBr,cm$^{-1}$): 1690(—NCO—), 1155(SO$_2$)

MS: 466(M$^+$)

EXAMPLE 10

Production of 1-(2-amino-4-methanesulfonamidophenoxy)-2-[N-(3,4-dimethoxyphenethyl)-N-methylamino]ethane hydrochloride 1-(2-Acetamido-4-methanesulfonamidophenoxy)-2-[N-(3,4-dimethoxyphenethyl)-N-methylamino]ethane (1 g, 2.2 mmol) was heated in 3N HCl (10 ml) at the reflux temperature for 3 h. Thereafter, the reaction mixture was neutralized to a pH of 6–7 with a solution of 10% sodium hydroxide, followed by extraction with ethyl acetate; the organic extract was then dried with magnesium sulfate and the solvent was evaporated. The residue was subjected to column chromatography on silica gel using, as an eluent, chloroform containing methanol (5%–10%) to yield the titled compound 1-(2-amino-4-methanesulfonamidophenoxy)-2-[N-(3,4-dimethoxyphenethyl)-N-methylamino]ethane hydrochloride (0.79 g).

m.p.: 226–228° C.

$^1$H-NMR (CD$_3$OD): δ7.35(d,J=2.2Hz,1H,ArH), 7.2–7.8 (m,2H,ArH), 6.9(d,J=1.6Hz,1H,ArH), 6.8-6.7(m,2H,ArH), 4.45(t,2H,J=4.5Hz,CH$_2$—O), 3.74(s,3H,OCH$_3$), 3.71(s,3H, OCH$_3$), 3.41(s,2H,N—CH$_2$), 3.06(t,J=8.5Hz,2H,Ar—CH$_2$), 2.93(s,3H,N—CH$_3$), 2.87(s,3H,SO$_2$CH$_3$)

IR(KBr,cm$^{-1}$): 1160, 1340(S=O)

MS: 424(M$^+$+1)

EXAMPLE 11

Production of 1-(2-bromo-4-methanesulfonamidophenoxy)-2-[N-(3,4-dimethoxyphenethyl)-N-methylamino]ethane hydrochloride (1) 4-Nitrophenol (5 g, 35.9 mmol) was added to acetic acid (20 ml) and to the mixture, there was slowly added a solution of a mixture of bromine (0.93 ml, 18 mmol) and acetic acid (5 ml) at 85° C. The reaction mixture was stirred at the same temperature for 5 h and, thereafter, it was added to water and subjected to extraction with ethyl acetate. The organic extract was concentrated and the residue was subjected to column chromatography using a 7:3:1 solvent system of cyclohexane, ethyl acetate and methanol as an eluent to yield the end compound 2-bromo-4-nitrophenol (6.7 g).

$^1$H-NMR (CDCl$_3$): δ8.44(s,1H), 8.17(d,1H), 7.12(d,1H)

(2) A portion (2.3 g, 10.6 mmol) of the 2-bromo-4-nitrophenol produced in (1) above and 1,2-dibromoethane (7.9 g, 42.1 mmol) were added to N,N-dimethylformamide (20 ml); to the mixture, potassium carbonate (1.6 g) was added, followed by stirring at 80–85° C. for 3 h. The reaction mixture was added to water (100 ml) and extraction was conducted with ethyl acetate, followed by the drying of the extract with magnesium sulfate and concentration. The residue was subjected to column chromatography using a 10:3:1 solvent system of n-hexane, ethyl ether and ethyl acetate as an eluent to yield the end compound 1-(2-bromo-4-nitrophenoxy-2-bromoethane (2.14 g).

$^1$H-NMR (CDCl$_3$): δ8.47(s,1H), 8.21(d,1H), 6.96(d,1), 4.42(m,2H), 3.71(m,2H)

(3) A portion (1.19 g, 3.66 mmol) of the 1-(2-bromo-2-nitrophenoxy)-2-bromoethane produced in (2) above and 2-(3,4-dimethoxyphenyl)-N-methylethylamine (1.35 ml, 7.32 mmol) were added to 20 ml of a 2:1 solvent system of acetonitrile and ethanol and refluxed for 8 h, followed by concentration. The mixture was neutralized with an aqueous solution of sodium bicarbonate and subjected to extraction with ethyl acetate; the extract was dried with magnesium sulfate and thereafter concentrated. The residue was subjected to column chromatography using a 9:1 solvent system of chloroform and methanol as an eluent to yield the end compound 1-(2-bromo-4-nitrophenoxy)-2-[N-(3,4-dimethoxyphenethyl)-N-methylamino]ethane (1.5 g).

$^1$H-NMR (CDCl$_3$): δ8.47(s,1H), 8.19(dd,J=2.7Hz,1H), 6.8(d,1H), 6.74(m,3H), 4.19(m,2H), 3.86(s,3H), 3.84(s,3H), 2.99(m,2H), 2.77(s,4H), 2.58(s,3H)

(4) A portion (1.25 g. 2.73 mmol) of the 1-(2-bromo-4-nitrophenoxy)-2-[N-(3,4-dimethoxyphenethyl)-N-methylamino]ethane produced in (3) above was slowly added to cooled conc. hydrochloric acid (50 ml), followed by adding of tin(II) chloride (2.1 g), stirring at 50° C. for 1 h and subsequent cooling. The reaction mixture was added to ice water and neutralized with an aqueous solution of potassium carbonate, followed by extraction with chloroform and drying with magnesium sulfate; subsequent concentration gave the end compound 1-(2-bromo-4-aminophenoxy)-2-[N-(3,4-dimethoxyphenethyl)-N-methylamino]ethane (1 g).

(5) The 1-(2-bromo-4-aminophenoxy)-2-[N-(3,4-dimethoxyphenethyl)-N-methylamino]ethane as produced in (4) above in an amount of 1.1 g (2.69 mmol) was dissolved in pyridine (15 ml) and to the solution, there was slowly added methanesulfonyl chloride (0.62 ml). The reaction mixture was stirred at room temperature for 1 h and, thereafter, it was added to water and subjected to extraction with ethyl acetate. The extract was dried with magnesium sulfate and concentrated, with the residue being thereafter treated using a 7:3:1 solvent system of chloroform, ethyl acetate and methanol as an eluent to yield an oily substance (0.56 g). The product was dissolved in methanol (20 ml), cooled to 0° C. and stirred for 20 min after addition of a solution (2.3 ml) of 1M HCl in ethyl ether. The mixture was concentrated at room temperature under vacuum to yield 1-(2-bromo-4-methanesulfonamidophenoxy)-2-[N-(3,4-dimethoxyphenethyl)-N-methylamino]ethane hydrochloride (0.57 g).

m.p.: 59–65° C. (foam)

$^1$H-NMR (CD$_3$OD): δ7.53(s,1H,ArH), 7.29(d,1H,J=2.6Hz,ArH), 7.15(d,1H,J=8.9Hz,ArH), 6.94(m,3H,ArH), 4.47(t,J=4.8Hz,2H,OCH$_2$), 3.84(s,3H,OCH$_3$), 3.82(s,3H, OCH$_2$), 3.76(t,2H,N(CH$_3$)—CH$_2$CH$_2$O), 3.6(t,2H, ArCH$_2$CH$_2$), 3.13(m,5H,CH$_3$SO$_2$NH,ArCH$_2$), 2.92(s,3H, NCH$_3$)

IR(KBr,cm$^{-1}$): 1160, 1330(S=O), 3420(NH)

MS: 489(M$^+$+2)

EXAMPLE 12

Production of 1-[2-(N,N-dimethylamino)-4-nitrophenoxy)-2-[N-(3,4-dimethoxyphenethyl)-N-methylamino]ethane (1) The 2-[N-(3,4-dimethoxyphenethyl)-N-methylamino] ethanol as produced in Example 4-(1) in an amount of 2 g (8.36 mmol) was added to methylene chloride (20 ml) and thionyl chloride (0.91 ml, 12.54 mmol) was slowly added dropwise at room temperature, followed by stirring for 24 h. Thereafter, the reaction mixture was subjected to extraction with methylene chloride and washed with a saturated solution of sodium bicarbonate, followed by drying with anhydrous magnesium sulfate and evaporation of the solvent to yield the end compound 1-chloro-2-[N-(3,4-dimethoxyphenethyl)-N-methylamino]ethane (2.15 g)

$^1$H-NMR (CDCl$_3$): δ6.85(q,1H), 6.75(m,2H), 3.85(s,3H), 3.8(s,3H), 3.61(t,2H), 2.81(t,2H), 2.71(m,4H), 2.39(s,3H)

(2) A portion (1 g, 3.88 mmol) of the 1-chloro-2-[N-(3,4-dimethoxyphenethyl)-N-methylamino]ethane produced in (1) above, 2-(N,N-dimethylamino)-4-nitrophenol (0.598 g, 3.88 mmol) and potassium carbonate (0.536 g, 3.88 mmol) were heated in dimethylformamide (10 ml) at 80° C. for 2 h. Thereafter, the reaction mixture was diluted with a saturated solution of sodium bicarbonate, subjected to extraction with ethyl acetate and dried with anhydrous magnesium sulfate, followed by evaporation of the solvent. The residue was purified by being subjected to column chromatography on silica gel using, as an eluent, chloroform containing methanol (5%) to yield the titled compound 1-[2-(N,N-dimethylamino)-4-nitrophenoxy]-2-[N-(3,4-dimethoxyphenethyl)-N-methylamino]ethane (0.87 g) as a foam.

$^1$NMR (CDCl$_3$): δ7.8(q,1H), 7.65(d,1H), 6.75(d,1H), 6.65 (m,3H), 4.2(t,2H), 3.75(s,3H), 3.8(s,3H), 2.9(t,2H), 2.7(m, 1OH), 2.45(s,3H)

IR(KBr,cm$^{-1}$): 1520, 1335(NO$_2$)

MS: 404(M$^+$+1)

EXAMPLE 13

The following compounds were produced as in Examples 1–12 described above.

(1) 1-(2-Fluoro-4-methanesulfonamidophenoxy)-2-[N-(3,4-dimethoxyphenethyl)-N-methylamino]ethane hydrochloride (foamy substance)

$^1$H-NMR (CDCl$_3$): δ7.15(d,1H,ArH), 6.9(m,2H,ArH), 6.75(m,3H,ArH), 4.55(brs,2H,CH$_2$—O), 3.85(s,6H, OCH$_3$X2), 3.6-3.1 (m, 6H, Ar—CH$_2$CH$_2$—N(CH$_3$)—CH$_2$—CH$_2$—O) 2.95(s,6H,—CH$_2$—N(CH$_3$)—CH$_2$—+SO$_2$CH$_3$)

IR(KBr,cm$^{-1}$): 1160, 1340(S=O)

MS: 166(M$^+$-260), 260(M$^+$-166)

(2) 1-(2-Cyano-4-methanesulfonamidophenoxy)-2-[N-(3,4-dimethoxyphenethyl)-N-methylamino]ethane hydrochloride m.p.: 75.8–78.2° C.

$^1$H-NMR (DMSO-d$_6$): δ9.85(s,1H,NHSO$_2$CH$_3$), 7.53(m, 2H,ArH), 7.34(m,1H,ArH), 6.90(m,2H,ArH), 6.80(d,J=8.2Hz,1H,ArH), 4.58(m,2H,CH$_2$CH$_2$O), 3.75(s,3H,CH$_3$O), 3.73(s,3H, CH$_3$O), 3.59(br m,2H,NCH$_2$CH$_2$O), 2.94(s,3H, CH$_2$NCH$_3$)

IR(KBr,cm$^{-1}$): 3440(NH), 2230(C≡N)

MS: 282(M$^+$-151), 208(M$^+$-225), 165(M$^+$268)

(3) 1-(4-Methanesulfonamido-2-methylphenoxy)-2-[N-(3,4-dimethoxyphenethyl)-N-methylamino]ethane hydrochloride (foamy substance)

$^1$H-NMR (CD$_3$OD): δ7.09–7.12(m,2H,ArH), 6.6–6.98 (m,4H,ArH), 4.39(t,J=4.75Hz,2H,CH$_2$CH$_2$O), 3.81(s,6H, OCH$_3$X2), 3.72(brs,2H,NCH$_2$CH$_2$), 3.53(brs,2H, ArCH$_2$CH$_2$N), 3.09(m,5H,SO$_2$CH$_3$+ArCH$_2$CH$_2$N), 2.89(s, 3H,NCH$_3$), 2.22(s,3H,ArCH$_3$)

IR(KBr,cm$^{-1}$): 3430(NH), 1155(S=O)

MS: 423(M$^+$)

(4) 1-(4-Methanesulfonamido-2-nitrophenoxy)-2-[N-(3,4-dimethoxyphenethyl-N-methylamino]ethane m.p.: 108–110° C.

$^1$H-NMR (DMSO-d$_6$): δ9.78(brs,1H,SO$_2$NH), 7.69(s,1H, ArH), 7.46(d,J=9.0Hz,1H,ArH), 7.37(d,J=9.0Hz,1H,ArH), 6.81(brs,2H,ArH), 6.71(d,J=8.1Hz,1H,ArH), 4.20(t, J=5.3Hz,2H,NCH$_2$CH$_2$—O), 3.72(s,3H, OCH$_3$), 3.71(s,3H, OCH$_3$), 3.00(s,3H,SO$_2$—CH$_3$), 2.80(t,J=5.3Hz,2H, NCH$_2$CH$_2$O), 2.63(s,4H,Ar—CH$_2$CH$_2$N), 2.31(s,3H, NCH$_3$)

IR(KBr,cm$^{-1}$): 3270(NH), 1160(S=O)

MS: 453(M$^+$)

(5) 1-(2,6-Dimethyl-4-methanesulfonamidophenoxy)-2-[N-(3,4-dimethoxyphenethyl)-N-methylamino]ethane (foamy substance)

$^1$H-NMR (CDCl$_3$): δ6.9(s,2H,ArH), 6.75(m,3H,ArH), 4.21(m,2H,OCH$_2$), 3.83(s,3H,OCH$_3$), 3.82(s,3H,OCH$_3$), 3.6–3.05(m,9H,Ar—CH$_2$CH$_2$—N(CH$_3$)—CH$_2$CH$_2$—O), 2.95(s,3H,SO$_2$CH$_3$), 2.25(s,6H,Ar—CH$_3$X2)

IR(KBr,cm$^{-1}$): 1150, 1320(S=O)

MS: 438(M$^+$+1)

(6) 1-(2,6-Diiodo-4-methanesulfonamidophenoxy)-2-[N-(3,4-dimethoxyphenethyl)-N-methylamino]ethane $^1$H-NMR (CD$_3$OD): δ7.65(s,2H,ArH), 6.83(m,3H,ArH), 4.27(t,2H,OCH$_2$), 3.72(m,8H,CH$_3$O+NCH$_2$CH$_2$O), 3.01–3.08(m,7H,CH$_3$SO$_2$NH,N(CH$_3$)—CH$_2$CH$_2$Ar), 2.89 (s,3H,NHCH$_3$)

IR(KBr,cm$^{-1}$): 1160, 1320(S=O)

MS: 509(M$^+$-151)

(7) 1-(2-Chloro-4-methanesulfonamidophenoxy)-2-[N-(4,5-dimethoxy-2-nitrophenethyl)-N-methylamino]ethane hydrochloride (foamy substance)

$^1$H-NMR (CDCl$_3$): δ8.02(s,1H,—NHSO$_2$—), 7.67(s,1H, ArH), 7.41(d,J=2.6Hz,1H,ArH), 7.18(dd,J=2.4Hz,8.8Hz, 1H,ArH), 7.14(s,1H,ArH), 6.85(d,J=8.7Hz,1H,ArH), 4.62–4.67(m,2H,—CH$_2$O—Ar—), 4.01(s,3H,CH$_3$O—Ar), 3.95(s,3H,CH$_3$O—Ar), 3.47–3.66(m,6H,—CH$_2$CH$_2$—N—CH$_2$—), 3.17(s,3H,—SO$_2$CH$_3$), 2.99(s,3H,>N—CH$_3$)

IR(KBr,cm$^{-1}$): 1530(NO$_2$), 1160(SO$_2$)

MS: 488(M$^+$)

(8) 1-(2-Fluoro-4-methanesulfonamidophenoxy)-2-[N-(3,4-dimethoxyphenethyl)-N-isopropylamino]ethane hydrochloride m.p.: 80–84° C.

$^1$H-NMR (CD$_3$OD): δ7.06-6.76(m,6H,ArH), 4.31(t,2H, >NCH$_2$CH$_2$—O—), 3.81(m,1H,>N–CH(CH$_3$)$_2$), 3.70(s,6H, CH$_3$OX2), 3.56(br s, 2H,>NCH$_2$CH$_2$—O—), 3.41(t,2H,—CH$_2$CH$_2$N<), 2.99(t,2H,—CHCH$_2$—N<), 2.86(s,3H, CS$_3$SO$_2$NH—), 1.31(d,6H, CH$_3$—CH(CH$_3$)—)

IR(KBr,cm$^{-1}$): 1480, 2640(≡NH$^+$)

MS: 455(M$^+$+1)

(9) 1-(2-Nitro-4-methanesulfonamidophenoxy)-2-[N-(3,4-dimethoxyphenethyl)-N-isopropylamino]ethane hydrochloride m.p.: 108° C. (with decomposition)

$^1$H-NMR (CD$_3$OD): δ8.06(d,J=2.7Hz,1H,ArH), 7.78(dd, J$_1$=9.1Hz,J$_2$=2.8Hz,1H,ArH), 7.59(d,J=9.1Hz,1H,ArH), 7.14-7.04(m,3H,ArH), 4.68(t,2H,>N—CH$_2$CH$_2$O—), 4.25 (m,1H,>N—CH<), 4.02(t,2H,>NCH$_2$CH$_2$O—), 3.97(s,6H, CH$_3$OX2), 3.76(t,2H,—CH$_2$CH$_2$N<), 3.28(t,2H,—CH$_2$CH$_2$N<), 3.24(s,3H,CH$_3$SO$_2$—NH—), 1.65(m,6H, CH$_3$—CH(CH$_3$)—)

IR(KBr,cm$^{-1}$): 1480 and 2680 (≡N$^+$H), 1160(S=O), 1540(NO$_2$)

MS: 482(M$^+$+1)

(10) 1-(2-Fluoro-4-nitrophenoxy)-2-[N-(3,4-dimethoxyphenethyl)-N-methylamino]ethane hydrochloride (foamy substance)

$^1$H-NMR (CDCl$_3$): δ8.1(d,J=8.5Hz,1H,ArH), 8.0(d,J=8Hz,1H,ArH), 7.15(t,J=8.2Hz,1H,ArH), 6.75(m,3H,ArH), 4.8(br d,2H,O—CH$_2$), 3.87(s,3H,OCH$_3$), 3.85(s,3H,OCH$_3$), 3.75-3.15 (m, 6H, Ar—CH$_2$CH$_2$—N(CH$_3$)—CH$_2$CH$_2$—O), 2.95(s,3H,—N(CH$_3$)—CH$_2$)

IR(KBr,cm$^{-1}$): 1290, 1520(N=O)

MS: 378(M$^+$)

(11) 1-(2-Cyano-4-nitrophenoxy)-2-[N-(3,4-dimethoxyphenethyl )-N-methylamino]ethane hydrochloride m.p.: 182.9–183.6° C.

$^1$H-NMR (DMSO-d$_6$): δ8.76(s,1H,ArH), 8.56(m,1H,ArH), 7.48(d,J=9.4Hz,1H,ArH), 6.90(m,2H,ArH), 6.82(m,1H,ArH), 4.78(t,J=4.5Hz,2H,CH$_2$CH$_2$O), 3.75(s,3H,CH$_3$O), 3.73(s,3H,2CH$_3$O), 3.6(m,2H,CH$_3$NCH$_2$CH$_2$O), 3.41(m,2H,CH$_2$NCH$_3$), 3.03(t,J=8.4Hz,2H,,CH$_2$CH$_{NCH3}$), 2.96(s,3H,NCH$_3$)

IR(KBr,cm$^{-1}$): 2240(C≡N)

MS: 385(M$^+$)

(12) 1-(2-Fluoro-4-cyanophenoxy)-2-[N-(3,4-dimethoxyphenethyl )-N-methylamino]ethane hydrochloride m.p.: 151–152° C.

$^1$H-NMR (CDCl$_3$): δ7.3(m,2H,ArH), 6.9(m,1H,ArH), 6.7 (m,3H,ArH), 4.1(t,J=5.5Hz,2H,CH$_2$—O), 3.77(s,3H,OCH$_3$), 3.75(s,3H,OCH$_3$), 2.8(t,J=5.5Hz,2H,NCH$_2$CH$_2$O), 2.66(m,4H,ArCH$_2$CH$_2$N), 2.35(s,3H,N—CH$_3$)

IR(KBr,cm$^{-1}$): 2130(C≡N)

MS: 359(M$^+$+1)

(13) 1-(4-Methanesulfonamidophenyl)-2-[N-(3,4-dimethoxyphenethyl)-N-methylamino]ethane hydrochloride (foamy substance)

$^1$H-NMR (DMSO-d$_6$): δ10.43(brs,1H,N$^+$H), 9.74(s,1H, NHSO$_2$), 7.26(d,J=8.5Hz,2H,ArH), 7.18(d,J=8.5Hz,2H,ArH), 6.92(brs,2H,ArH), 6.80(d,J=8Hz,1H,ArH), 3.74(s,3H,OCH$_3$), 3.71(s,3H,OCH$_3$), 3.24–3.36(m,4H+H$_2$O, CH$_2$CH$_2$—N(CH$_3$)—CH$_2$CH$_2$), 2.95(brs,7H, SO$_2$CH$_3$+ ArCH$_2$CH$_2$—N(CH$_3$)—CH$_2$CH$_2$Ar), 2.88(s,3H,NCH$_3$)

IR(KBr,cm$^{-1}$): 3430(NH), 1155(S=O)

MS: 241(M$^+$−151), 151(M$^+$−241), 208(M$^+$−184), 184 (M$^+$−208)

(14) 1-(4-Methanesulfonamidophenoxy)-2-[N-(3,4-dimethoxyphenethyl)-N-ethylamino]ethane hydrochloride m.p.: 54–56° C.

$^1$H-NMR (CD$_3$OD): δ7.25(d,J=6.8Hz,2H,ArH), 7.0(d,J=6.9Hz,2H,ArH), 6.93-6.86(m,3H,ArH), 4.38(t,J=4.8Hz,2H, NCH$_2$CH$_2$O—Ar), 3.81(s,6H,ArOCH$_3$X2), 3.68(t,2H,N—CH$_2$CH$_2$O—), 3.43–3.48(m,4H,ArCH$_2$CH$_2$N), 3.06(t,2H, N—CH$_2$CH$_3$), 2.9(s,3H,SO$_2$—CH$_3$), 1.42(t,3H,N—CH$_2$CH$_3$)

IR(KBr,cm$^{-1}$): 1240–1260(CH$_3$—O—Ar)

MS: 423(M$^+$)

(15) 1-[[(4-Methanesulfonamidophenoxy)ethyl]-N-methylamino]-2-[N-(3,4-dimethoxybenzoyl)amino]ethane m.p.: 90–96° C.

$^1$H-NMR (CDCl$_3$): δ7.45(d,J=2.0Hz,1H,ArH), 7.29-7.15 (m,3H,ArH), 6.95(br s,1H,—CONH—), 6.85-6.77(m,3H, ArH), 4.07(t,J=5.2Hz,>NCH$_2$CH$_2$O—), 3.92(s,3H, ArH), 3.90(s,3H,CH$_3$O—), 3.56(m,2H,—CONHCH$_2$CH$_2$N<), 2.95(s,3H,CH$_3$SO$_2$NH—), 2.89(t,2H, J=5.2Hz, >NCH$_2$CH$_2$—), 2.74(t,J=5.8Hz,—CONHCH$_2$CH$_2$—N<), 2.43(s,3H,CH$_3$—N<)

IR(KBr,cm$^{-1}$): 1640(amide)

MS: 452(M$^+$+1)

EXAMPLE 14

The following compounds (1)–(14) were produced as in Examples 1–12 described above.

(1) 1-[2-(N,N-Dimethylamino)-4-methanesulfonamidophenoxy]-2-[N-(3,4-dimethoxyphenethyl)-N-methylamino]ethane dihydrochloride

MS: 452(M$^+$+1)

(2) 1-(2-Hydroxy-4-methanesulfonamidophenoxy)-2-[N-(3,4-dimethoxyphenethyl)-N-methylamino]ethane hydrochloride m.p.: 187–197° C.

(3) 1-(4-Methanesulfonamido-2-methanesulfonyloxyphenoxy)-2-[N-(3,4-dimethoxyphenethyl)-N-methylamino]ethane hydrochloride

MS: 503(M$^+$)

(4) 1-(2,6-Dimethyl-4-methanesulfonamidophenoxy)-2-[N-(3,4-dimethoxyphenethyl)-N-isopropylamino]ethane hydrochloride (5) N-Methyl-N-[2-(3,4-dimethoxyanilino)ethyl]-4-[(methylsulfonyl)amino]benzensulfonamide m.p.: 53–55° C.

(6) 1-(2-Acetyl-4-methanesulfonamidophenoxy)-2-[N-(3,4-dimethoxyphenethyl)-N-methylamino]ethane hydrochloride

MS: 452(M$^+$+1)

(7) 1-(3-Fluoro-4-methanesulfonamidophenoxy)-2-[N-(3,4-dimethoxyphenethyl)-N-methylamino]ethane hydrochloride m.p.: 82.4° C. (with decomposition)

(8) 1-(2,6-Diiodo-4-methanesulfonamidophenoxy)-2-[N-(3,4-dimethoxyphenethyl)-N-isopropylamino]ethane

MS: 689(M$^+$+1)

(9) N-(3,4-Dimethoxyphenyl)-4-methanesulfonamidophenethylamine hydrochloride

MS: 350(M$^+$)

(10) 1-(Methanesulfonamidophenoxy)-2-[N-(3,4-dimethoxyphenethyl)-N-phenylamino]ethane

MS: 470(M$^+$)

(11) 1-(4-Methanesulfonamido-3-nitrophenoxy)-2-[N-(3,4-dimethoxyphenethyl)-N-methylamino]ethane hydrochloride

MS: 454(M$^+$+1)

(12) 1-(2-Iodo-4-methanesulfonamidophenoxy)-2-[N-(3,4-dimethoxyphenethyl)-N-methylamino]ethane hydrochloride

(13) 1-(4-Methanesulfonamido-2-methoxy)phenoxy-2-[N-(3,4-dimethoxyphenethyl)-N-methylamino]ethane

MS: 288(M$^+$−150), 150(M$^+$−288)

(14) 1-(4-Methanesulfonylamidoanilino)-2-[N-(3,4-dimethoxyphenethyl)-N-methylamino]ethane hydrochloride

MS: 407(M$^+$+1)

EXAMPLE 15

Production of 1-[4-(methanesulfonylamido-2-(N-2'-thiazolyl)aminophenoxy]-2-[N-(3,4-dimethoxyphenethyl)-N-methylamino]ethane hydrochloride (1) 2-Amino-4-nitrophenol (10 g, 64.9 mmol) and 2-bromothiazole (5.75 ml, 64.9 mmol) were dissolved in DMF (20 ml) and thereafter the solution was stirred at 120–130° C. for 5 h. The reaction solution was cooled to room temperature, diluted with a saturated aqueous solution of sodium bicarbonate (50 ml) and subjected to extraction with methylene chloride (300 ml). The extracted organic layer was dried with sodium sulfate and the solvent was evaporated; the resulting residue was purified by being subjected to column chromatography on silica gel using a 1:1 solvent system of n-hexane and ethyl acetate as an eluent. The fractions containing the product were collected and the solvent was evaporated to yield the end compound 4-nitro-2-(21 -thiazolyl)aminophenol (2.0 g).

¹H-NMR (DMSO-d₆): δ9.92(s,1H), 9.46(d,J=2.9Hz,1H), 7.96–7.98(m,1H), 7.79(dd,J₁=8.8Hz,J₂=2.9Hz,1H), 7.36(d, J=3.6Hz,1H), 6.97–7.00(m,2H)

(2) 4-Nitro-2-(2'-thiazolyl)aminophenol (1.8 g, 7.59 mmol) was dissolved in THF (50 ml) and acetic anhydride (5 ml) was added dropwise, followed by stirring first at room temperature for 1 h, then at 50° C. for 3 h. Methanol (50 ml) was added to the reaction solution, which was stirred for 30 min, followed by concentration under vacuum, dilution with a saturated aqueous solution of sodium bicarbonate (100 ml) and extraction with chloroform (300 ml). The extracted organic layer was dried with sodium sulfate and the solvent was evaporated; the resulting residue was recrystallized in diethyl ether to yield the end compound [4-nitro-2-[(N-2'-thiazolyl)acetamide]phenyl]acetate (1.4 g).

¹H-NMR (CDCl₃): δ8.43(dd,J₁=9.0Hz,J₂=2.7Hz,1H), 8.36(d,J=2.6Hz,1H), 7.59(d,J=8.9Hz,1H), 7.38(d,J=3.6Hz, 1H), 7.07(d,J=3.5Hz,1H), 2.13(s,3H), 2.10(s,3H)

(3) [4-Nitro-2-[N-2'-thiazolyl)acetamido]phenyl]acetate (1.4 g, 4.36 mmol) and potassium carbonate (3.01 g, 21.8 mmol) were dissolved in DMF (20 ml) and the solution was heated at 70° C.; after adding dibromoethane (1.88 ml, 21.8 mmol) dropwise, the solution was stirred at the same temperature for 20 min. The reaction solution was cooled to room temperature, diluted with a saturated aqueous solution of sodium bicarbonate (30 ml) and subjected to extraction with methylene chloride. The extracted organic layer was dried with sodium sulfate and the solvent was evaporated; the resulting residue was purified by being subjected to column chromatography on silica gel using a 1:1 solvent system of n-hexane and ethyl acetate as an eluent to yield the end compound 2-bromo-1-[4-nitro-2-(N-2'-thiazolyl)-acetamidophenoxy]ethane (0.7 g).

¹H-NMR (CDCl₃): δ8.42(dd,J₁=9.2Hz,J₂=2.7Hz,1H), 8.30(d,J=2.7Hz,1H), 7.35(d,J=3.6Hz,1H), 7.17(d,J=9.1Hz, 1H), 7.04(d,J=3.6Hz,1H), 4.42(t,J=5.9Hz,2H), 3,48(t,J=5.9Hz,2H), 2.12(s,3H)

(4) 2-Bromo-1-[4-nitro-2-(N-2'-thiazolyl) acetamidophenoxy]ethane (0.53 g, 1.372 mmol) and 2-(3, 4-dimethoxyphenyl)-N-methylethylamine (0.76 ml, 4.117 mmol) were dissolved in a 2:1 solvent system (15 ml) of acetonitrile and ethanol and the solution was stirred at the reflux temperature for 7 h. The reaction solution was cooled to room temperature and the solvent was evaporated under vacuum, with the resulting residue being purified by being subjected to column chromatography on silica gel using a 30:1 solvent system of chloroform and methanol as an eluent. The fractions containing the product were collected and the solvent was evaporated to yield the end compound 1-[4-nitro-2-(N-2'-thiazolyl)acetamidophenoxy]-2-[N-(3,4-dimethoxyphenethyl)-N-methylamino]ethane (0.7 g).

¹H-NMR (CDCl₃): δ8.40(dd,J₁=9.2H,J₂=2.8Hz,1H), 8.28 (d,J=2.7Hz,1H), 7.34(d,J=3.5Hz,1H), 7.16(d,J=9.2Hz,1H), 7.01(d,J=3.6Hz,1H), 6.78(d,J=8.6Hz,1H), 6.68–6.69(m, 2H), 4.17(t,J=5.5Hz,2H), 3.87(s,3H), 3.86(s,3H), 2.69–2.72 (m,2H), 2.55–2.63(m,4H), 2.21(s,3H), 2.08(s,3H)

(5) 1-[4-nitro-2-(N-2'-thiazolyl)acetamidophenoxy]-2-[N-(3,4-dimethoxyphenethyl)-N-methylamino]ethane (0.7 g, 1.398 mmol) were dissolved in ethyl acetate and 5% Pd/C (0.3 g) was added, followed by injection of hydrogen gas and stirring at room temperature for 3 h. Thereafter, filtration was performed using Celite and the solvent was evaporated; the resulting residue was purified by being subjected to column chromatography on silica gel using a 45:1 solvent system of chloroform and methanol as an eluent. The fractions containing the product were collected and the solvent was evaporated to yield the end compound 1-[4-amino-2-(N-2'-thiazolyl)aminophenoxy]-2-[N-(3,4-dimethoxyphenethyl)-N-methylamino]ethane (0.48 g).

¹H-NMR (CDCl₃): δ9.66(s,1H), 7.76(d,J=2.7Hz,1H), 7.28(d,J=3.7Hz,1H), 6.03(d,J=8.4Hz,1H), 6.72–6.76(m, 3H), 6.59(d,J=3.7Hz,1H), 6.24(dd,J₁=8.4Hz,J₂=2.7Hz,2H), 4.03(t,J=5.1Hz,2H), 3.84(s,3H), 3.83(s,3H), 2.73–2.83(m, 6H), 2.44(s,3H)

(6) 1-[4-Amino-2-(N-2'-thiazolyl)aminophenoxy]-2-[N-(3,4-dimethoxyphenethyl)-N-methylamino]ethane (60 mg, 0.14 mmol) was dissolved in pyridine (2 ml) and, thereafter, the solution was cooled to 0° C. and stirred at the same temperature for 1 h as methanesulfonyl chloride (24 mg, 0.21 mmol) was slowly added dropwise; the solvent was evaporated under vacuum and the residue was diluted with 5 ml of a saturated aqueous solution of sodium bicarbonate, followed by extraction with chloroform. The extracted organic layer was dried with sodium sulfate and the solvent was evaporated; the resulting residue was purified by being subjected to column chromatography on silica gel using a 30:1 solvent system of chloroform and methanol. The fractions containing the product were collected and the solvent was evaporated to yield a colorless oil, which was dissolved in methanol; after passing hydrogen chloride gas for 2 min, the solvent was evaporated under vacuum to yield the tilted compound 1-[4-methanesulfonylamido-2-(N-2'-thiazolyl) aminophenoxy]-2-[N-(3,4-dimethoxyphenethyl)-N-methylamino]ethane hydrochloride (65 mg).

m.p.: 130.4–132.6° C.

¹H-NMR (DMSO-d₆): δ11.02(brs,1H,HCl), 10.15(brs, 1H,thiazole—NH), 9.46(s,1H,NHSO₂CH₃), 8.29(d,J=2.3Hz,1H,ArH), 7.29(d,J=3.8Hz,1H,thiazole(H)), 7.05(d,1H, ArH), 6.96(d,J=3.7Hz,1H,thiazole(H)), 6.88-6.79(m,4H, ArH), 4.38(t,2H,N(CH₃)CH₂CH₂O), 3.71(s,3H,CH₃O), 3.71(s,3H,CH₃O), 3.60(t,2H,ArCH₂CH₂N(CH₃)CH₂), 3.23 (t,2H,ArCH₂CH₂N(CH₃)CH₂), 3.08(t,2H,N(CH₃) CH₂CH₂O), 2.92(s,3H,CH₃SO₂NH), 2.88(d,J=3.1Hz,3H, CH₂N(CH₃)CH₂)

IR(KBr,cm⁻¹): 3420(NH), 2960(≡N⁺H), 1330 and 1160 (S=O)

EXAMPLE 16

Production of 1-[4-methanesulfonamido-2-(1H-pyrrol-1-yl) phenoxy]-2-[N-(4-methanesulfonamidophenethyl)-N-methylamino]ethane (1) 2-Amino-4-nitrophenol (5 g, 32.0 mmol) and 2,5-dimethoxytetrahydrofuran (5.03 ml, 38.4 mmol) were dissolved in glacial acetic acid (100 ml), followed by stirring at the reflux temperature for 10 min. After subsequent cooling to room temperature, the solvent was evaporated under vacuum and the residue was neutralized with an aqueous solution of sodium carbonate, followed by three extractions with ethyl acetate. The organic solvent layers were combined, dried with magnesium sulfate and the solvent was evaporated; thereafter, the residue was purified by being subjected to column chromatography on silica gel using a 2:1 solvent system of n-hexane and ethyl acetate as an eluent; the fractions containing the product were collected and the solvent was evaporated to yield the end compound 4-nitro-2-(1H-pyrrol-1-yl)phenol (3.81 g).

¹H-NMR (CDCl₃): δ8.10–8.20(m,2H), 7.13(d,1H), 6.92 (dd,2H), 6.42(dd,2H)

(2) 4-Nitro-2-(1H-pyrrol-1-yl)phenol (2.3 g, 112.6 mmol) and dibromoethane (29.1 ml, 337.8 mmol) were dissolved in DMF (200 ml) and, after adding K₂CO₃ (18.68 g), the solution was stirred at 70° C. for 1 h. Thereafter, an aqueous solution of 10% sodium hydroxide was added to the reaction solution to render it basic up to a pH of about 10, followed by three extractions with ethyl acetate. The organic solvent layers were combined and dried with magnesium sulfate, followed by evaporation of the solvent. The resulting residue was purified by being subjected to column chromatography on silica gel using a 3:1 solvent system of n-hexane and ethyl acetate as an eluent. The fractions containing the product were collected and the solvent was evaporated to yield the end product 4-nitro-2-(1H-pyrrol-1-yl)phenoxy-2-bromoethane (15.8 g).

$^1$H-NMR (CDCl$_3$): δ8.13–8.23(m,2H), 7.10–7.16(m,3H), 6.36(dd,2H), 4.45(t,J=5.8Hz,2H), 3.67(t,J=5.8Hz,2H)

(3) 4-Nitrophenethyl-N-methylamine (0.81 g, 4.5 mmol) and 4-nitro-2-(1H-pyrrol-1-yl)phenoxy-2-bromoethane (0.7 g, 2.25 mmol) were dissolved in a 1:2 solvent system of ethanol and acetonitrile and the solution was heated at the reflux temperature for 15 h. Thereafter, the solvent was evaporated and the residue was diluted with water; the aqueous layer was rendered basic to a pH of about 9 with an aqueous solution of sodium carbonate, followed by three extractions with ethyl acetate. The organic solvent layers were combined, dried with magnesium sulfate, and the solvent was evaporated. The resulting residue was purified by being subjected to column chromatography on silica gel using a 1:1 solvent system of n-hexane and ethyl acetate as an eluent. The fractions containing the product were collected and the solvent was evaporated to yield the end compound 1-[4-(nitro-2-(1H-pyrrol-1-yl)phenoxy-2-[N-(4-nitrophenethyl)-N-methylamino]ethane (0.71 g) as a pale brown oil.

$^1$H-NMR (CDCl$_3$): δ8.10–8.19(m,4H), 7.25–7.35(m,2H), 7.00–7.15(m,3H), 6.33(dd,2H), 4.16(t,2H), 2.78–2.98(m,4H), 2.75(t,2H), 2.39(s,3H)

(4) 1-[4-Nitro-2-(1H-pyrrol-1-yl)phenoxy]-2-[N-(4-nitrophenethyl)-N-methylamino]ethane (0.71 g, 1.73 mmol) was dissolved in 80 ml of a 1:1 solvent system of ethyl acetate and methanol and, after slowly adding 10% Pd/C (0.2 g), the solution was stirred at an ordinary temperature for 3 h as hydrogen gas was injected. Thereafter, the reaction mixture was filtered through Celite and the filtrate was evaporated to yield the compound 1-[4-amino-2-(1H-pyrrol-1-yl)phenoxy]-2-[N-(4-aminophenethyl)-N-methylamino]ethane (0.6 g) as a dark brown oil. The compound was dissolved in pyridine (30 ml) and, thereafter, the solution was cooled at 0° C. and methanesulfonyl chloride (0.344 ml, 4.45 mmol) was slowly added. Thereafter, the mixture was stirred at an ordinary temperature for 20 h and ethanol was added; the solvent pyridine was evaporated under vacuum and the resulting residue was added to an aqueous solution of 10% sodium hydroxide, followed by extraction with ethyl acetate. The organic layer was washed with water twice, dried with magnesium sulfate, and the solvent was evaporated. The residue was purified by being subjected to column chromatography on silica gel using, as an eluent, ethyl acetate containing 5% methanol. The fractions containing the product were collected and the solvent was evaporated to yield the titled compound 1-[4-methanesulfonamido-2-(1H-pyrrol-1-yl)phenoxy]-2-[N-(4-methanesulfonamidophenethyl)-N-methylamino]ethane (0.43 g) as a pale yellow substance.

$^1$H-NMR (CDCl$_3$): δ7.22-6.95(m,7H,ArH), 7.03(dd,2H,pyrrole(H)), 6.29(dd,2H,pyrrole(H)), 4.02(t,J=5.5Hz,2H, CH$_2$N(CH$_3$)CH$_2$CH$_2$O), 3.05(s,3H,CH$_3$SO$_2$NH), 2.98(s,3H,CH$_3$SO$_2$NH), 2.82(t,J=5.5Hz,2H,CH$_2$N(CH$_3$) CH$_2$CH$_2$O), 2.58–2.79(m,4H,ArCH$_2$CH$_2$N(CH$_3$)CH$_2$), 2.38 (s,3H,CH$_2$N(CH )CH$_2$)

IR(KBr,cm$^{-1}$): 3240(NH), 1330 and 1160(S=O)

EXAMPLE 17

Production of 1-[4-methanesulfonamido-2-[(N-2'-thiazolyl) amido]phenoxy]-2-[N-methyl-N-(4-methanesulfonamidophenethyl)amino]ethane hydrochloride (1) 4-[2-(methylamino)ethyl]methanesulfonanilide (0.55 g, 2.59 mmol) and 2-bromo-1-[4-nitro-2-[(N-2'-thiazolyl) acetamido]phenoxy]ethane (0.5 g, 1.29 mmol) were dissolved in 20 ml of a 2:1 solvent system of acetonitrile and ethanol and the solution was stirred at the reflux temperature for 7 h. The solvent was evaporated under vacuum and the resulting residue was purified by being subjected to column chromatography on silica gel using a 9:1 solvent system of chloroform and methanol as an eluent. The fractions containing the product were collected and the solvent was evaporated to yield the end compound 1[4-nitro-2-[(N-2'thiazolyl)acetamido]phenoxy]-2-[N-methyl-N-(4-methanesulfonamidophenethyl)amino]ethane (0.32 g) as a yellow solid mass.

$^1$H-NMR (CDCl$_3$): δ8.43(dd,J$_1$=9.8Hz,J$_2$=2.8Hz,1H), 8.30(d,J=2.7Hz,lH), 7.36(d,J=3.5Hz,1H), 7.04–7.23(m,5H), 7.03(d,J=3.5Hz,1H), 4.10–4.22(m,2H), 3.02(s,3H), 2.56–2.73(m,6H), 2.22(s,3H), 2.13(s,3H)

(2) 1-[4-Nitro-2-[(N-2'-thiazolyl)acetamido]phenoxy]-2-[N-methyl-N-(4-methanesulfonamidophenethyl)amido] ethane (0.32 g, 0.60 mmol) was dissolved in 20 ml of a 1:1 solvent system of ethyl acetate and methanol; thereafter, 10% Pd/C (0.16 g) was added and the solution was stirred at room temperature for 1 h with hydrogen gas injected. Thereafter, the solution was filtered through Celite and the solvent was evaporated; the resulting residue (0.3 g) was dissolved in pyridine (20 ml) and, thereafter, the solution was cooled at 0° C. and methanesulfonyl chloride (0.11 ml, 1.39 mmol) was slowly added dropwise, followed by stirring at room temperature for 2 h; thereafter, water was added and extraction was effected with ethyl acetate. The organic layer was dried with magnesium sulfate and the solvent was evaporated; the resulting residue was purified by being subjected to column chromatography on silica gel using a 9:1 solvent system of chloroform and methanol as an eluent. The fractions containing the product were collected and the solvent was evaporated to yield the end compound 1-[4-methanesulfonamido-2-[(N-2'-thiazolyl)amido]phenoxy]-2-[N-methyl-N-(4-methanesulfonamidophenethyl)amino] ethane (0.15 g).

$^1$H-NMR (CDCl$_3$): δ8.26(d,J=2.3Hz,1H), 7.32(d,J=3.7Hz,1H), 7.02(d,2H), 7.10(d,2H), 6.89–6.99(m,2H), 6.69 (d,J=3.6Hz,1H), 4.09(t,J=5.5Hz,2H), 3.07(s,1H), 2.97(s,1H), 2.82–2.86(m,6H), 2.47(s,3H)

(3) 1-[4-Methanesulfonamido-2-[(N-2'-thiazolyl)amido] phenoxy]-2-[N-methyl-N-(4-methanesulfonamidophenethyl)amino]ethane (40 mg, 0.07 mmol) was dissolved in absolute methanol (15 ml) and, thereafter, a solution of 1N HCl (0.15 ml) saturated with ethyl ether was added at 0° C., followed by stirring at the same temperature for 30 min; upon concentration, there was yielded the titled compound 1-[4-methanesulfonamido-2-[(N-2'-thiazolyl)amido]phenoxy]-2-[N-methyl-N-(4-methanesulfonamidophenethyl)amino]ethane hydrochloride (40 mg).

$^1$H-NMR (MeOH-d$_4$): δ7.57(s,1H,ArH), 7.28(brs,1H,thoazole(H)), 7.09–7.20(m,6H,ArH), 6.95(s,1H,thizole(H)), 4.40(brs,2H,N(CH$_3$)CH$_2$CH$_2$O), 3.62(brs,2H,N(CH$_3$) CH$_2$CH$_2$O), 3.38(t,2H,ArCH$_2$CH$_2$N(CH$_3$)CH$_2$), 3.04(t,2H, ArCH$_2$N(CH$_3$)CH$_2$), 2.93(s,3H,CH$_3$SO$_2$NH), 2.88(s,3H, CH$_3$SO$_2$NH), 2.84(d,3H,CH$_2$N(CH$_3$)CH$_2$)

IR(KBr,cm$^{-1}$): 3150(NH), 2950(≡N$^+$H), 1330 and 1160 (S=O)

MS: 540(M+)

EXAMPLE 18

Production of 1-[4-methanesulfonamido-2-(1H-pyrrol-1-yl)phenoxy]-2-[N-(3,4-dimethoxyphenethyl)-N-isopropylamino]ethane hydrochloride (1) 3,4-Dimethoxyphenethylmethanesulfonate (3 g, 12.0 mmol) and isopropylamine (9.8 ml, 120 mmol) were dissolved in methanol (10 ml) and the solution was stirred at the reflux temperature for 5 h to effect evaporation; after neutralization with an aqueous solution of 2N NaOH, extraction was conducted with ethyl acetate. The extracted organic layer was dried with magnesium sulfate and the solvent was evaporated; the resulting residue was purified by being subjected to column chromatography on silica gel using a 9:1 solvent system of chloroform and methanol as an eluent. The fractions containing the product were collected and the solvent was evaporated to yield the end compound 2-(3,4-dimethoxyphenyl)-N-isopropylethylamino (2.4 g).

$^1$H-NMR (CDCl$_3$): δ6.65–6.80(m,3H), 4.59(brs,1H), 3.88 (s,3H), 3.87(s,3H), 2.85–3.07(m,4H), 2.82(m,1H), 1.21(d, J=6.4Hz,6H)

(2) 2-(3,4-Dimethoxyphenyl)-N-isopropylethylamine (2.4 g, 11 mmol) and 1-[4-nitro-2-(1H-pyrrol-1-yl)phenoxy]-2-bromoethane (3.04 g, 10 mmol) were dissolved in DMF and, thereafter, potassium iodide (1.61 g, 11 mmol) and anhydrous potassium carbonate (1.5 g, 10 mmol) were added and the mixture was stirred at 80–90° C. for 1 h; thereafter, ice water was added and extraction was conducted with ethyl acetate. The extracted organic layer was dried with magnesium sulfate and the solvent was evaporated; the resulting residue was purified by being subjected to column chromatography on silica gel using a 7:3:1 solvent system of cyclohexane, ethyl acetate and methanol as an eluent. The fractions containing the product were collected and the solvent was evaporated to yield the end compound 1-[4-nitro-2-(1H-pyrrol-1-yl)phenoxy]-2-[N-(3,4-dimethoxyphenethyl)-N-isopropylamino]ethane (0.9 g).

$^1$H-NMR (CDCl$_3$): δ8.15–8.23(m,2H), 7.10(dd,2H), 7.01 (d,1H), 6.77(d,1H), 6.67–6.75(m,2H), 6.34(dd,2H), 4.0(t,J= 6.4Hz,2H), 3.87(s,3H), 3.85(s,3H), 2.98–3.04(m,1H), 2.88 (t,J=6.4Hz,2H), 2.64–2.74(m,4H), 1.03(d,=6.5Hz,6H)

(3) 1-[4-Nitro-2-(1H-pyrrol-1-yl)phenoxy]-2-[N-(3,4-dimethoxyphenethyl)-N-isopropylamino]ethane (0.9 g, 1.98 mmol) was dissolved in 50 ml of a 1:1 solvent system of ethyl acetate and methanol; following 10% Pd/C (0.4 g), the solution was stirred at room temperature for 1 h as hydrogen gas was introduced. Thereafter, the reaction solution was filtered through Celite and the solvent was evaporated; the resulting residue (0.7 g) was dissolved in pyridine (20 ml) and, thereafter, the solution was cooled to 0° C. and methanesulfonyl chloride (0.19 ml, 2.5 mmol) was slowly added dropwise and the mixture was stirred at room temperature for 2 h; thereafter, water was added and extraction was conducted with ethyl acetate. The extracted organic layer was dried with magnesium sulfate and the solvent was evaporated; the resulting residue was purified by being subjected to column chromatography on silica gel using a 7:3:1 solvent system of cyclohexane, ethyl acetate and methanol as an eluent. The fractions containing the product were collected and the solvent was evaporated; the residue was dissolved in methanol (10 ml); after cooling to 0° C., a solution of 1N HCl (0.15 ml) saturated with ethyl ether was added and the mixture was stirred for 20 min to effect evaporation and thereby yield the titled compound 1-[4-methanesulfonamido-2-(1H-pyrrol-1-yl)phenoxy]-2-[N-(3,4-dimethoxyphenethyl)-N-isopropylamino]ethane hydrochloride (0.28 g).

$^1$H-NMR (MeOH-d$_4$): δ7.37-7.21(m,3H,ArH), 6.94(dd, 2H,pyrrole(H)), 6.92-6.78(m,3H,ArH), 6.21(dd,2H,pyrrole (H)), 4.38(t,2H,NCH$_2$CH$_2$O), 3.83(s,3H,CH$_3$O), 3.82(s,3H, CH$_3$O), 3.70–3.81(m,3H,NCH$_2$CH$_2$O NCH(CH$_3$)$_2$), 3.55 (brs,2H,ArCH$_2$CH$_2$NCH$_2$), 2.97(s,3H,CH$_3$SO$_2$NH), 2.95 (brs,2H,ArCH$_2$CH$_2$), 1.31(dd,6H,(CH$_3$)$_2$CH)

IR(KBr,cm$^{-1}$): 3320(NH), 2970(≡N$^+$H), 1340 and 1160 (S=O)

EXAMPLE 19

Production of 1-(2-benzyloxy-4-methanesulfonamidophenoxy)-2-[N-(3,.4-dimethoxyphenethyl)-N-methylamino]ethane hydrochloride (1) 4-Nitrocatechol (5 g, 32.2 mmol) was dissolved in DMF (50 ml); thereafter, potassium carbonate (8.9 g, 64.5 mmol) was added and with heating at 70–75° C., ethyl bromoacetate (7.18 ml) was slowly added dropwise, followed by stirring at the same temperature for 15 min. The reaction solution was cooled to room temperature and filtered; after being concentrated under vacuum, the filtrate was diluted with a saturated aqueous solution of sodium bicarbonate (50 ml) and subjected to extraction with ethyl acetate (300 ml). The extracted organic layer was dried with magnesium sulfate and the solvent was evaporated. The resulting residue was purified by being subjected to column chromatography on silica gel using a 2:1 solvent system of n-hexane and ethyl acetate as an eluent. The fractions containing the product were collected and the solvent was evaporated to yield the end compound ethyl (2-hydroxy-4-nitrophenoxy)acetate (1.05 g).

$^1$H-NMR (CDCl$_3$): δ7.87(d,J=2.7Hz,1H), 7.82(dd, J$_1$8.8Hz,J=$_2$2.7Hz,1H), 7.01(s,1H), 6.94(d,J=8.8Hz,1H), 4.78(s,2H), 4.33(q,J=7.1Hz,2H), 1.34(t,J=7.0Hz,3H)

(2) Ethyl (2-hydroxy-4-nitrophenoxy)acetate (1.05 g, 4.34 mmol) and potassium carbonate (2.40 g, 17.35 mmol) were dissolved in DMF (30 ml); thereafter, benzyl bromide (2.56 ml, 21.68 mmol) was added dropwise to the solution, which was stirred for 1.5 h with heating at 70° C. After being cooled to room temperature, the reaction solution was diluted with a saturated aqueous solution of sodium bicarbonate (40 ml), followed by extraction with methylene chloride (300 ml). The extracted organic layer was dried with magnesium sulfate and the solvent was evaporated; the resulting residue was purified by being subjected to column chromatography on silica gel using a 4:1 solvent system of n-hexane and ethyl acetate as an eluent. The fractions containing the product were collected and the solvent was evaporated to yield the end compound ethyl(2-benzyloxy-4-nitrophenoxy) acetate (0.85 g).

$^1$H-NMR (CDCl$_3$): δ7.89(d,J=8.7Hz,1H), 7.86(dd,J$_1$= 8.8Hz,J$_2$=2.5Hz,1H), 7.36–7.52(m,5H), 6.88(d,J=8.7Hz, 1H), 5.25(s,2H), 4.82(s,2H), 4.30(q,J=7.1Hz,2H), 1.32(t,J= 7.1Hz,3H)

(3) Ethyl (2-benzyloxy-4-nitrophenoxy)acetate (800 mg, 4.83 mmol) was dissolved in THF (50 ml); thereafter, sodium borohydride (457 mg, 12.1 mmol) was added and the mixture was heated to the reflux temperature. At the same temperature, methanol (5 ml) was slowly added dropwise over 30 min, followed by stirring at the reflux temperature for 30 min. The reaction solution was cooled to room temperature and water (10 ml) was added, followed by extraction with ethyl acetate (200 ml). The extracted organic layer was dried with magnesium sulfate and the solvent was evaporated; the resulting residue was purified by being subjected to column chromatography on silica gel using a 1:1 solvent system on n-hexane and ethyl acetate as an eluent. The fractions containing the product were collected and the solvent was evaporated to yield the end compound 2-(2-benzyloxy-4-nitrophenoxy)ethanol (400 ml).

$^1$H-NMR (CDCl$_3$): δ7.84(dd,J$_1$=9.0Hz,J$_2$=2.6Hz,1H), 7.77(d,J=2.6Hz,1H), 7.31–7.38(m,5H), 6.89(d,J=8.9Hz, 1H), 5.12(s,2H), 4.14(t,J=4.5Hz,2H), 3.93(t,J=4.4Hz,2H), 2.24(s,1H)

(4) 2-(2-Benzyloxy-4-nitrophenoxy)ethanol (400 mg, 1.383 mmol) was dissolved in pyridine (5 ml); after cooling at 0° C., methanesulfonyl chloride (0.22 ml, 2.76 mmol) was slowly added dropwise, followed by stirring at room temperature for 2 h. The solvent was evaporated under vacuum and the residue was diluted with a saturated aqueous solution of sodium bicarbonate (10 ml), followed by extraction with chloroform (100 ml). The extracted organic layer was dried with sodium sulfate and the solvent was evaporated; the resulting residue was dissolved in 15 ml of a 1:2 solvent system of ethanol and acetonitrile and, thereafter, 2-[N-(3, 4-dimethoxyphenethyl)-N-methylamino]ethane (0.765 ml, 4.148 mmol) was added, followed by stirring at the reflux temperature for 8 h. The reaction solution was cooled to room temperature and thereafter the solvent was evaporated; the resulting residue was purified by being subjected to column chromatography on silica gel using a 1:1 solvent system of n-hexane and ethyl acetate as an eluent. The fractions containing the product were collected and the solvent was evaporated to yield the end compound 1-(2-benzyloxy-4-nitrophenoxy)-2-[N-(3,4-dimethoxyphenethyl)-N-methylamino]ethane (600 mg).

$^1$H-NMR (CDCl$_3$): δ8.11(dd,J$_1$=8.9Hz,J$_2$=2.6Hz,1H), 7.84(d,J=2.6Hz,1H), 7.36–7.46(m,5H), 6.95(d,J=8.9Hz, 1H), 6.73–6.78(m,3H), 5.19(s,2H), 4.23(t,J=5.8Hz,2H), 3.87(s,3H), 3.86(s,3H), 2.98(t,J=5.8Hz,2H), 2.68-2.83(m, 4H), 2.47(s,3H)

(5) 1-(2-Benzyloxy-4-nitrophenoxy)-2-[N-(3,4-dimethoxyphenethyl)-N-methylamino]ethane (600 mg,1.286 mmol) was dissolved in ethanol (16 ml); thereafter, an aqueous solution (5 ml) of sodium hydrogensulfite (897 mg, 5.144 mmol) was slowly added dropwise, followed by stirring first at room temperature for 30 min, then at 50° C. for 30 min. The insoluble solids were filtered off and the filtrate was evaporated, followed by extraction with ethyl acetate (100 ml). The extracted organic layer was dried with sodium sulfate and the solvent was evaporated; the resulting residue was dissolved in pyridine (5 ml), and thereafter, the solution was cooled to 0° C. and methanesulfonyl chloride (0.1 ml, 1.286 mmol) was slowly added dropwise, followed by stirring at room temperature for 2 h. The solvent was evaporated under vacuum and the residue was diluted with a saturated aqueous solution of sodium bicarbonate (10 ml), followed by extraction with chloroform (50 ml). The extracted organic layer was dried with sodium sulfate and the solvent was evaporated; the resulting residue was purified by being subjected to column chromatography on silica gel using a 15:1 solvent system of ethyl acetate and methanol as an eluent. The fractions containing the product were collected and the solvent was evaporated, after passing HCl gas for 2 min, the solvent was evaporated to yield the titled compound 1-(2-benzyloxy-4-methanesulfonylamidophenoxy)-2-[N-(3,4-dimethoxyphenethyl)-N-methylamino]ethane hydrochloride (120 mg).

$^1$H-NMR(CDCl$_3$):δ 12.41(s,1H,HCl), 7.32 (m,5H,ArH), 7.06(d,J=2.3Hz,1H,ArH), 6.85-6.72(m,5H,ArH), 5.00(s,2H, ArCH$_2$O), 4.47(t,2H,CH$_2$N(CH$_3$)CH$_2$CH$_2$O), 3.84(s,3H, CH$_3$O), 3.82(s,3H,CH$_3$O), 3.50-3.12(m,6H,ArCH$_2$CH$_2$N (CH$_3$)CH$_2$CH$_2$O), 2.93(s,3H,CH$_3$SO$_2$), 2.82(d,J=4.7Hz,3H, CH$_2$N(CH$_3$)CH$_2$)

IR(KBr,cm$^{-1}$): 3240(NH), 2960(≡N$^+$H), 1340 and 1160 (S=O)

EXAMPLE 20

The following compounds (1)–(14) were produced as in Examples 1–12 and 15–19 set forth above.

(1) 1-[2-(N-methylamino)-4-(methanesulfonamido) phenoxy]-2-[2-(3,4-dimethoxyphenethyl)-N-methylamino] ethane hydrochloride $^1$H-NMR (MeOH-d$_4$): δ7.18-6.76(m,6H,ArH), 4.41(t,J= 4.7Hz,2H,CH$_2$N(CH$_3$)CH$_2$CH$_2$O), 3.75(s,3H,CH$_3$O), 3.72 (t,2H,CH$_2$N(CH$_3$)CH$_2$CH$_2$O), 3.70(s,3H,CH$_3$O), 3.38(t,2H, ArCH$_2$CH$_2$N(CH$_3$)CH$_2$), 3.07(t,2H,ArCH$_2$CH$_2$N(CH$_3$) CH$_2$), 2.93(s,3H,CH$_3$SO$_2$NH), 2.91(d,3H,CH$_2$N(CH$_3$) CH$_2$), 2.87(s,3H,CH$_3$NH)

IR(KBr,cm$^{-1}$): 2950(≡N$^+$N), 1330 and 1160(S=O)

MS: 438(MH$^+$)

(2) 1-[2-Chloro-4-methanesulfonamido)phenoxy]-2-[2-(4,5-dimethoxy-2-dimethylaminophenethyl)-N-methylamino]ethane dihydrochloride $^1$H-NMR (MeOH-d$_4$): δ7.24-7.07(m,4H,ArH), 6.93(s,1H, ArH), 4.45(t,J=4.4Hz,2H,CH$_2$N(CH$_3$)CH$_2$CH$_2$O), 3.82(s, 3H,CH$_3$O), 3.70(s,3H,CH$_3$O), 3.77(t,2H,CH$_2$N(CH$_3$) CH$_2$CH$_2$O), 3.55(t,2H,ArCH$_2$CH$_2$N(CH$_3$)CH$_2$), 3.34(t,2H, ArCH$_2$CH$_2$N(CH$_3$)CH$_2$), 3.21(s,6H,(CH$_3$)$_2$N), 3.11(s,3H, CH$_3$SO$_2$NH), 2.84(d,3H,CH$_2$N(CH$_3$)CH$_2$)

IR(KBr,cm$^{-1}$): 2940(≡N$^+$H), 1330 and 1160(S=O)

MS: 486(MH$^+$)

(3) 2-Hydroxy-1-[2-chloro-4-cyanophenoxy]-3-[2-(3,4-dimethoxyphenethyl)-N-methylamino]propane hydrochloride $^1$H-NMR (MeOH-d$_4$): δ7.86(d,J=2.0Hz,1H,ArH), 7.72 (dd,J$_1$=8.6Hz,J$_2$=2.0Hz,1H,ArH), 7.29(d,J=8.7Hz,1H,ArH), 6.96-6.87(m,3H,ArH), 4.44–4.52(m,1H,CH$_2$CH(OH)CH$_2$) 4.24(brs,2H,CH$_2$N(CH$_3$)CH$_2$CH(OH)CH$_2$O), 3.86(s,3H, CH$_3$O), 3.83(s,3H,CH$_3$O), 3.62-3.33(m, 6H,ArCH$_2$CH$_2$N (CH$_3$)CH$_2$CH(OH)CH$_2$O), 3.08(s,3H,CHN(CH$_3$)CH$_2$)

IR(KBr,cm$^{-1}$): 2950(≡N$^+$H), 2240(C≡N)

MS: 405(MH$^+$)

(4) 1-[2-Pyrrolidino-4-(methanesulfonamido)phenoxy]-2-[2-(3,4-dimethoxyphenethyl)-N-methylamino]ethane dihydrochloride $^1$H-NMR (meOH-d$_4$): δ7.58(s,1H,ArH), 7.43(d,J=8.8Hz, 1H,ArH), 7.34(d,J=8.9Hz,1H,ArH), 7.04-6.91(m,3H,ArH), 4.59(t,2H,CH$_2$N(CH$_3$)CH$_2$CH$_2$O), 3.84(s,3H,CH$_3$O), 3.81 (s,3H,CH$_3$O), 4.31-3.37 (m,8H,ArCH$_2$CH$_2$N(CH$_3$)CH$_2$, CH$_2$N(CH$_3$)CH$_2$CH$_2$O, pyrrolidyl(H)), 3.21(t,2H, ArCH$_2$CH$_2$N(CH$_3$)CH$_2$), 3.05(s,3H,CH$_3$SO$_2$NH), 3.02(d, 3H,CH$_2$N(CH$_3$)CH$_2$), 2.18–2.36(m,4H,pyrrolidyl(H))

IR(KBr,cm$^{-1}$): 3240(NH), 2940(≡N$^+$H), 1335 and 1160 (S=O)

(5) 1-[2-Piperidino-4-(methanesulfonamido)phenoxy]-2-[2-(3,4-dimethoxyphenethyl)-N-methylamino]ethane dihydrochloride $^1$H-NMR (MeOH-d$_4$): δ7.65(d,J=2.1Hz,1H,ArH), 7.46 (dd,J$_1$=8.9Hz,J$_2$=2.2Hz,1H,ArH), 7.36(d,J=8.9Hz,1H,ArH), 7.01-6.89(m,3H,ArH), 4.61(t,2H,CH$_2$N(CH$_3$)CH$_2$CH$_2$O), 3.86(s,3H,CH$_3$O), 3.83(s,3H,CH$_3$O), 4.10-3.40 (m 8H CH$_2$N (CH$_3$)CH$_2$CH$_2$O, pyperidinyl (H)) 3.23(t,2H, ArCH$_2$CH$_2$N(CH$_3$)CH$_2$), 3.05(s,3H,CH$_3$SO$_2$NH), 3.02(d, 3H,CH$_2$N(CH$_3$)CH$_2$), 2.47-1.72(m,6H,pyperidinyl(H))

IR(KBr,cm$^{-1}$): 2960(≡N$^+$H), 1330 and 1160(S=O)

(6) 1-[2-(1,2,3,4-Tetrahydroisoquinolino)-4-methanesulfonamido)phenoxyl-2-[2-(3,4-dimethoxyphenethyl)-N-methylamino]ethane $^1$H-NMR (MeOH-d$_4$): δ7.09–7.20(m,4H,ArH), 6.91–7.73 (m,6H,ArH), 4.30(s,2H,

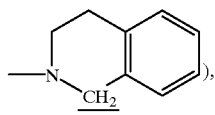

4.13(t,J=6.0Hz,2H,CH$_2$N(CH$_3$)CH$_2$CH$_2$O), 3.87(s,3CH$_3$), 3.45(t,J=5.9Hz,2H, CH$_2$N(CH$_3$)CH$_2$CH$_2$O), 2.95(s,3H, CH$_3$SO$_2$NH), 3.00-2.91(m,4H,

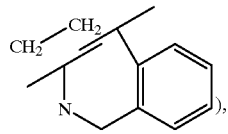

2.80-2.68(m,4H,ArCH$_2$CH$_2$N(CH$_3$)CH$_2$), 2.42(s,3H,CH$_2$N(CH )CH$_2$)

IR(KBr,cm$^{-1}$): 3240(NH), 1320 and 1160(S=O)

(7) 2-Hydroxy-1-[2-chloro-4-(methanesulfonamido) phenoxy]-3-[2-(3,4-dimethoxyphenethyl)-N-methylamino] propane hydrochloride $^1$H-NMR (MeOH-d$_4$): δ7.23-7.02(m,3H,ArH)), 6.85-6.77 (m,3H,ArH)), 4.28–4.40(m,1H,CH$_2$CH(OH)CH$_2$), 4.02(d, 2H,CH$_2$N(CH$_3$)CH$_2$CH(OH)CH$_2$O), 3.73(s,3H,CH$_3$O), 3.70(s,3H,CH$_3$O), 3.53-3.22(m,4H,CH$_2$N(CH$_3$)CH$_2$CH (OH)CH$_2$O), 2.96(t,2H,ArCH$_2$CH$_2$N(CH$_3$)CH$_2$), 2.93(s, 3H,CH$_3$SO$_2$NH), 2.83(d,3H,CH$_2$N(CH$_3$)CH$_2$)

IR(KBr,cm$^{-1}$): 2960(≡N$^+$H), 1330 and 1160(S=O)

(8) 1-[Pyrrol-1-yl-4-(methanesulfonamido)phenoxy]-2-[2-(1-nitro-4,5-dimethoxyphenethyl)-N-methylamino] ethane hydrochloride $^1$H-NMR (MeOH-d$_4$): δ7.75(s,1H,ArH), 7.21–7.30(m, 3H,ArH), 7.03(s,1H,ArH), 6.94(dd,2H,pyrrole(H)), 6.12(dd, 2H,pyrrole(H)), 4.41(t,J=4.6Hz,2H,CH$_2$N(CH$_3$) CH$_2$CH$_2$O), 3.97(s,3H,CH$_3$O), 3.94(s,3H,CH$_3$O), 3.70(t, 2H,CH$_2$N(CH$_3$)CH$_2$CH$_2$O), 3.50-3.29(m,4H,ArCH$_2$CH$_2$N (CH$_3$)CH$_2$), 2.99(s,3H,CH$_3$SI$_2$NH), 2.97(d,3H,CH$_2$N(CH )CH$_2$)

IR(KBr,cm$^{-1}$): 1540(NO$_2$), 1340 and 1160(S=O)

MS: 520(M$^+$)

(9) 1-[2-Pyrrol-1-yl-4-(methanesulfonamido)phenoxy]-2-[2-(1-amino-4,5-dimethoxyphenethyl)-N-methylamino] ethane hydrochloride $^1$H-NMR (MeOH-d$_4$): δ7.24–7.31(m,3H,ArH)), 6.98(dd, 2H,pyrrole(H)), 6.94(s,1H,ArH), 6.19(dd,2H,pyrrole(H)), 4.45(t,J=4.6Hz,2H,CH$_2$N(CH$_3$)CH$_2$CH$_2$O), 3.88(s,3H, CH$_3$O), 3.87(s,3H,CH$_3$O), 3.69(t,2H,CH$_2$N(CH$_3$) CH$_2$CH$_2$O), 3.46(t,2H,ArCH$_2$CH$_2$N(CH$_3$)CH$_2$), 3.11(t,2H, ArCH$_2$CH$_2$N(CH$_3$)CH$_2$), 2.97(s,3H,CH$_3$SO$_2$NH), 2.93(d, 3H,CH$_2$N(CH$_3$)CH$_2$)

IR(KBr,cm$^{-1}$): 3240(NH$_2$), 2950(≡N$^+$H), 1340 and 1160 (S=O)

MS: 489(M$^+$)

(10) 1-[2-Pyrrol-1-yl-4-(methanesulfonamido)phenoxy]-2-[2-(1-methyl-4,5-dimethoxyphenethyl)-N-methylamino] ethane hydrochloride $^1$H-NMR (MeOH-d$_4$): δ7.10–7.21(m,3H,ArH), 6.85(dd, 2H,pyrrole(H)), 6.69(s,1H,ArH), 6.66(s,1H,ArH), 6.08(dd, 2H,pyrrole(H)), 4.22(brs,2H,CH$_2$N(CH$_3$)CH$_2$CH$_2$O), 3.71 (s,3H,CH$_3$O), 3.69(s,3H,CH$_3$O), 3.47(t,2H,CH$_2$N(CH$_3$) CH$_2$CH$_2$O), 3.08(t,2H,ArCH$_2$CH$_2$N(CH$_3$)CH$_2$), 2.86(s,3H, CH$_3$SO$_2$NH), 2.78(t,2H,ArCH$_2$CH$_2$N(CH$_3$)CH$_2$), 2.75(d, 3H,CH$_2$N(CH )CH2), 2.15(s,3H,ArCH$_3$)

IR(KBr,cm$^{-1}$): 2960(≡N$^+$H), 1340 and 1160(S=O)

MS: 488(M$^+$)

(11) 1-[2-Acetamido-4-(methanesulfonamido)phenoxy]-2-[2-(1-methyl-4,5-dimethoxyphenethyl)-N-methylamino] ethane hydrochloride $^1$H-NMR (CDCl$_3$): δ12.06(brs,1H,HCl), 9.64(brs,1H, NHSO$_2$), 8.12(s,1H,NHCOCH$_3$), 7.29(s,1H,ArH), 6.97(s, 1H,ArH), 6.57–6.72(m,3H,ArH), 4.22(t,2H,CH$_2$N(CH$_3$) CH$_2$CH$_2$O), 3.78(s,3H,CH$_3$O), 3.78(s,3H,CH$_3$O), 3.42-3.13 (m,6H,ArCH$_2$CH$_2$N(CH$_3$)CH$_2$CH$_2$O), 2.87(s,3H, CH$_3$SO$_2$NH), 2.87(d,3H,CH$_2$N(CH$_3$)CH$_2$), 2.36(s,3H, ArCH$_3$), 2.24(s,3H,CH$_3$CO)

IR(KBr,cm$^{-1}$): 2940(≡N$^+$H), 1680(C=O), 1340 and 1160(S=O)

MS: 480(M$^+$)

(12) 1-[2-Amino-4-(methanesulfonamido)phenoxy]-2-[2-(4-fluorophenethyl)-N-methylamino]ethane hydrochloride $^1$H-NMR (MeOH-d$_4$): δ7.29–7.41(m,3H,ArH), 7.21-7.07 (m,4H,ArH), 4.53(t,2H,CH$_2$N(CH$_3$)CH$_2$CH$_2$O), 3.66(t,2H, CH$_2$N(CH$_3$)CH$_2$CH$_2$O), 3.47(t,2H,ArCH$_2$CH$_2$N(CH$_3$) CH$_2$CH$_2$O), 3.22(t,2H,ArCH$_2$CH$_2$N(CH$_3$)CH$_2$CH$_2$O), 3.07 (s,3H,CH$_3$SO$_2$NH), 2.97(s,3H,CH$_2$N(CH$_3$)CH$_2$)

IR(KBr,cm$^{-1}$): 3330(NH$_2$), 2960(≡N$^+$H), 1350 and 1180 (S=O)

(13) 1-[2-Amino-4-(methanesulfonamido)phenoxy]-2-[2-(4-methanesulfonamido)phenethyl)-N-methylamino]ethane hydrochloride $^1$H-NMR (MeOH-d$_4$): δ7.41-7.34(m,3H,ArH), 7.21-7.28 (m,4H,ArH), 4.55(t,2H,CH$_2$N(CH$_3$)CH$_2$CH$_2$O), 3.75(t,2H, CH$_2$N(CH$_3$)CH$_2$CH$_2$O), 3.50(t, 2H,ArCH$_2$CH$_2$N(CH$_3$) CH$_2$CH$_2$O), 3.22(t,2H,ArCH$_2$CH$_2$N(CH$_3$)CH$_2$CH$_2$O), 2.98 (s,3H,CH$_3$SO$_2$NH), 2.96(d,3H,CH$_2$N(CH )CH$_2$)

IR(KBr,cm$^{-1}$): 3420(NH$_2$), 2940(≡N$^+$H), 1330 and 1150 (S=O)

(14) 1-[2-Pyrrolidino-4-(methanesulfonamido)phenoxy]-2-[2-[(4-methanesulfonamido)phenethyl]-N-methylamino] ethane dihydrochloride $^1$H-NMR (DMMSO-d$_6$)] δ10.9(brs,1H,HCl), 9.86(brs, 1H,NHSO$_2$CH$_3$), 9.64(s,1H,NHSO$_2$CH$_3$), 7.17–7.49(m,7H, ArH), 4.51(t,2H,CH$_2$N(CH$_3$)CH$_2$CH$_2$O), 3.26–3.83(m,8H, CH$_2$CH$_2$N(CH$_3$)CH$_2$CH$_2$O),

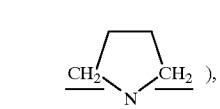

3.12(t,2H,ArCH$_2$CH$_2$N(CH$_3$)CH$_2$), 3.01(s,3H, CH$_3$SO$_2$NH), 2.98(s,3H,CH$_3$SO$_2$NH), 2.93(d,3H,CH$_2$N (CH$_3$)CH$_2$), 1.00–2.18 (m, 4H,

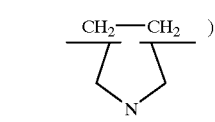

IR(KBr,cm$^{-1}$): 3420(NH$_2$), 2950(≡N$^+$H), 1340 and 1155 (S=O)

MS: 511(MH+)

Experiment 1

Action of prolonging the effective refractory period (ERPc) utilizing the force of contraction in the papillary muscle excised from guinea pig The papillary muscle of the right ventricle was excised from male guinea pigs weighing 400–600 g and suspended in an organ bath containing a Krebs-Ringer solution that was maintained at a temperature of 34° C. and which was saturated with a gaseous mixture (95%:5%=O$_2$:CO$_2$). One side of the muscle was connected to a transducer and the other side was fixed to be given an initial tension of 0.5 g. The isolated papillary muscle was given electrical stimuli (frequency, 1 Hz; duration, 4 msec; voltage, threshold ×1.5) and stabilized for 2 h or more as it was washed at intervals of 15 min. The stabilized isolated papillary muscle was given extra stimuli (stimuli placing an additional pulse after regular pulse at an interval of 10 sec; duration, 4 msec; voltage, threshold ×1.5) to measure the effective refractory period (ERPc) utilizing the contractile force. The experiment at 3 Hz was conducted by the same method under the same conditions as at 1 Hz, except for frequency. Each compound under experiment was used after it was dissolved in 100% dimethyl sulfoxide (DMSO) at a concentration of $10^{-6}$M, followed by dilution with a Krebs-Ringer solution. ERPc was measured for up to 1 h after the administration of each compound under experiment at a concentration of $10^{-6}$M (final concentration of DMSO: 0.1%). The data are expressed as the percentage of the change following the administration of a drug with respect to the control value before the administration of the drug. The results of the experiments are shown in Tables 1 and 2.

TABLE 1

Percent Prolongation of ERPc by Compounds of the Invention

| Compound No. (Example) | Hz | Concentration (M) $10^{-6}$ |
|---|---|---|
| Ex. 2 | 3 | 125.4 ± 0.35 |
| Ex. 3 | 3 | 129.9 ± 2.16 |
| Ex. 4 | 3 | 125.7 ± 0.65 |
| Ex. 5 | 3 | 130.8 ± 2.76 |
| Ex. 7 | 3 | 136.7 ± 2.34 |
| Ex. 8 | 3 | 139.2 ± 1.81 |
| Ex. 9 | 3 | 129.8 ± 1.53 |
| Ex. 10 | 3 | 132.9 ± 2.81 |
| Ex. 11 | 3 | 125.2 ± 1.32 |
| Ex. 15 | 3 | 136.8 ± 1.93 |
| Ex. 16 | 3 | 137.0 ± 0.95 |
| Ex. 17 | 3 | 136.0 ± 1.35 |
| Ex. 18 | 3 | 137.4 ± 2.65 |
| Ex. 19 | 3 | 130.0 ± 2.07 |

TABLE 2

Percent Prolongation Pc Caused by Compounds of the Invention

| Compound No. (Example) | Hz | Concentration (M) $10^{-6}$ | 3 Hz/1 Hz |
|---|---|---|---|
| Ex. 2 | 3 | 125.4 ± 0.35 | 90.7 |
|  | 1 | 128.0 |  |
| Ex. 3 | 3 | 129.9 ± 2.16 | 97.7 |
|  | 1 | 130.6 ± 2.16 |  |
| Ex. 4 | 3 | 125.7 ± 0.65 | 136.0 |
|  | 1 | 118.9 ± 2.45 |  |
| Ex. 5 | 3 | 130.8 ± 2.76 | 95.7 |
|  | 1 | 132.2 ± 1.60 |  |
| Ex. 7 | 3 | 136.7 ± 2.34 | 138.0 |
|  | 1 | 126.6 ± 2.49 |  |
| Ex. 8 | 3 | 139.2 ± 1.81 | 126.1 |
|  | 1 | 131.1 ± 2.51 |  |
| Ex. 9 | 3 | 129.8 ± 1.53 | 73.8 |
|  | 1 | 140.4 ± 4.67 |  |
| Ex. 10 | 3 | 132.9 ± 2.81 | 104.4 |
|  | 1 | 131.5 ± 1.21 |  |
| Ex. 11 | 3 | 125.2 ± 1.32 | 76.8 |
|  | 1 | 132.8 ± 1.85 |  |
| Ex. 15 | 3 | 136.8 ± 1.93 | 84.8 |
|  | 1 | 143.4 ± 4.16 |  |

TABLE 2-continued

Percent Prolongation Pc Caused by Compounds of the Invention

| Compound No. (Example) | Hz | Concentration (M) $10^{-6}$ | 3 Hz/1 Hz |
|---|---|---|---|
| Ex. 16 | 3 | 137.0 ± 0.95 | 97.3 |
|  | 1 | 138.0 ± 2.99 |  |
| Ex. 17 | 3 | 136.0 ± 1.35 | 105.9 |
|  | 1 | 134.0 ± 1.89 |  |
| Ex. 18 | 3 | 137.4 ± 2.65 | 97.3 |
|  | 1 | 140.7 ± 2.90 |  |
| Ex. 19 | 3 | 130.0 ± 2.07 | 114.1 |
|  | 1 | 126.3 ± 1.42 |  |
| E-4031* | 3 | 128.1 ± 2.26 | 72.0 |
|  | 1 | 139.3 ± 2.40 |  |

Note) *E-4031 = 4'[(1-[2-(6-methyl-2-pyridyl)ethyl]-4-piperidyl]-carbonyl] methanesulfonanilide As is clear from the experiment results set forth above, compounds of the invention present by far higher ratios of 3 Hz/1 Hz than the compound E-4031 which has already been developed as an antiarrhythmic drug and, hence, they are advanced antiarrhythmic drugs that are improved in terms of the proarrhythmic effect due to reverse use dependency which is a drawback of the known antiarrhythmic drugs of class III.

Experiment 2

Action of prolonging the action potential duration ($APD_{90}$) of the papillary muscle excised from guinea pig The papillary muscle of the right ventricle was excised from male guinea pigs weighing 400–600 g and fixed in an acrylic organ bath. A Krebs-Ringer solution that was maintained at a temperature of 34° C. and which was saturated with a gaseous mixture (95%:5%=$O_2$:$CO_2$) was perfused into the organ bath. The fixed isolated papillary muscle was given electrical stimuli (frequency, 1 Hz or 3 Hz; duration, 2 msec; voltage, threshold ×1.5) and stabilized for about 2 h; thereafter, glass microelectrodes (20–30 MΩ) filled with a solution of 3M KCl were utilized to measure the action potential duration ($APD_{90}$). Each compound under experiment was used after it was dissolved in 100% dimethyl sulfoxide (DMSO), followed by dilution with a Krebs-Ringer solution to a concentration of $10^{-6}$M (final DMSO concentration: 0.1%). The action of prolonging the action potential duration as observed for about one hour after drug administration is expressed as the percentage of the change with respect to the control value before drug administration. The results of the experiment are shown in Tables 3 and 4.

TABLE 3

Percent Prolongation of $APD_{90}$ by Compounds of the Invention

| Compound No. (Example) | Hz | Concentration (M) $10^{-6}$ | N |
|---|---|---|---|
| Ex. 1 | 1 | 159.6 | 8 |
| 13-(13) | 1 | 123.2 | 1 |
| 13-(1) | 1 | 130.1 | 1 |
| 13-(10) | 1 | 123.0 | 1 |
| 20-(3) | 1 | 137.7 | 2 |

TABLE 4

Percent Prolongation in $APD_{90}$ Caused by
Compounds of the Invention
(mean ± standard error)

| Compound No. (Example) | Hz | Concentration (M) $10^{-6}$ | N | 3 Hz/1 Hz |
|---|---|---|---|---|
| Ex. 1 | 3 | 121.6 ± 6.23 | 3 | 36.2 |
|  | 1 | 159.6 ± 6.23 | 8 |  |
| Ex. 5 | 3 | 127.9 ± 4.26 | 5 | 110.3 |
|  | 1 | 125.3 ± 1.47 | 3 |  |
| Ex. 10 | 3 | 129.1 ± 3.46 | 4 | 69.6 |
|  | 1 | 141.8 ± 2.45 | 3 |  |
| Ex. 11 | 3 | 129.8 ± 4.70 | 3 | 92.7 |
|  | 1 | 139.5 ± 3.05 | 2 |  |
| Ex. 20(3) | 3 | 117.7 ± 4.11 | 3 | 47.0 |
|  | 1 | 137.7 ± 4.95 | 2 |  |
| E-4031* | 3 | 118.4 ± 2.66 | 4 | 37.6 |
|  | 1 | 149.0 ± 1.67 | 3 |  |

Note) *E-4031 = 4'-[[1-[2-(6-methyl-2-pyridyl)ethyl]-4-piperidyl]carbonyl]methanesulfonanilide

INDUSTRIAL APPLICABILITY

As is clear from the experimental results set forth above, the compounds of the invention present by far higher ratios of 3 Hz/1 Hz than E-4031 which has already been developed as an antiarrhythmic drug and, hence, they are advanced antiarrhythmic drugs that are improved in terms of the proarrhythmic effect due to reverse use dependency which is a drawback of the known antiarrhythmic drugs of class III.

What is claimed is:

1. An amine derivative of the general formula (I) set forth below or a salt thereof:

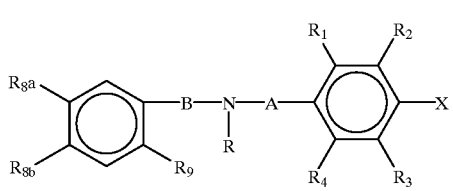

(I)

(wherein

A denotes the general formula —$(CH_2)_m$—, —$(CH_2)_m$—O—, —$(CH_2)_m$—NH— or —$(CH_2)_m$—$SO_2$—, where a hydrogen atom in the —$(CH_2)_m$— moiety may be substituted by one or more hydroxyl groups;

B denotes a group of the general formula —$(CH_2)_n$—, —$NR_7$—$(CH_2)_n$— or —CONH—$(CH_2)_n$—;

$R_1$, $R_2$, $R_3$, and $R_4$ denote each independently a hydrogen atom, a halogen atom, a cyano group, a lower alkyl group, a lower alkoxy group, a lower alkanoyl group, a nitro group, a hydroxyl group, a lower alkylsulfonyloxy group, a phenoxymethyl group, a heterocyclic group or the group of the general formula —$NR_5R_6$, where $R_5$ and $R_6$ denote each independently a hydrogen atom, a lower alkanoyl group, a lower alkyl group or a heterocyclic group;

$R_9$ denotes a hydrogen atom, a halogen atom, a nitro group, an amino group, a lower alkyl group, a lower alkanoylamino group or a lower alkylamino group;

$R_{8a}$ and $R_{8b}$ denote the same halogen atom or lower alkoxy group or, alternatively, when $R_{8a}$ is a hydrogen atom, $R_{8b}$ denotes a lower alkylsulfonylamino group or a halogen atom (provided that when $R_{8a}$ is a hydrogen atom and $R_{8b}$ is a lower alkylsulfonylamino group, $R_1$ denotes a group of the general formula —$NR_5R_6$) or a heterocyclic group);

R denotes a lower alkyl group or an aryl group;

$R_7$ denotes a hydrogen atom or a lower alkyl group;

X denotes a group of the general formula —$NR_{10}R_{11}$, a nitro group, a cyano group or a heterocyclic group, where $R_{10}$ and $R_{11}$ denote each independently a hydrogen atom or a lower alkylsulfonyl group;

m and n denote an integer of 0–3.

2. A compound or a salt thereof according to claim 1, wherein $R_1$, $R_2$, $R_3$ and $R_4$ denote each independently a hydrogen atom, a halogen atom, a cyano group, a lower alkyl group having 1–6 carbon atoms, a lower alkoxy group having 1–6 carbon atoms, a lower alkanoyl group having 1–6 carbon atoms in the alkyl moiety, a nitro group, a hydroxyl group, a lower alkylsulfonyloxy group having 1–6 carbon atoms, a 5-membered heterocyclic group or a group of the general formula —$NR_5R_6$, where $R_5$ and $R_6$ denote each independently a hydrogen atom, a lower alkanoyl group having 1–6 carbon atoms in the alkyl moiety or a lower alkyl group having 1–6 carbon atoms;

$R_9$ denotes a hydrogen atom, a halogen atom, a nitro group, an amino group, a lower alkanoylamino group having 1–6 carbon atoms in the alkyl moiety or a lower alkylamino group having 1–6 carbon atoms;

$R_{8a}$ and $R_{8b}$ denote the same halogen atom or lower alkoxy group having 1–6 carbon atoms;

R denotes a lower alkyl group having 1–6 carbon atoms or a phenyl group;

$R_7$ denotes a hydrogen atom or a lower alkyl group having 1–6 carbon atoms;

X denotes a group of the general formula —$NR_{10}R_{11}$, a nitro group, a cyano group or an imidazolyl group, where $R_{10}$ and $R_{11}$ denote each independently a hydrogen atom or a lower alkylsulfonyl group having 1–6 carbon atoms; and m and n are an integer of and 0–2.

3. A compound or a salt thereof according to claim 1, wherein $R_1$, $R_2$, $R_3$ and $R_4$ denote each independently a hydrogen atom, a fluorine atom, a chlorine atom, a bromine atom, an iodine atom, a cyano group, a methyl group, a methoxy group, an acetyl group, a nitro group, a hydroxyl group, a methylsulfonyloxy group, a phenoxy-methyl group, a pyrrolyl group or a group of the general formula —$NR_5R_6$, where $R_5$ and $R_6$ denote each independently a hydrogen atom, an acetyl group or a methyl group;

$R_9$ denotes a hydrogen atom, a nitro group, an amino group or a lower alkanoylamino group having 1–6 carbon atoms in the alkyl moiety;

$R_{8a}$ and $R_{8b}$ which are the same denote a chlorine atom or a methoxy group;

R denotes a lower alkyl group having 1–3 carbon atoms or a phenyl group;

$R_7$ denotes a hydrogen atom or a methyl group;

X denotes a group of the general formula —$NR_{10}R_{11}$, a nitro group, a cyano group or a 1-imidazolyl group, where $R_{10}$ and $R_{11}$ denote each independently a hydrogen atom or a methylsulfonyl group; and m and n are an integer of 0–2.

4. A compound or a salt thereof according to claim 1, wherein

A denotes the group —(CH$_2$)$_2$—, —CH$_2$—O—, —(CH$_2$)$_2$—O—, —CH$_2$—NH— or —(CH$_2$)$_2$—SO$_2$—;

B denotes the group —(CH$_2$)$_2$—, —cONH—(CH$_2$)$_2$— or —NH—(CH$_2$)$_2$—;

R$_1$ denotes a hydrogen atom, a halogen atom, a nitro group, a 1-pyrrolyl group, an acetamido group, an amino group, a dimethylamino group, a cyano group, a lower alkyl group having 1–3 carbon atoms, a hydroxyl group, a methanesulfonyloxy group or a methanesulfonylamido group;

R$_2$ denotes a hydrogen atom, a nitro group or a halogen atom;

R$_3$ denotes a hydrogen atom or a nitro group;

R$_4$ denotes a hydrogen atom, a lower alkyl group having 1–3 carbon atoms or a halogen atom;

R$_{8a}$ and R$_{8b}$ which are the same denote a chlorine atom or a methoxy group;

R$_9$ denotes a hydrogen atom, a lower alkyl group having 1–3 carbon atoms, an amino group or a nitro group;

R denotes a lower alkyl group having 1–3 carbon atoms or a phenyl group; and

X denotes a methanesulfonylamido group, a 1-imidazolyl group, a nitro group or a cyano group.

5. A compound or a salt thereof according to claim 1, wherein

A denotes —(CH$_2$)—O—, —(CH$_2$)$_2$—O— or —(CH$_2$)$_2$—NH—;

B denotes —(CH$_2$)$_2$—;

R$_1$ denotes a hydrogen atom, a halogen atom, a nitro group, a 1-pyrrolyl group, an acetamido group, an amino group or a dimethylamino group;

R$_2$ denotes a hydrogen atom or a nitro group;

R$_3$ and R$_4$ denote a hydrogen atom;

R$_{8a}$ and R$_{8b}$ which are the same denote a chlorine atom or a methoxy group;

R$_9$ denotes a hydrogen atom, a methyl group, an ethyl group or an amino group;

R denotes a methyl group; and

X denotes a methanesulfonylamido group, a 1-imidazolyl group or a nitro group.

6. 1-[4-Methanesulfonylamido-2-(1H-pyrrol-1-yl)phenoxy]-2-[N-(3,4-dimethoxyphenethyl)-N-methylamino]ethane or a salt thereof.

7. 1-(2-Acetamido-4-methanesulfonamidophenoxy)-2-[N-(3,4-dimethoxyphenethyl)-N-methylamino]ethane or a salt thereof.

8. 1-(4-Methanesulfonamidophenoxy)-2-[N-(3,4-dichlorophenethyl)-N-methylamino]ethane or a salt thereof.

9. A process for producing an amine derivative of the general formula (I) or a salt thereof, (A) reacting a compound of the general formula (II) set forth below or a salt thereof with a compound of the general formula (III) set forth below or a salt thereof;

(B) reducing a compound of the general formula (Ia) set forth below or a salt thereof to produce a compound of the general formula (Ib) or a salt thereof;

(C) reacting a compound of the general formula (Ic) set forth below or a salt thereof with an alkanesulfonyl halide to produce a compound of the general formula (Id) set forth below or a salt thereof;

(D) reacting a compound of the general formula (II) set forth below or a salt thereof with a compound of the general formula (IV) set forth below or a salt thereof to produce a compound of the general formula (V) set forth below or a salt thereof and reacting the thus produced compound (V) with a compound of the general formula (VI) set forth below or a salt thereof to produce a compound of the general formula (Ie) or a salt thereof; or (E) reacting a compound of the general formula (VII) set forth below or a salt thereof with a compound of the general formula (VIII) set forth below or a salt thereof to produce a compound of the general formula (If) set forth below or a salt thereof:

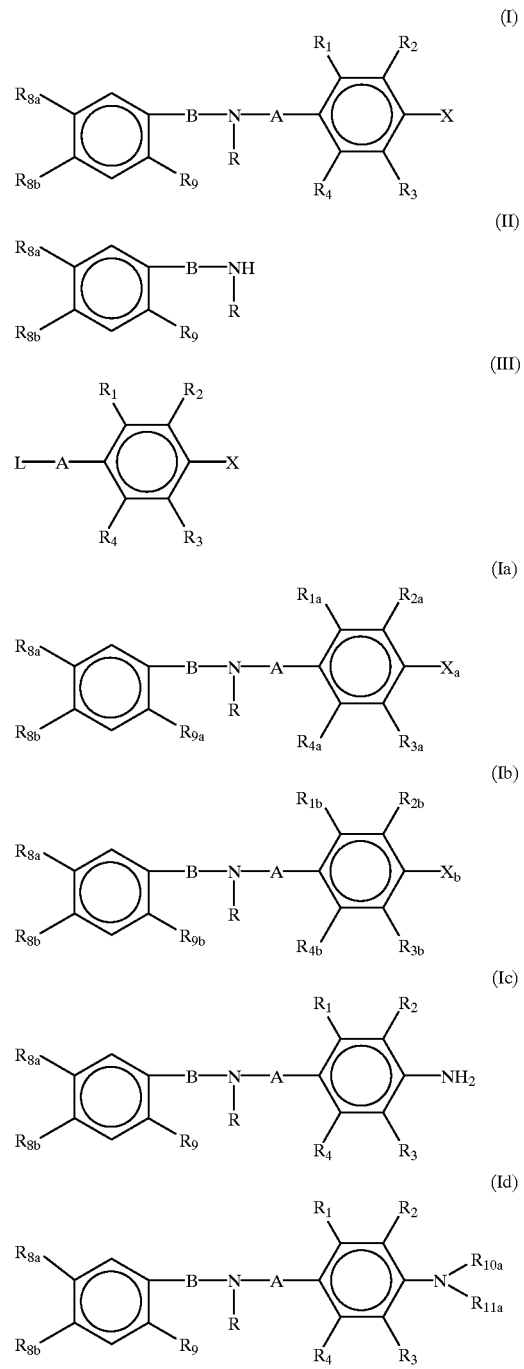

-continued

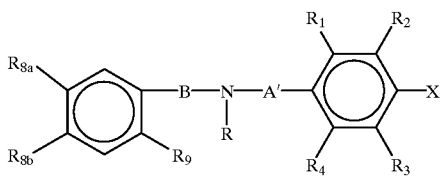

(Ie)

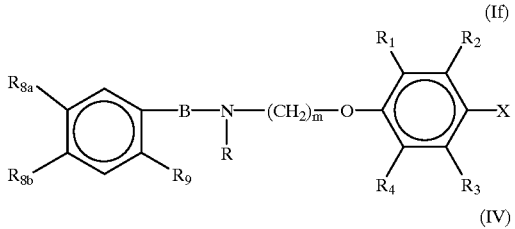

(If)

L—A'H   (IV)

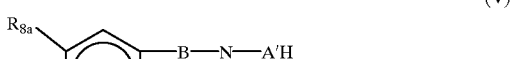

(V)

(VI)

(VII)

(VIII)

(wherein
A denotes a group of the general formula —(CH$_2$)$_m$—, —(CH$_2$)$_m$—O—, —(CH$_2$)$_m$—NH— or —(CH$_2$)$_m$—SO$_2$—, where a hydrogen atom in the —(CH$_2$)$_m$— moiety may be substituted by no more than one hydroxy group;

B denotes a group of the general formula —(CH$_2$)$_n$—, —NR$_7$—(CH$_2$)$_n$— or —CONH—(CH$_2$)$_n$—;

R$_1$, R$_2$, R$_3$ and R$_4$ denote each independently a hydrogen atom, a halogen atom, a cyano group, a lower alkyl group, a lower alkoxy group, a lower alkanoyl group, a nitro group, a hydroxy group, a lower alkylsulfonyloxy group, a phenoxymethyl group, a heterocyclic group or a group of the general formula —NR$_5$R$_6$, where R$_5$ and R$_6$ denote each independently a hydrogen atom, a lower alkanoyl group, a lower alkyl group or a heterocyclic group;

R$_9$ denotes a hydrogen atom, a halogen atom, a nitro group, an amino group, a lower alkyl group, a lower alkanoylamino group or a lower alkylamino group;

R$_{8a}$ and R$_{8b}$ denote the same halogen atom or lower alkoxy group or, alternatively, when R$_{8a}$ denotes a hydrogen atom, R$_{8b}$ denotes a lower alkylsulfonylamino group or a halogen atom (provided that when R$_{8a}$ is a hydrogen atom and R$_{8b}$ is a lower alkylsulfonylamino group, R$_1$ denotes a group of the general formula —NR$_5$R$_6$ or a heterocyclic group);

R denotes a lower alkyl group or an aryl group;

R$_7$ denotes a hydrogen atom or a lower alkyl group;

X denotes a group of the general formula —NR$_{10}$R$_{11}$, a nitro group, a cyano group or a heterocyclic group, where R$_{10}$ and R$_{11}$ denote each independently a hydrogen atom or a lower alkylsulfonyl group;

m denotes an integer of 0–3;

n denotes an integer of 0–3;

L denotes a reactive leaving group;

A' has the same meaning as A, except that it is not —(CH$_2$)$_m$—;

one of R$_{10a}$ and R$_{11a}$ is a hydrogen atom while the other is a lower alkylsulfonyl group;

R$_{1a}$, R$_{2a}$, R$_{3a}$, R$_{4a}$, R$_{9a}$ and X$_a$ have the same meanings as the above R$_1$, R$_2$, R$_3$, R$_4$, R$_9$ and X, respectively, provided that at least one of them is a nitro group; and R$_{1b}$, R$_{2b}$, R$_{3b}$, R$_{4b}$, R$_{9b}$ and X$_b$ have the same meanings as the above R$_1$, R$_2$, R$_3$, R$_4$, R$_9$ and X, respectively, provided that at least one of them is an amino group.

10. A process for producing an amine derivative of the general formula (I) or a salt thereof reacting a compound of the general formula (II) set forth below or a salt thereof with a compound of the general formula (III) set forth below or a salt thereof:

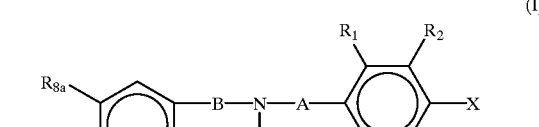

(I)

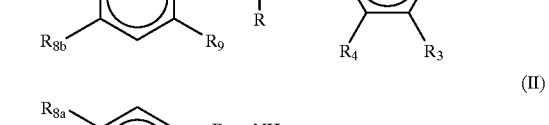

(II)

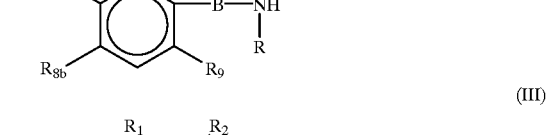

(III)

wherein
A denotes a group of the general formula —(CH$_2$)$_m$—, —(CH$_2$)$_m$—O—, —(CH$_2$)$_m$—NH— or —(CH$_2$)$_m$—SO$_2$—, where a hydrogen atom in the —(CH$_2$)$_m$— moiety may be substituted by no more than one hydroxy group;

B denotes the general formula —(CH$_2$)$_n$—, —NR$_7$—(CH$_2$)$_n$— or —CONH—(CH$_2$)$_n$;

R$_1$, R$_2$, R$_3$ and R$_4$ denote each independently a hydrogen atom, a halogen atom, a cyano group, a lower alkyl group, a lower alkoxy group, a lower alkanoyl group, a nitro group, a hydroxy group, a lower alkylsulfonyloxy group, a phenoxymethyl group, a heterocyclic group or a group of the general formula —NR$_5$R$_6$, where R$_5$ and R$_6$ denote each independently a hydrogen atom, a lower alkanoyl group, a lower alkyl group or a heterocyclic group;

R$_9$ denotes a hydrogen atom, a halogen atom, a nitro group, an amino group, a lower alkyl group, a lower alkanoylamino group or a lower alkylamino group;

R$_{8a}$ and R$_{8b}$ denote the same halogen atom or lower alkoxy group or, alternatively, when R$_{8a}$ denotes a hydrogen atom, R$_{8b}$ denotes a lower alkylsulfonylamino group or a halogen atom (provided that when R$_{8a}$ is a hydrogen atom and R$_{8b}$ is a lower alkylsulfonylamino group, R$_1$ denotes a group of the general formula —NR$_5$R$_6$ or a heterocyclic group);

R denotes a lower alkyl group or an aryl group;

R$_7$ denotes a hydrogen atom or a lower alkyl group;

X denotes a group of the general formula —NR$_{10}$R$_{11}$, a nitro group, a cyano group or a heterocyclic group, where R$_{10}$ and R$_{11}$ denote each independently a hydrogen atom or a lower alkylsulfonyl group;

m denotes an integer of 0–3;

n denotes an integer of 0–3; and

L denotes a reactive leaving group.

11. A process for producing an amine derivative of the general formula (I) or a salt thereof reducing a compound of the general formula (Ia) set forth below or a salt thereof to produce a compound of the general formula (Ib) set forth below or a salt thereof:

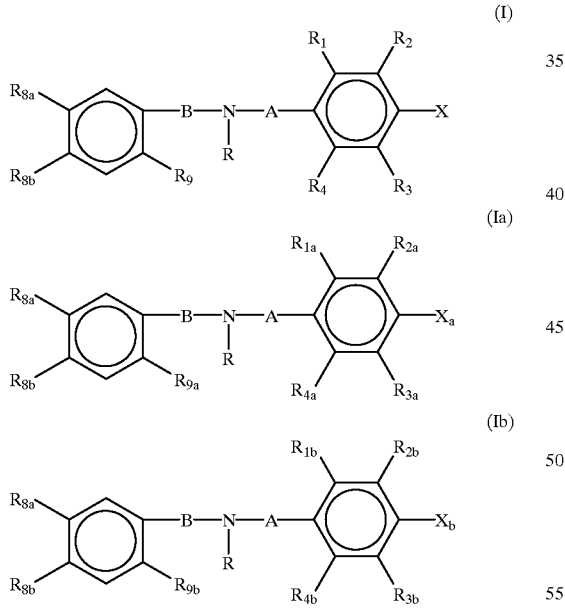

(wherein

A denotes a group of the general formula —(CH$_2$)$_m$—, —(CH$_2$)$_m$—O—, —(CH$_2$)$_m$—NH— or —(CH$_2$)$_m$—SO$_2$—, where a hydrogen atom in the —(CH$_2$)$_m$— moiety may be substituted by at least one hydroxy group;

B denotes a group of the general formula —(CH$_2$)$_n$—, —NR$_7$—(CH$_2$)$_n$— or —CONH—(CH$_2$)$_n$—;

R$_1$, R$_2$, R$_3$ and R$_4$ denote each independently a hydrogen atom, a halogen atom, a cyano group, a lower alkyl group, a lower alkoxy group, a lower alkanoyl group, a nitro group, a hydroxy group, a lower alkylsulfonyloxy group, a phenoxymethyl group, a heterocyclic group or a group of the general formula —NR$_5$R$_6$, where R$_5$ and R$_6$ denote each independently a hydrogen atom, a lower alkanoyl group, a lower alkyl group or a heterocyclic group;

R$_9$ denotes a hydrogen atom, a halogen atom, a nitro group, an amino group, a lower alkyl group, a lower alkanoylamino group or a lower alkylamino group;

R$_{8a}$ and R$_{8b}$ denote the same halogen atom or a lower alkoxy group or, alternatively, when R$_{8a}$ denotes a hydrogen atom, R$_{8b}$ denotes a lower alkylsulfonylamino group or a halogen atom (provided that when R$_{8a}$ is a hydrogen atom and R$_{8b}$ is a lower alkylsulfonylamino group, R$_1$ denotes a group of the general formula —NR$_5$R$_6$ or a heterocyclic group);

R denotes a lower alkyl group or an aryl group;

R$_7$ denotes a hydrogen atom or a lower alkyl group;

X denotes a group of the general formula —NR$_{10}$R$_{11}$, a nitro group, a cyano group or a heterocyclic group, where R$_{10}$ and R$_{11}$ denote each independently a hydrogen atom or a lower alkylsulfonyl group;

m denotes an integer of 0–3;

n denotes an integer of 0–3;

R$_{1a}$, R$_{2a}$, R$_{3a}$, R$_{4a}$, R$_{9a}$ and X$_a$ have the same meanings as the above R$_1$, R$_2$, R$_3$, R$_4$, R$_9$ and X, respectively, provided that at least one of them is a nitro group; and R$_{1b}$, R$_{2b}$, R$_{3b}$, R$_{4b}$, R$_{9b}$ and X$_b$ have the same meanings as the above R$_1$, R$_2$, R$_3$, R$_4$, R$_9$ and X, respectively, provided that at least one of them is an amino group.

12. A process for producing an amine derivative of the general formula (I) or a salt thereof by reacting a compound of the general formula (Ic) set forth below or a salt thereof with an alkanesulfonyl halide to produce a compound of the general formula (Id) set forth below or a salt thereof:

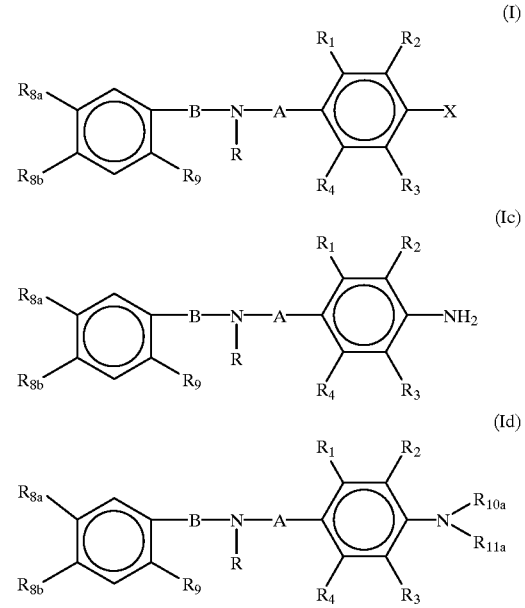

(wherein

A denotes a group of the general formula —(CH$_2$)$_m$—, —(CH$_2$)$_m$—O—, —(CH$_2$)$_m$—NH— or —(CH$_2$)$_m$—SO$_2$—, where a hydrogen atom in the —(CH$_2$)$_m$— moiety may be substituted by at least one hydroxy group;

B denotes a group of the general formula —(CH$_2$)$_n$—, —NR$_7$—(CH$_2$)$_n$— or —CONH—(CH$_2$)$_n$—;

R$_1$, R$_2$, R$_3$ and R$_4$ denote each independently a hydrogen atom, a halogen atom, a cyano group, a lower alkyl group, a lower alkoxy group, a lower alkanoyl group, a nitro group, a hydroxy group, a lower alkylsulfonyloxy group, a phenoxymethyl group, a heterocyclic group or a group of the general formula —NR$_5$R$_6$, where R$_5$ and R$_6$ denote each independently a hydrogen atom, a lower alkanoyl group, a lower alkyl group or a heterocyclic group;

R$_9$ denotes a hydrogen atom, a halogen atom, a nitro group, an amino group, a lower alkyl group, a lower alkanoylamino group or a lower alkylamino group;

R$_{8a}$ and R$_{8b}$ denote the same halogen atom or lower alkoxy group or, alternatively, when R$_{8a}$ denotes a hydrogen atom, R$_{8b}$ denotes a lower alkylsulfonylamino group or a halogen atom (provided that when R$_{8a}$ is a hydrogen atom and R$_{8b}$ is a lower alkylsulfonylamino group, R$_1$ denotes a group of the general formula —NR$_5$R$_6$ or a heterocyclic group);

R denotes a lower alkyl group or an aryl group;

R$_7$ denotes a hydrogen atom or a lower alkyl group;

X denotes a group of the general formula —NR$_{10}$R$_{11}$, a nitro group, a cyano group or a heterocyclic group, where R$_{10}$ and R$_{11}$ denote each independently a hydrogen atom or a lower alkylsulfonyl group;

m denotes an integer of 0–3;

n denotes an integer of 0–3; and one of R$_{10a}$ and R$_{11a}$ is a hydrogen atom while the other is a lower alkylsulfonyl group.

13. A process for producing an amine derivative of the general formula (I) or a salt thereof reacting a compound of the general formula (II) set forth below or a salt thereof with a compound of the general formula (IV) set forth below or a salt thereof to produce a compound of the general formula (V) set forth below or a salt thereof and reacting the thus produced compound (V) with a compound of the general formula (VI) set forth below or a salt thereof to produce a compound of the general formula (Ie) set forth below or a salt thereof:

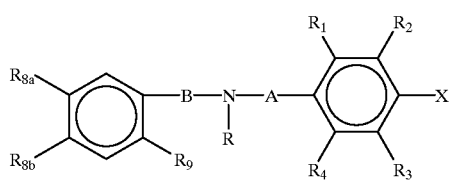
(I)

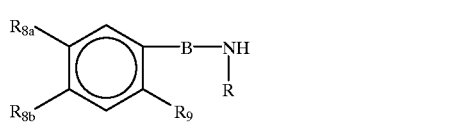
(II)

(IV)

(V)

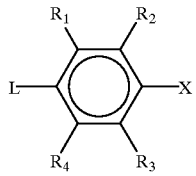
(VI)

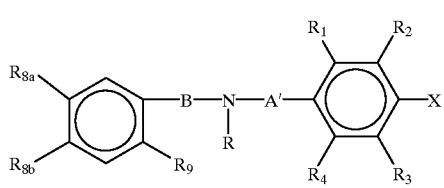
(Ie)

(wherein

A denotes a group of the general formula —(CH$_2$)$_m$—, —(CH$_2$)$_m$—O—, —(CH$_2$)$_m$—NH— or —(CH$_2$)$_m$—SO$_2$—, where a hydrogen atom in the —(CH$_2$)$_m$— moiety may be substituted by at least one hydroxy group;

B denotes a group of the general formula —(CH$_2$)$_n$—, —NR$_7$—(CH$_2$)$_n$— or —CONH—(CH$_2$)$_n$—;

R$_1$, R$_2$, R$_3$ and R$_4$ denote each independently a hydrogen atom, a halogen atom, a cyano group, a lower alkyl group, a lower alkoxy group, a lower alkanoyl group, a nitro group, a hydroxy group, a lower alkylsulfonyloxy group, a phenoxymethyl group, a heterocyclic group or a group of the general formula —NR$_5$R$_6$, where R$_5$ and R$_6$ denote each independently a hydrogen atom, a lower alkanoyl group, a lower alkyl group or a heterocyclic group;

R$_9$ denotes a hydrogen atom, a halogen atom, a nitro group, an amino group, a lower alkyl group, a lower alkanoylamino group or a lower alkylamino group;

R$_{8a}$ and R$_{8b}$ denote the same halogen atom or lower alkoxy group or, alternatively, when R$_{8a}$ denotes a hydrogen atom, R$_{8b}$ denotes a lower alkylsulfonylamino group or a halogen atom (provided that when R$_{8a}$ is a hydrogen atom and R$_{8b}$ is a lower alkylsulfonylamino group, R$_1$ denotes a group of the general formula —NR$_5$R$_6$ or a heterocyclic group);

R denotes a lower alkyl group or an aryl group;

R$_7$ denotes a hydrogen atom or a lower alkyl group;

X denotes a group of the general formula —NR$_{10}$R$_{11}$, a nitro group, a cyano group or a heterocyclic group, where R$_{10}$ and R$_{11}$ denote each independently a hydrogen atom or a lower alkylsulfonyl group;

m denotes an integer of 0–3;

n denotes an integer of 0–3;

L denotes a reactive leaving group; and

A' has the same meaning as A, except that it is not —(CH$_2$)$_m$—.

14. A process for producing an amine derivative of the general formula (I) or a salt thereof reacting a compound of the general formula (VII) set forth below or a salt thereof with a compound of the general formula (VIII) set forth below or a salt thereof to produce a compound of the general formula (If) set forth below or a salt thereof:

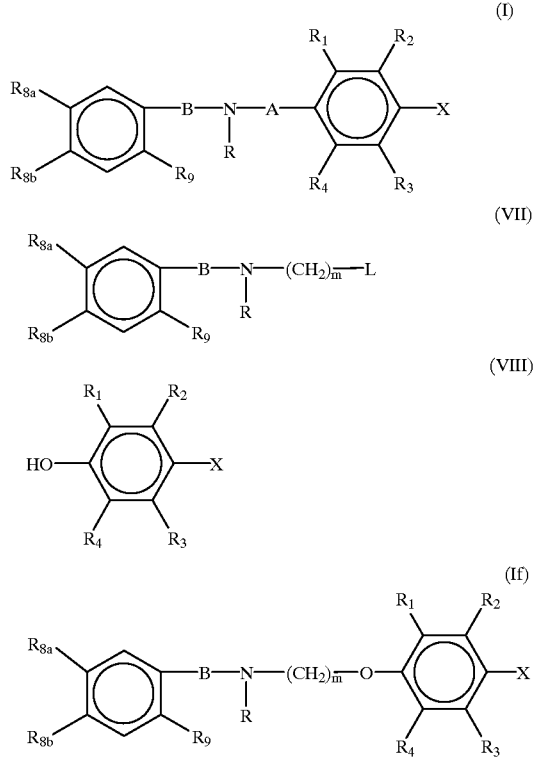

(wherein

A denotes a group of the general formula $-(CH_2)_m-$, $-(CH_2)_m-O-$, $-(CH_2)_m-NH-$ or $-(CH_2)_m-SO_2-$, where a hydrogen atom in the $-(CH_2)_m-$ moiety may be substituted by at least one hydroxy group;

B denotes a group of the general formula $-(CH_2)_n-$, $-NR_7-(CH_2)_n-$ or $-CONH-(CH_2)_n-$;

$R_1$, $R_2$, $R_3$ and $R_4$ denote each independently a hydrogen atom, a halogen atom, a cyano group, a lower alkyl group, a lower alkoxy group, a lower alkanoyl group, a nitro group, a hydroxy group, a lower alkylsulfonyloxy group, a phenoxymethyl group, a heterocyclic group or a group of the general formula $-NR_5R_6$, where $R_5$ and $R_6$ denote each independently a hydrogen atom, a lower alkanoyl group, a lower alkyl group or a heterocyclic group;

$R_9$ denotes a hydrogen atom, a lower alkyl group, a halogen atom, a nitro group, an amino group, a lower alkanoylamino group or a lower alkylamino group;

$R_{8a}$ and $R_{8b}$ denote the same halogen atom or lower alkoxy group or, alternatively, when $R_{8a}$ denotes a hydrogen atom, $R_{8b}$ denotes a lower alkylsulfonylamino group or a halogen atom (provided that when $R_{8a}$ is a hydrogen atom and $R_{8b}$ is a lower alkylsulfonylamino group, $R_1$ denotes a group of the general formula $-NR_5R_6$ or a heterocyclic group);

R denotes a lower alkyl group or an aryl group;

$R_7$ denotes a hydrogen atom or a lower alkyl group;

X denotes a group of the general formula $-NR_{10}R_{11}$, a nitro group, a cyano group or a heterocyclic group, where $R_{10}$ and $R_{11}$ denote each independently a hydrogen atom or a lower alkylsulfonyl group;

m denotes an integer of 0–3;

n denotes an integer of 0–3; and

L denotes a reactive leaving group.

15. An antiarrhythmic drug composition containing at least one compound of the general formula (I) of claim 1 or a salt thereof as an active ingredient together with a pharmaceutically acceptable vehicle.

16. An antiarrhythmic drug composition containing at least one compound of the general formula (I) of claim 6 or a salt thereof as an active ingredient together with a pharmaceutically acceptable vehicle.

17. An antiarrhythmic drug composition containing at least one compound of the general formula (I) of claim 7 or a salt thereof as an active ingredient together with a pharmaceutically acceptable vehicle.

18. An antiarrhythmic drug composition containing at least one compound of the general formula (I) of claim 8 or a salt thereof as an active ingredient together with a pharmaceutically acceptable vehicle.

* * * * *